US012668595B2

(12) United States Patent
Cheng et al.

(10) Patent No.: US 12,668,595 B2
(45) Date of Patent: Jun. 30, 2026

(54) AZA-ERGOLINE DERIVATIVE AND PREPARATION METHOD THEREFOR AND APPLICATION THEREOF

(71) Applicants: SHANGHAITECH UNIVERSITY, Shanghai (CN); CENTER FOR EXCELLENCE IN MOLECULAR CELL SCIENCE, CHINESE ACADEMY OF SCIENCES, Shanghai (CN)

(72) Inventors: Jianjun Cheng, Shanghai (CN); Sheng Wang, Shanghai (CN); Huan Wang, Shanghai (CN); Luyu Fan, Shanghai (CN); Zhangcheng Chen, Shanghai (CN); Jing Yu, Shanghai (CN); Jianzhong Qi, Shanghai (CN); Fen Nie, Shanghai (CN)

(73) Assignees: SHANGHAITECH UNIVERSITY, Shanghai (CN); CENTER FOR EXCELLENCE IN MOLECULAR CELL SCIENCE, CHINESE ACADEMY OF SCIENCES, Shanghai (CN)

( * ) Notice: Subject to any disclaimer, the term of this patent is extended or adjusted under 35 U.S.C. 154(b) by 403 days.

(21) Appl. No.: 18/274,889

(22) PCT Filed: Jan. 29, 2022

(86) PCT No.: PCT/CN2022/075094

§ 371 (c)(1),
(2) Date: Jul. 28, 2023

(87) PCT Pub. No.: WO2022/161493

PCT Pub. Date: Aug. 4, 2022

(65) Prior Publication Data

US 2024/0124456 A1 Apr. 18, 2024

(30) Foreign Application Priority Data

Feb. 1, 2021 (CN) ........................ 202110138249.9
Sep. 29, 2021 (CN) ........................ 202111153079.8

(51) Int. Cl.

| | |
|---|---|
| ***C07D 471/18*** | (2006.01) |
| ***A61K 31/4995*** | (2006.01) |
| ***A61P 25/18*** | (2006.01) |
| ***A61P 25/24*** | (2006.01) |
| ***C07D 471/14*** | (2006.01) |
| ***C07D 519/00*** | (2006.01) |

(52) U.S. Cl.

CPC ............ *C07D 471/14* (2013.01); *A61P 25/18* (2018.01); *A61P 25/24* (2018.01); *C07D 519/00* (2013.01); *C07B 2200/13* (2013.01)

(58) Field of Classification Search

CPC ... C07D 471/18; A61K 31/4995; A61P 25/18; A61P 25/28; A61P 25/16; A61P 25/24

USPC .......................................... 544/343; 514/250

See application file for complete search history.

(56) References Cited

FOREIGN PATENT DOCUMENTS

WO WO-2011088836 A1 7/2011
WO WO-2011088838 A1 7/2011

OTHER PUBLICATIONS

Apr. 26, 2022 International Search Report issued in International Patent Application No. PCT/CN2022/075094.
Apr. 26, 2022 Written Opinion of the International Searching Authority issued in International Patent Application No. PCT/CN2022/075094.
Dec. 29, 2022 1st Chinese Office Action issued in Chinese Priority Application No. 202111153079.8.
Dec. 25, 2022 1st Chinese Search Report issued in Chinese Priority Application No. 202111153079.8.
May 20, 2023 2nd Chinese Office Action issued in Chinese Priority Application No. 202111153079.8.
Martel & McArthur, Front Pharmacol 2020, 11: 1003.
Frankel & Schwartz, Therapeutic Advances in Psychopharmacology 2017, 7(1): 29-41.
Sahli & Tarazi,Expert Opinion on Drug Discovery 2018, vol. 13, Issue 1, 103-110.
Blair, Drugs, 2020, 80(4), 417-423.
Fan & Tan et al., Nature Communications, 2020, 11, Article 1074.
Niels Krogsgaard-Larsen et al., “Novel aza-analogous ergoline derived scaffolds as potent serotonin 5-HT6 and dopamine D2 receptor ligands”, Journal of Medicinal Chemistry, May 30, 2014, 57, 5823-5828.

(Continued)

*Primary Examiner* — Charanjit Aulakh

(74) *Attorney, Agent, or Firm* — Harness, Dickey & Pierce, P.L.C.

(57) ABSTRACT

An aza-ergoline derivative and a preparation method therefor and an application thereof. The derivative has a structure as shown in formula (I). The aza-ergoline derivative has good affinity, agonistic activity or selectivity to a dopamine D2 receptor.

(I)

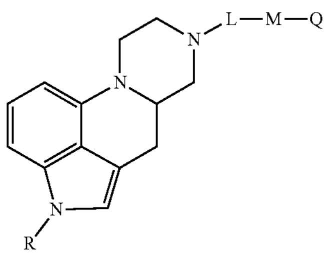

20 Claims, 1 Drawing Sheet

(56) References Cited

OTHER PUBLICATIONS

Niels Krogsgaard-Larsen et al., "Syntheses of aza-analogous isoergoline scaffolds using carbene mediated C—H insertion", Tetrahedron, Sep. 22, 2010, 66, 9297-9303.
Juza R., et al.; Recent advances in dopamine D2 receptor ligands in the treatment of neuropsychiatric disorders. Med Res Rev. Jan. 2023;43(1):55-211. doi: 10.1002/med.21923. Epub Sep. 16, 2022. PMID: 36111795.
Wexler TL., et al.; Dopamine agonists for the treatment of pituitary tumours: From ergot extracts to next generation therapies. Br J Clin Pharmacol. Apr. 2023; 89(4):1304-1317. doi: 10.1111/bcp.15660. Epub Jan. 30, 2023. PMID: 36630197.

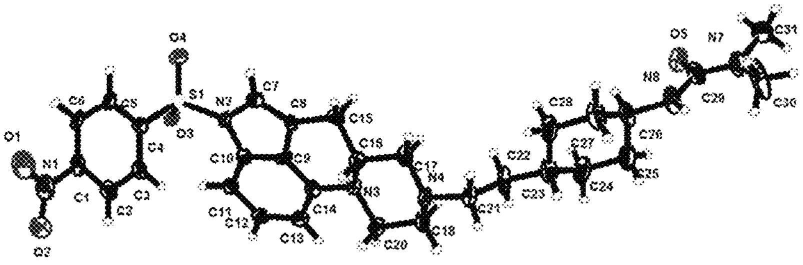

AZA-ERGOLINE DERIVATIVE AND PREPARATION METHOD THEREFOR AND APPLICATION THEREOF

CROSS-REFERENCE TO RELATED APPLICATIONS

The present application is a U.S. National Phase Application under 35 U.S.C. 371 of International Application No. PCT/CN2022/075094, filed on Jan. 29, 2022, which claims the priority of the Chinese patent application 2021101382499 with the filing date of Feb. 1, 2021, and the Chinese patent application 2021111530798 with the filing date of Sep. 29, 2021. The aforementioned Chinese patent applications are incorporated herein by reference in their entirety.

TECHNICAL FIELD

The disclosure relates to an aza-ergoline derivative, and a preparation method therefor and an application thereof.

BACKGROUND

The dopaminergic signaling pathway is related to various physiological functions such as human movement, behavior, emotion, and memory, and has been one of the focuses of neurobiological research in recent decades. Dysfunction of the dopaminergic signaling pathway is believed to be the cause of many diseases such as Parkinson's disease and schizophrenia. The dopaminergic signaling pathway consists of the neurotransmitter dopamine, dopamine receptors, and downstream signaling molecules associated with dopamine receptors. Dopamine receptors belong to the G protein-coupled receptor (GPCR) superfamily and are one of the most important central nervous system (CNS) drug targets. There are five subtypes of dopamine receptors ($D_{1-5}$), among which $D_1$ and $D_5$ are type $D_1$ receptors, which are mainly coupled with $G_s$ protein, and increase the level of intracellular cAMP after activation; $D_2$, $D_3$, and $D_4$ are type $D_2$ receptors, which are mainly coupled with $G_i$ protein, and reduce the level of intracellular cAMP after activation. Different dopamine receptors have different expression levels and distributions in the central nervous system, and play different physiological functions (Martel and McArthur, Front Pharmacol 2020, 11: 1003).

Among the five subtypes of dopamine receptors, $D_2$ receptors are most widely and deeply studied. Drugs in clinical use, such as Pramipexole, Ropinirole, and Rotigotine, are mainly used for the treatment of Parkinson's disease and restless legs syndrome. These drugs play a therapeutic role mainly by activating dopamine $D_2$ receptors, but they also have activity on other dopamine receptors such as $D_3$. Antischizophrenia drugs such as haloperidol and olanzapine mainly exert their therapeutic effects by antagonizing $D_2$ receptors, while the latest generation of drugs such as aripiprazole and cariprazine are partial agonists of dopamine $D_2$ receptors (Frankel and Schwartz, The Adv Psychopharmacol 2017, 7(1): 29-41).

Dopamine $D_2$ receptors share a certain degree of structural homology with other dopamine receptors and other monoamine GPCRs such as 5-hydroxytryptamine (5-HT) receptors. This homology leads to the fact that most drugs do not have target selectivity. Most of the above-mentioned antischizophrenia drugs targeting dopamine $D_2$ receptors have a certain degree of affinity for 5-HT receptors such as $5\text{-HT}_{2A}$ receptors, and the affinity of some drugs for $5\text{-HT}_{2A}$ receptor is even stronger than that for $D_2$ receptors. The dual action for $D_2$ receptors and $5\text{-HT}_{2A}$ receptors is a common feature of these drugs. Pimavanserin, which was approved by the US FDA in 2018, is a selective inverse agonist of $5\text{-HT}_{2A}$ receptors (Sahli and Tarazi, Expert Opin Drug Discov 2018, 13(1): 103-110); Lumateperone, which was approved by the US FDA in 2019, has an affinity for $5\text{-HT}_{2A}$ receptors that is about 60 times higher than that for $D_2$ receptors (Blair, Drugs, 2020, 80(4), 417-423). However, drugs with high selectivity for $D_2$ receptors have rarely been reported in the literature (Fan and Tan et al., Nat Comm, 2020, 11, 1074).

Krogsgaard-Larsen et al. reported a compound A with aza-ergoline skeleton, and its derivative A1 has the binding activity for $5\text{-HT}_{2A}$ receptors, and its derivative A2 has the agonistic activity for dopamine $D_2$ receptors, A3 has partial agonistic activity for dopamine $D_2$ receptors (Krogsgaard-Larsen et al., J. Med. Chem. 2014, 57, 5823-5828; WO 2011088836; WO 2011088838). The target selectivity, in vivo activity in animals and other druggability of these compounds have not been reported.

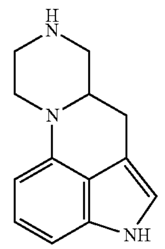

A

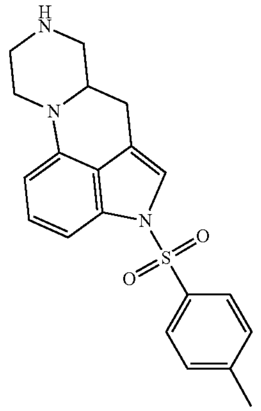

A1

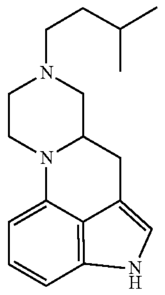

A2

-continued

A3

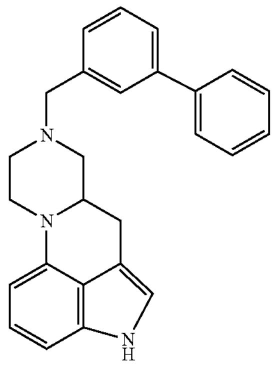

CONTENT OF THE PRESENT INVENTION

The technical problem to be solved by the present invention is that the existing compounds with affinity, agonistic activity or selectivity for dopamine $D_2$ receptors are few, so the present disclosure provides an aza-ergoline derivative and a preparation method therefor and an application thereof. The compounds of the present invention have good affinity, agonistic activity or selectivity for dopamine $D_2$ receptors.

The present invention provides a compound as shown in formula I, a pharmaceutically acceptable salt thereof, a solvate thereof or a solvate of a pharmaceutically acceptable salt thereof:

(I)

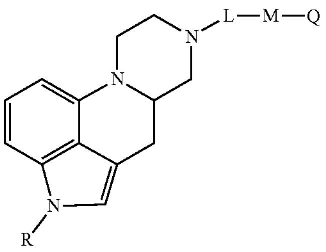

wherein, L is $C_{1-10}$ alkylene, $C_{2-10}$ alkenylene, $C_{2-10}$ alkynylene or —$C_{1-6}$ alkylene-$C_{3-6}$ cycloalkylene-;

M is —O—, —NH—, —$CH_2$—, —(CH—OH)— or —C(═O)—;

Q is $C_{6-18}$ aryl, $C_{6-18}$ aryl substituted with one or more $Q^{1-1}$, 5 to 10 membered heteroaryl, 5 to membered heteroaryl substituted with one or more $Q^{1-2}$, —C(═O)$R^1$ or —S(═O)$_2R^2$; the heteroatoms in the 5 to 10 membered heteroaryl are one or more of N, S or O, and the number is 1, 2 or 3; the heteroatoms in the 5 to 10 membered heteroaryl substituted with one or more $Q^{1-2}$ are one or more of N, S or O, and the number is 1, 2 or 3;

$Q^{1-1}$ is independently halogen or $C_{1-4}$ alkyl;

$Q^{1-2}$ is independently $C_{1-4}$ alkyl, oxo or hydroxyl;

$R^1$ and $R^2$ are independently —$NR^{1-1}R^{1-2}$, 3 to 6 membered heterocycloalkyl, $C_{6-18}$ aryl, $C_{6-18}$ aryl substituted with one or more $R^{1-3}$, 5 to 10 membered heteroaryl or 5 to 10 membered heteroaryl substituted with one or more $R^{1-4}$; the heteroatoms in the 3 to 6 membered heterocycloalkyl are one or more of N, S or O, and the number is 1, 2 or 3; the heteroatoms in the 5 to 10 membered heteroaryl are one or more of N, S or O, and the number is 1, 2 or 3; the heteroatoms in the 5 to 10 membered heteroaryl substituted with one or more $R^{1-4}$ are one or more of N, S or O, and the number is 1, 2 or 3;

$R^{1-1}$, $R^{1-2}$, $R^{1-3}$ and $R^{1-4}$ are independently $C_{1-4}$ alkyl;

R is hydrogen or $C_{1-4}$ alkyl.

In a preferred embodiment, in the compound as shown in formula I, the pharmaceutically acceptable salt thereof, the solvate thereof or the solvate of a pharmaceutically acceptable salt thereof, some groups can be defined as follows, and the remaining groups are defined as described in any embodiment of the present invention, hereinafter referred to as "in a preferred embodiment".

In a preferred embodiment, the compound as shown in formula I is a compound as shown in formula Ia, Ib or Ic:

Ia

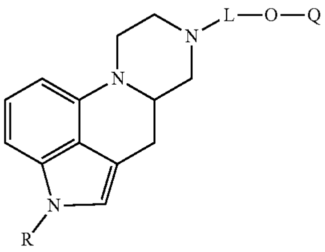

Ib

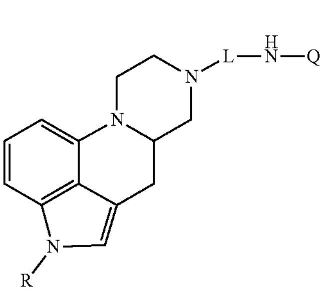

Ic

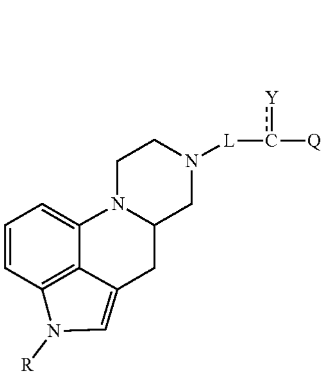

in formula Ic, " " represents a double bond or a single bond; Y is hydrogen, hydroxyl or oxygen.

In a preferred embodiment, the compound as shown in formula I is a compound as shown in formula Id and/or Ie, preferably a compound as shown in formula Id;

Id

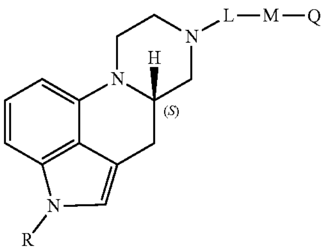

Ie

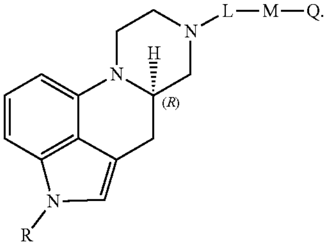

In a preferred embodiment, when the compound as shown in formula I has only one chiral center in

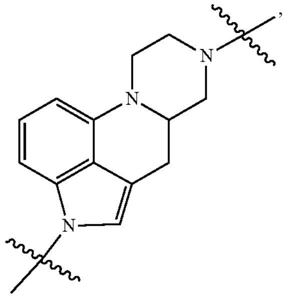

I

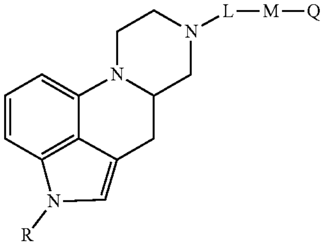

is (+)-I

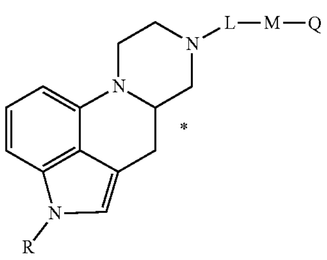

and/or

-continued (-)-I

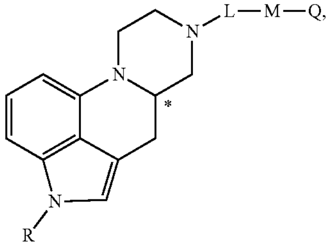

preferably (-)-I

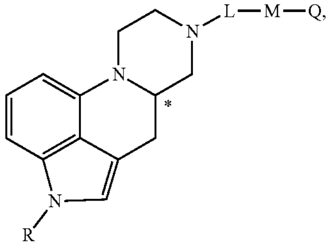

wherein the carbon atom marked with "*" is a chiral carbon atom; (+) represents a dextrorotatory compound, and (−) represents a levorotatory compound.

In a preferred embodiment,

L is $C_{1-10}$ alkylene, $C_{2-10}$ alkenylene or —$C_{1-6}$ alkylene-$C_{3-6}$ cycloalkylene-;

when M is —(CH—OH)— or —C(=O)—, R is hydrogen.

In a preferred embodiment,

L is $C_{1-10}$ alkylene or —$C_{1-6}$ alkylene-$C_{3-6}$ cycloalkylene-;

M is —O—, —NH— or —$CH_2$—;

Q is $C_{6-18}$ aryl, 5 to 10 membered heteroaryl, 5 to 10 membered heteroaryl substituted with one or more $Q^{1-2}$, —C(=O)$R^1$ or —S(=O)$_2R^2$.

In a preferred embodiment,

L is $C_{1-10}$ alkylene or —$C_{1-6}$ alkylene-$C_{3-6}$ cycloalkylene-;

M is —O—, —NH— or —$CH_2$—;

Q is $C_{6-18}$ aryl, 5 to 10 membered heteroaryl, 5 to 10 membered heteroaryl substituted with one or more $Q^{1-2}$, —C(=O)$R^1$ or —S(=O)$_2R^2$;

when M is —O—, $Q^{1-2}$ is $C_{1-4}$alkyl or hydroxyl;

when the heteroatom in the 5 to 10 membered heteroaryl is O, the number of heteroatoms in the 5 to 10 membered heteroaryl is 1.

In a preferred embodiment,

L is $C_{1-10}$ alkylene or —$C_{1-6}$ alkylene-$C_{3-6}$ cycloalkylene-;

M is —O—, —NH— or —$CH_2$—;

Q is $C_{6-18}$ aryl, 5 to 10 membered heteroaryl, 5 to 10 membered heteroaryl substituted with one or more $Q^{1-2}$, —C(=O)$R^1$ or —S(=O)$_2R^2$;

when L is —$C_{1-6}$ alkylene-$C_{3-6}$ cycloalkylene-, the $C_{1-6}$ alkylene in the —$C_{1-6}$ alkylene-$C_{3-6}$ cycloalkylene- is ethylene.

In a preferred embodiment,

L is $C_{1-10}$ alkylene or —$C_{1-6}$ alkylene-$C_{3-6}$ cycloalkylene-;

M is —O— or —NH—;

Q is —C(═O)$R^1$ or 5 to 10 membered heteroaryl substituted with one or more $Q^{1-2}$;

$R^1$ is $NR^{1-1}R^{1-2}$.

In a preferred embodiment, L is $C_{1-10}$ alkylene;

M is —O—;

Q is a 5 to 10 membered heteroaryl substituted with one or more $Q^{1-2}$.

In a preferred embodiment, L is —$C_{1-6}$ alkylene —$C_{3-6}$ cycloalkylene-;

M is —NH—;

Q is —C(═O)$R^1$;

$R^1$ is $NR^{1-1}R^{1-2}$.

In a preferred embodiment, the molecular structure as shown in formula I is as shown in formula Ia:

Ia

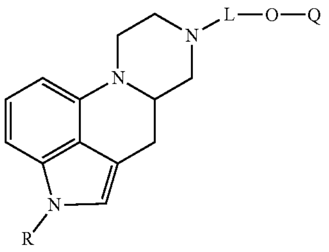

L is $C_{1-10}$ alkylene or $C_{2-10}$ alkenylene;

Q is 5 to 10 membered heteroaryl, or 5 to 10 membered heteroaryl substituted with one or more $Q^{1-2}$.

In a preferred embodiment, the molecular structure as shown in formula I is as shown in formula Ia:

Ia

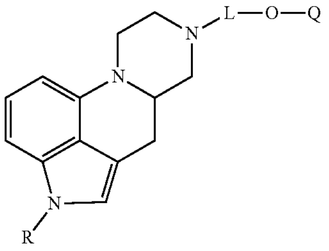

L is $C_{1-10}$ alkylene or $C_{2-10}$ alkenylene;

Q is $C_{6-18}$ aryl substituted with one or more $Q^{1-1}$, 5 to 10 membered heteroaryl or 5 to 10 membered heteroaryl substituted with one or more $Q^{1-2}$;

$Q^{1-1}$ is halogen.

In a preferred embodiment, the molecular structure as shown in formula I is as shown in formula Ib:

Ib

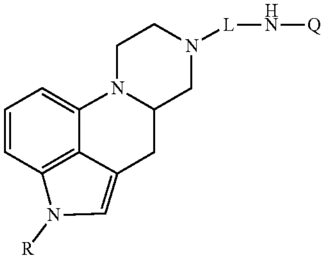

L is —$C_{1-6}$ alkylene-$C_{3-6}$ cycloalkylene-;

Q is —C(═O)$R^1$ or —S(═O)$_2R^2$;

$R^1$ and $R^2$ are independently 3 to 6 membered heterocycloalkyl, $C_{6-18}$ aryl or 5 to 10 membered heteroaryl.

In a preferred embodiment, the molecular structure as shown in formula I is as shown in formula Ic:

Ic

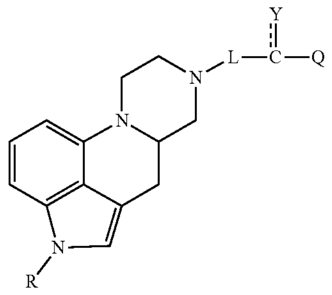

"---" represents a double bond or a single bond;

Y is hydrogen, hydroxyl or oxygen;

L is $C_{1-10}$ alkylene;

Q is $C_{6-18}$ aryl substituted with one or more $Q^{1-1}$ or 5 to 10 membered heteroaryl substituted with one or more $Q^{1-2}$;

$Q^{1-1}$ is halogen;

$Q^{1-2}$ is independently $C_{1-4}$ alkyl or oxo.

In a preferred embodiment, the molecular structure as shown in formula I is as shown in formula Ic-1:

Ic-1

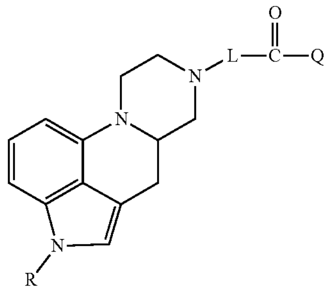

L is $C_{1-10}$ alkylene;

Q is $C_{6-18}$ aryl substituted with one or more $Q^{1-1}$;

$Q^{1-1}$ is halogen;

R is hydrogen.

In a preferred embodiment, the molecular structure as shown in formula I is as shown in formula Ic-2:

Ic-2

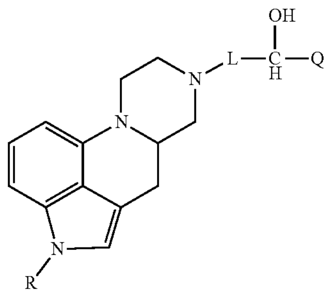

L is $C_{1-10}$ alkylene;

Q is $C_{6-18}$ aryl substituted with one or more $Q^{1-1}$;

$Q^{1-1}$ is halogen;

R is hydrogen.

In a preferred embodiment, the molecular structure as shown in formula I is as shown in formula Ic-3:

Ic-3

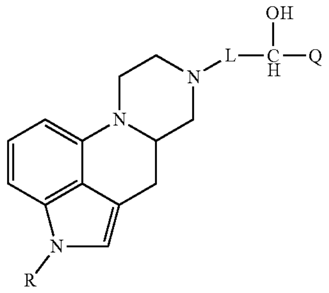

L is $C_{1-10}$ alkylene;

Q is a 5 to 10 membered heteroaryl substituted with one or more $Q^{1-2}$;

$Q^{1-1}$ is $C_{1-4}$ alkyl or oxo;

R is hydrogen.

In a preferred embodiment, when L is $C_{1-10}$ alkylene, the $C_{1-10}$ alkylene is $C_{1-4}$ alkylene (e.g. methylene, ethylene (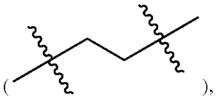 [SMILES: *CC*]), n-propylene (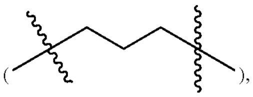 [SMILES: *CCC*]), isopropylene (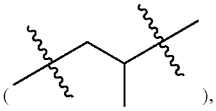 [SMILES: *CC(*)C]), n-butylene (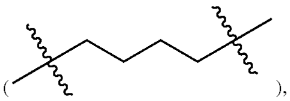 [SMILES: *CCCC*]), isobutylene (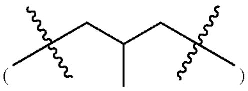 [SMILES: *CC(C)C*])

or tert-butylene (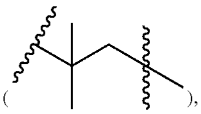), preferably n-propylene or n-butylene, more preferably n-butylene.

In a preferred embodiment, when L is $C_{2-10}$ alkenylene and the $C_{2-10}$ alkenylene is $C_{2-4}$ alkenylene, it is preferably

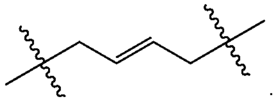 [SMILES: *C/C=C/C*].

In a preferred embodiment, when L is —$C_{1-6}$ alkylene-$C_{3-6}$ cycloalkylene-, the $C_{1-6}$ alkylene is connected to N, and the $C_{3-6}$ cycloalkylene is connected to Q.

In a preferred embodiment, when L is —$C_{1-6}$ alkylene-$C_{3-6}$ cycloalkylene-, the $C_{1-6}$ alkylene in the —$C_{1-6}$ alkylene-$C_{3-6}$ cycloalkylene is methylene, ethylene (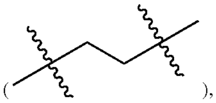 [SMILES: *CC*]), n-propylene (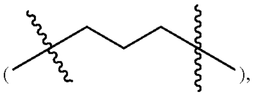), isopropylene (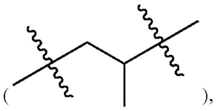 [SMILES: *CC(*)C]), n-butylene (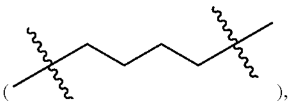 [SMILES: *CCCC*]), isobutylene (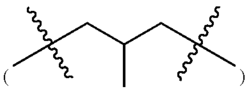 [SMILES: *CC(C)C*])

or tert-butylene (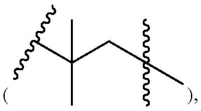), preferably methylene or ethylene, more preferably ethylene.

In a preferred embodiment, when L is —$C_{1-6}$ alkylene-$C_{3-6}$ cycloalkylene-, the $C_{3-6}$ cycloalkylene in the —$C_{1-6}$ alkylene-$C_{3-6}$ cycloalkylene is cyclopropylene, cyclobutylene, cyclopentylene or cyclohexylene (e.g., 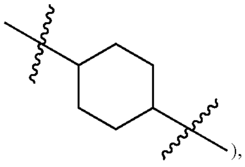), preferably

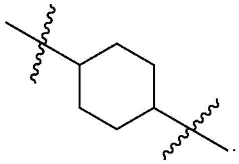 [SMILES: *C1CCC(*)CC1].

In a preferred embodiment, when L is —$C_{1-6}$ alkylene-$C_{3-6}$ cycloalkylene-, the —$C_{1-6}$ alkylene-$C_{3-6}$ cycloalkylene- is

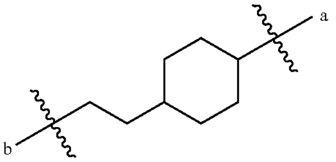

(e.g., 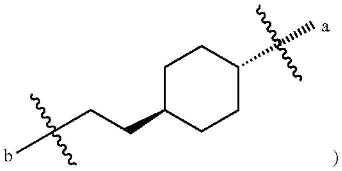) or

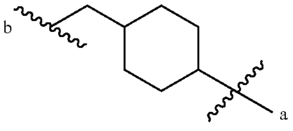

-continued (e.g., 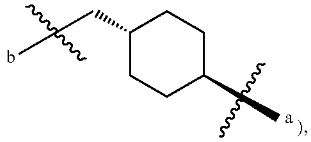), wherein the a-terminal is connected to Q, and the b-terminal is connected to N, preferably

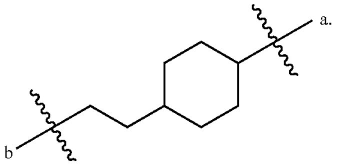 [SMILES: *CCC1CCC(*)CC1].

In a preferred embodiment, when Q is $C_{6-18}$ aryl, the $C_{6-18}$ aryl is $C_{6-14}$ aryl (e.g., phenyl, naphthyl, anthracenyl or phenanthryl), further can be phenyl.

In a preferred embodiment, when Q is $C_{6-18}$ aryl substituted with $Q^{1-1}$, the $C_{6-18}$ aryl is $C_{6-14}$ aryl (e.g., phenyl, naphthyl, anthracenyl or phenanthryl), further can be phenyl.

In a preferred embodiment, when Q is $C_{6-18}$ aryl substituted with $Q^{1-1}$, the number of $Q^{1-1}$ is 1 or 2. When there are more than one $Q^{1-1}$, $Q^{1-1}$ can be the same or different, for example, can be different.

In a preferred embodiment, when $Q^{1-1}$ is halogen, the halogen is F, Cl, Br or I, preferably F.

In a preferred embodiment, when Q is $C_{6-18}$ aryl substituted with $Q^{1-1}$, the $C_{6-18}$ aryl substituted with $Q^{1-1}$ is

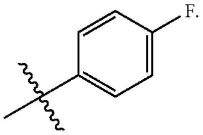 [SMILES: *c1ccc(F)cc1].

In a preferred embodiment, when Q is 5 to 10 membered heteroaryl, the 5 to 10 membered heteroaryl is 9 or 10 membered heteroaryl, and the number of heteroatoms is 1 or 2, more preferably

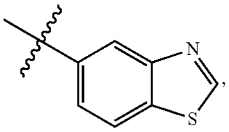,
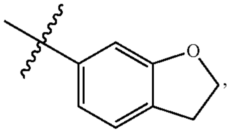,
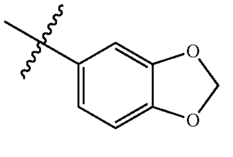
or
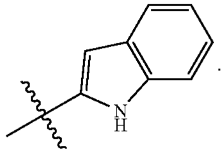.

In a preferred embodiment, when Q is 5 to 10 membered heteroaryl substituted with one or more $Q^{1-2}$, the 5 to 10 membered heteroaryl is 9 or 10 membered heteroaryl, the heteroatom is N and/or O, the number of heteroatoms is 1 or 2, preferably tetrahydroquinolyl ( 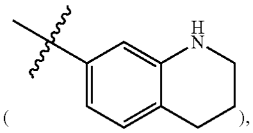 [SMILES: *c1ccc2c(c1)NCCC2] ), quinolinyl (e.g., 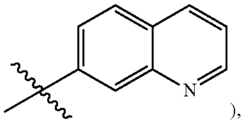 ), benzisoxazolyl (e.g., 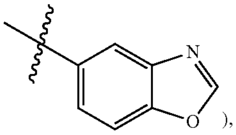 ), benzoxazolyl (e.g., 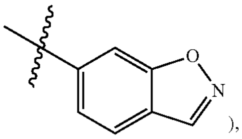 ), or tetrahydropyridopyrimidinyl (e.g., oxo- 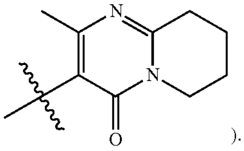 ).

In a preferred embodiment, when Q is $C_{6-18}$ aryl substituted with $Q^{1-2}$, the number of $Q^{1-2}$ is 1 or 2. When there are more than one $Q^{1-2}$, the $Q^{1-2}$ is the same or different, for example, is different.

In a preferred embodiment, when $Q^{1-2}$ is $C_{1-4}$ alkyl, the $C_{1-4}$ alkyl is methyl, ethyl, n-propyl, isopropyl, n-butyl, isobutyl or tert-butyl, preferably methyl.

In a preferred embodiment, when Q is 5 to 10 membered heteroaryl substituted with one or more $Q^{1-2}$, the 5 to 10 membered heteroaryl substituted with one or more $Q^{1-2}$ is

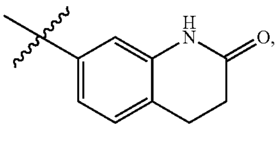

-continued

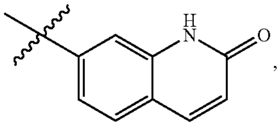 , 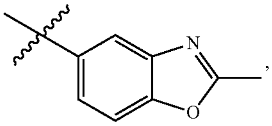 ,

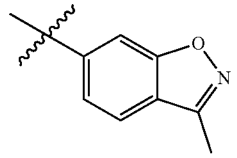 or 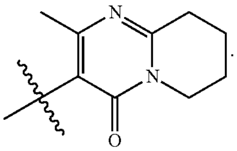 .

In a preferred embodiment, when $R^1$ and $R^2$ are independently 3 to 6 membered heterocycloalkyl, the 3 to 6 membered heterocycloalkyl is piperidinyl (e.g., 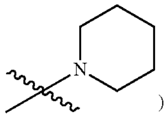 )

or pyrrolidinyl (e.g., 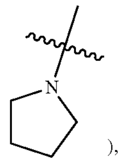 ), preferably pyrrolidinyl.

In a preferred embodiment, when $R^1$ is 3 to 6 membered heterocycloalkyl, the 3 to 6 membered heterocycloalkyl is connected to carbonyl through a heteroatom.

In a preferred embodiment, when $R^1$ and $R^2$ are independently $C_{6-18}$ aryl, the $C_{6-18}$ aryl is $C_{6-14}$ aryl (e.g., phenyl, naphthyl, anthracenyl or phenanthryl), and may be further phenyl.

In a preferred embodiment, when $R^1$ and $R^2$ are independently $C_{6-18}$ aryl substituted with one or more $R^{1-3}$, the $C_{6-18}$ aryl is $C_{6-14}$ aryl (e.g., phenyl, naphthyl, anthracenyl or phenanthryl), further can be phenyl.

In a preferred embodiment, when $R^1$ and $R^2$ are independently 5 to 10 membered heteroaryl, the 5 to 10 membered heteroaryl is 9 or 10 membered heteroaryl, the heteroatom is N, and the number of heteroatoms is 1 or 2, preferably indolyl (e.g., 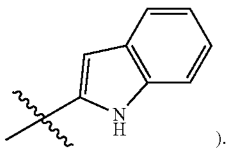 ).

In a preferred embodiment, when $R^{1-1}$, $R^{1-2}$, $R^{1-3}$ and $R^{1-4}$ is independently $C_{1-4}$ alkyl, the $C_{1-4}$ alkyl is methyl, ethyl, n-propyl, isopropyl, n-butyl, isobutyl, sec-butyl or tert-butyl, preferably methyl.

In a preferred embodiment, when R is $C_{1-4}$ alkyl, the $C_{1-4}$ alkyl is methyl, ethyl, n-propyl, isopropyl, n-butyl, isobutyl, sec-butyl or tert-butyl, preferably methyl.

In a preferred embodiment, L is $C_{1-10}$ alkylene, $C_{2-10}$ alkenylene or —$C_{1-6}$ alkylene-$C_{3-6}$ cycloalkylene.

In a preferred embodiment, L is $C_{1-10}$ alkylene or —$C_{1-6}$ alkylene-$C_{3-6}$ cycloalkylene.

In a preferred embodiment, M is —O—, —NH— or —$CH_2$—.

In a preferred embodiment, $Q^{1-1}$ is halogen.

In a preferred embodiment, $R^1$ is —$NR^{1-1}R^{1-2}$, 3 to 6 membered heterocycloalkyl, $C_{6-18}$ aryl or 5 to 10 membered heteroaryl, preferably —$NR^{1-1}R^{1-2}$, 3 to 6 membered heterocycloalkyl or $C_{6-18}$ aryl.

In a preferred embodiment, R is hydrogen.

In a preferred embodiment,

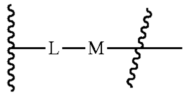

is

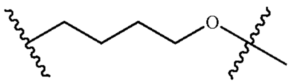
,
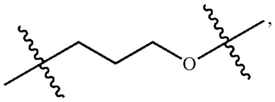
,
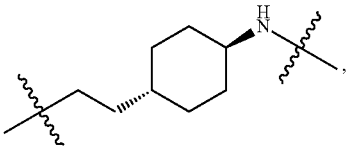
,
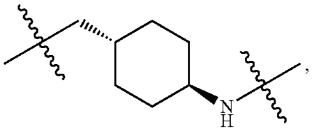
,
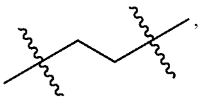
,
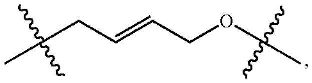
,
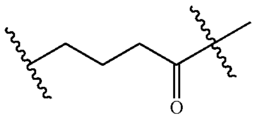
or
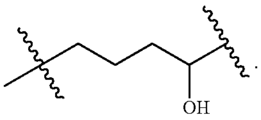
.

In a preferred embodiment, the compound as shown in formula I is optionally any of the following compounds:

I-1

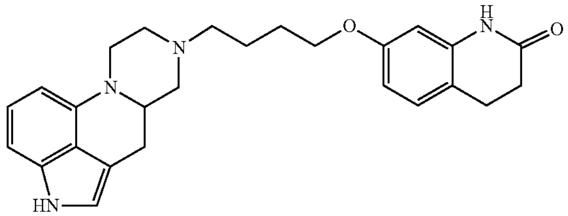

-continued

I-2

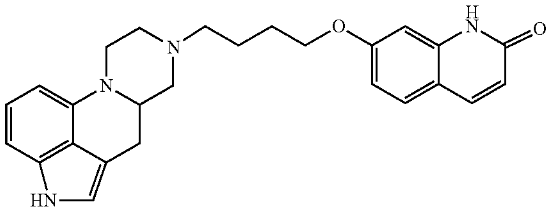

I-3

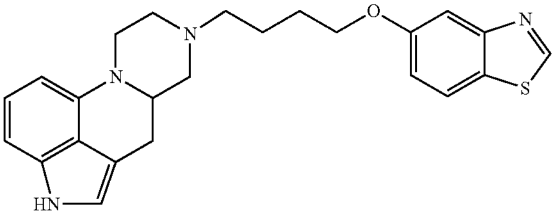

I-4

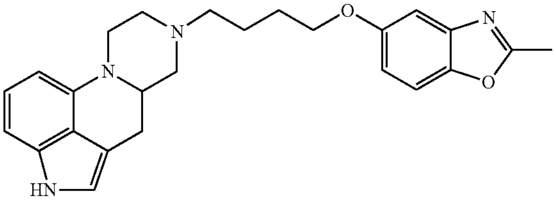

I-5

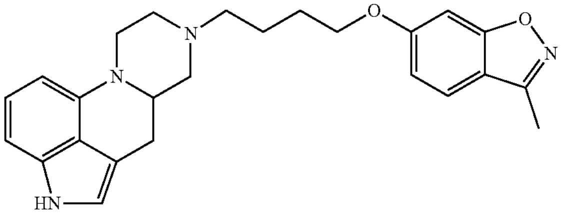

I-6

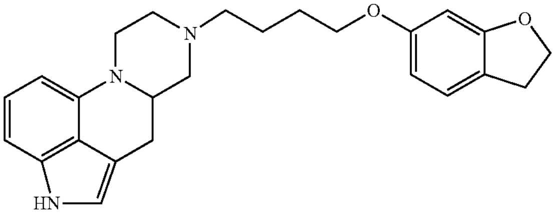

I-7

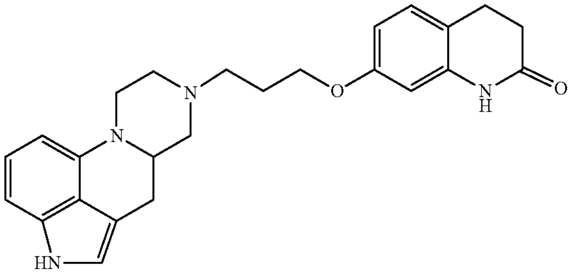

-continued
I-8
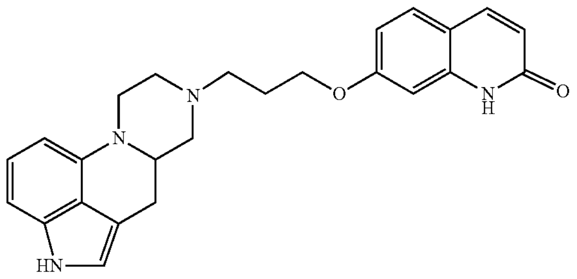
I-9
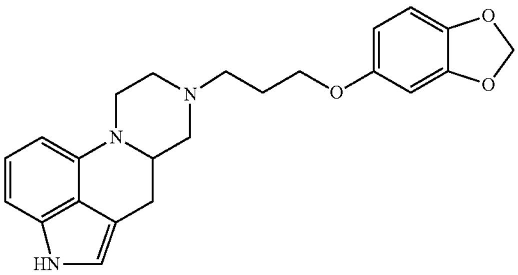
I-10
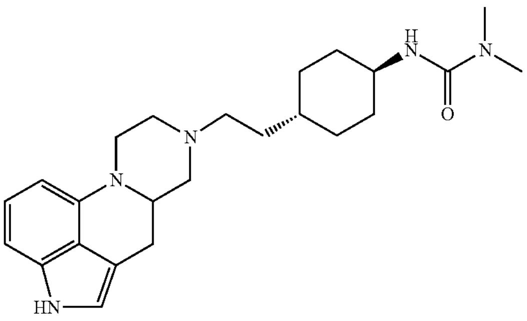
I-11
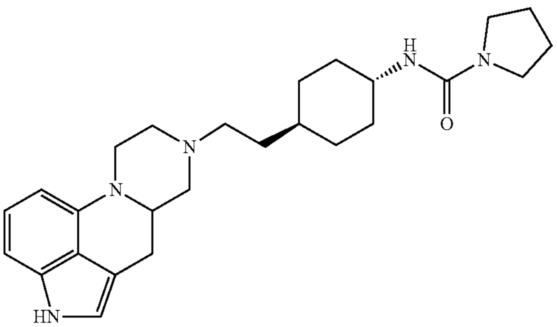
I-12
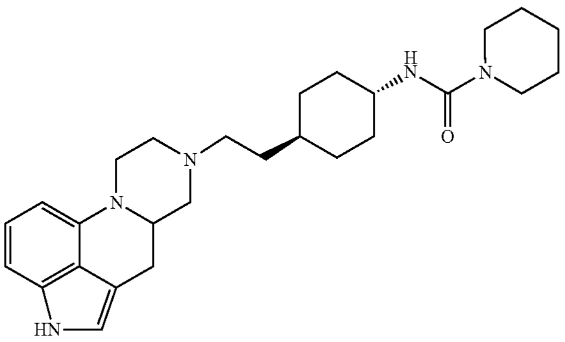
-continued
I-13
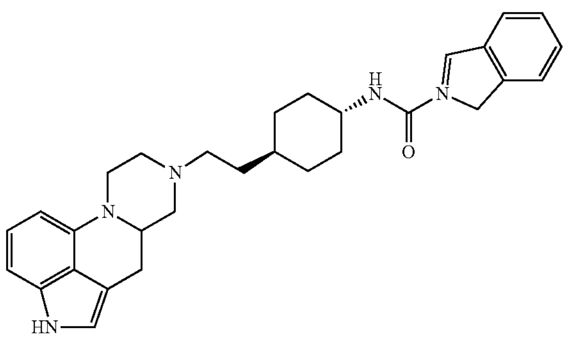
I-14
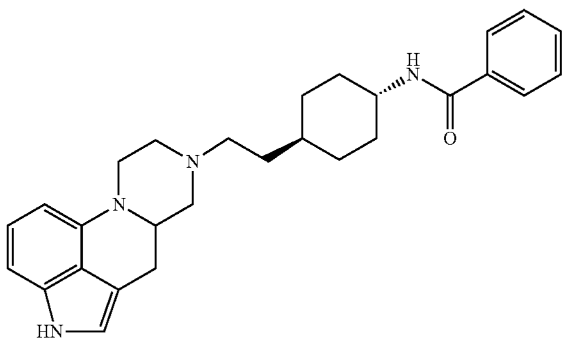
I-15
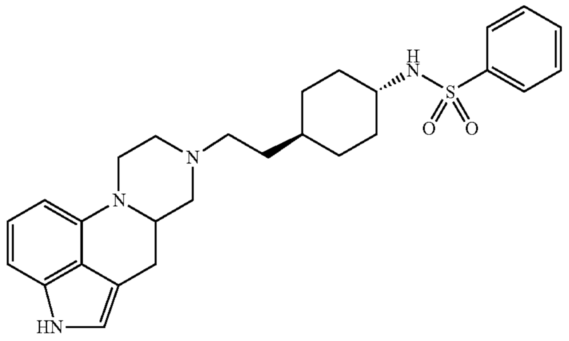
I-16
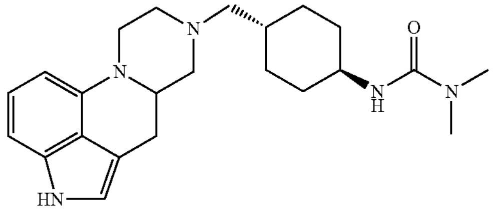
I-17
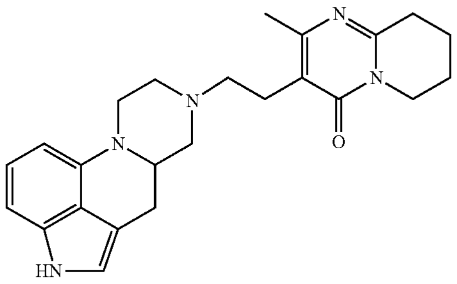

-continued
I-18
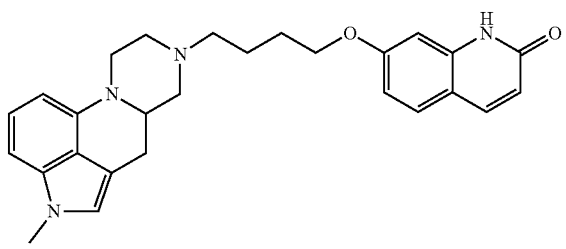
I-19
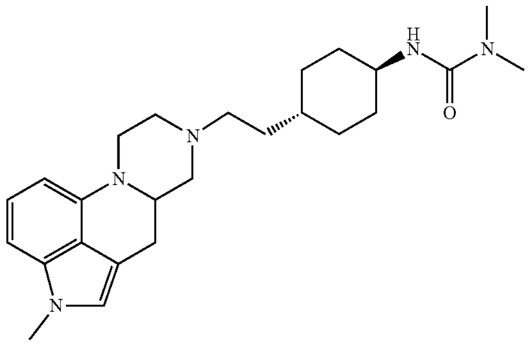
I-20
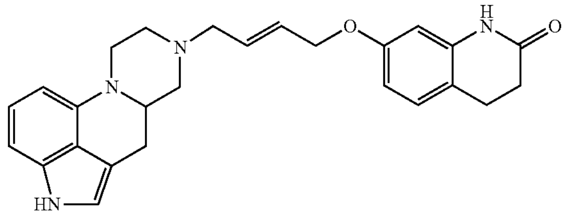
I-21
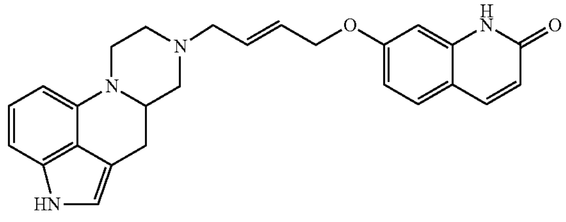
I-22
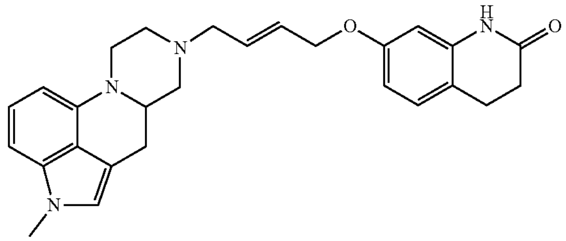
-continued
I-23
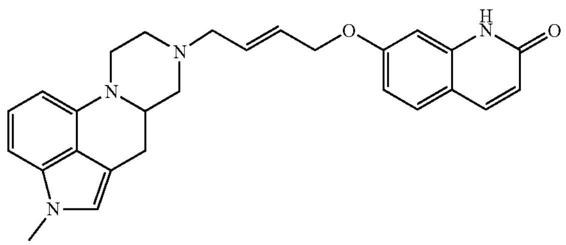
I-24
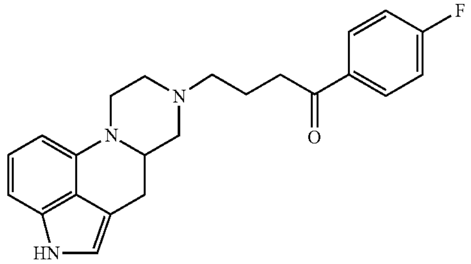
I-25
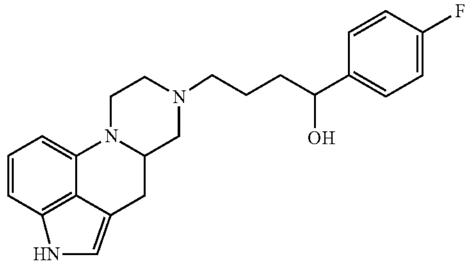
I-26
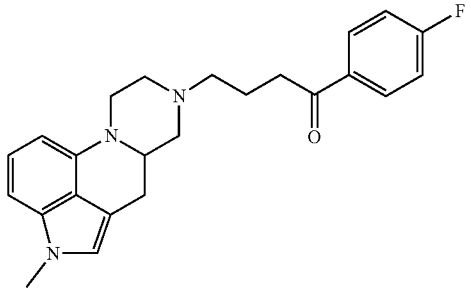
I-27
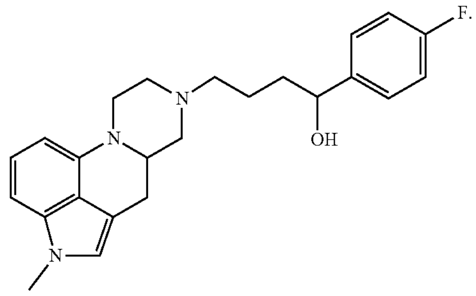
In a preferred embodiment, the compound as shown in formula I is optionally any of the following compounds:

(+)-(R)-I-10

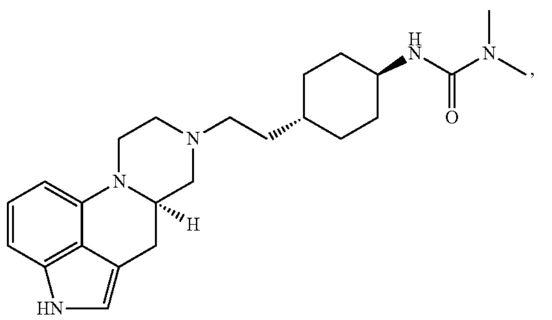

(-)-(S)-I-10

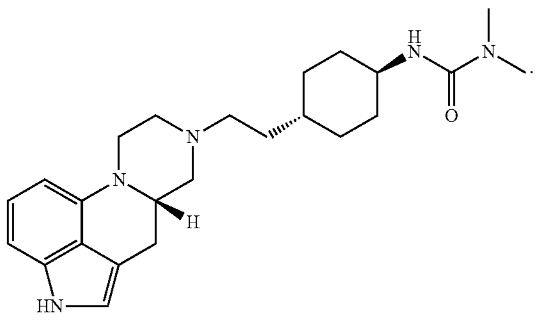

In a preferred embodiment, the compound as shown in formula I is optionally any of the following compounds:

I-2

“ 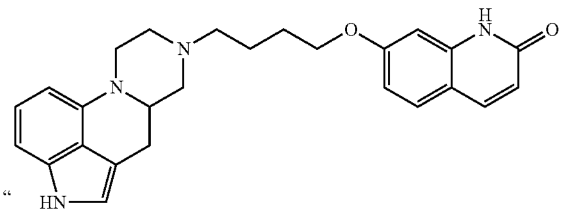

with optical rotation of +50.33° and/or retention time of 5.805 min under the following chiral preparation conditions” or

I-2

“ 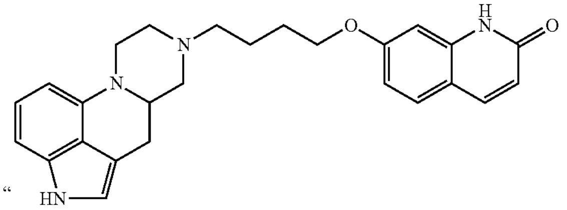

with optical rotation of −45.00° and/or retention time of 7.60 min under the following chiral preparation conditions”;

Chiral preparation conditions: chromatographic column: chiral column CHIRALCEL OD, column volume: 5.0 cm×25 cm, 10 μm filler; mobile phase: MeOH/diethylamine=100/0.1; flow rate: 30 mL/min; wavelength: UV 214 nm; temperature: 38° C.

In a preferred embodiment, the compound as shown in formula I is the following compound:

(-)-(S)-I-10

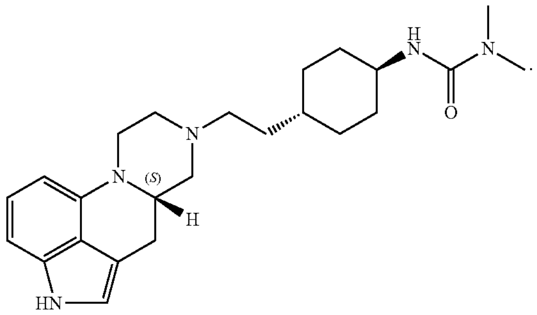

The present invention also provides a method for preparing the compound as shown in formula I, the pharmaceutically acceptable salt thereof, the solvate thereof or the solvate of a pharmaceutically acceptable salt thereof described above, the method comprises the following steps:

in the presence of a basic reagent, the compound as shown in formula II and the compound as shown in formula III are subjected to the following alkylation reaction in a solvent to obtain the compound as shown in formula I;

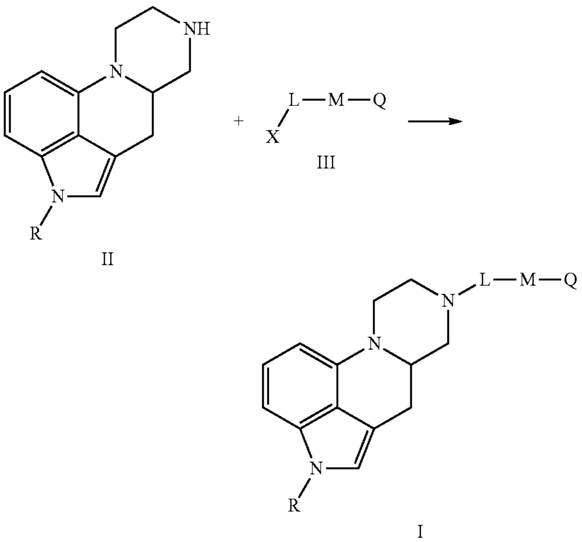

II

III

I wherein, X is a halogen; L, M, Q and R are as defined above.

The conditions and operations of the alkylation reaction can be conventional conditions and operations of such reactions in the art, and the following conditions are particularly preferred in the present disclosure:

the basic reagent is, for example, $K_2CO_3$ (for example, the molar ratio of the basic reagent to the compound of formula II is 6:1).

The solvent is, for example, tetrahydrofuran and dimethyl sulfoxide (for example, the volume ratio of the two is 3:1).

The temperature of the alkylation reaction is, for example, 60° C.

The present invention also provides a method for preparing the compound as shown in formula I, the pharmaceutically acceptable salt thereof, the solvate thereof or the solvate of a pharmaceutically acceptable salt thereof described above, the method comprises the following steps:

in the presence of a basic reagent, the compound as shown in formula II and the compound as shown in formula III in The present invention further provides a pharmaceutical composition, which comprises the compound as shown in formula I, the pharmaceutically acceptable salt thereof, the solvate thereof or the solvate of a pharmaceutically acceptable salt thereof described above, and a pharmaceutical adjuvant.

The present invention further provides the use of a substance A in the preparation of a dopamine $D_2$ receptor agonist, the substance A is the compound as shown in formula I, the pharmaceutically acceptable salt thereof, the solvate thereof or the solvate of a pharmaceutically acceptable salt thereof described above, or the pharmaceutical composition described above.

The present invention further provides the use of a substance A in the preparation of a drug for treating and/or preventing a disease related to dopamine $D_2$ receptors; the substance A is the compound as shown in formula I, the pharmaceutically acceptable salt thereof, the solvate thereof or the solvate of a pharmaceutically acceptable salt thereof described above, or the pharmaceutical composition described above.

The disease related to dopamine $D_2$ receptors refers to one or more of a neurodegenerative disease, a mental disorder, and a metabolic disease related to a mental disorder, such as Parkinson's disease, Alzheimer's disease, dementia, schizophrenia, bipolar disorder, depression, hyperactivity, restless legs syndrome, Huntington's disease, male erectile dysfunction, prolactinoma, or drug addiction.

The present disclosure further provides the use of a substance A in the preparation of a drug for treating and/or preventing a diseases M; the substance A is the compound as shown in formula I, the pharmaceutically acceptable salt thereof, the solvate thereof or the solvate of a pharmaceutically acceptable salt thereof described above, or the pharmaceutical composition described above; the disease M is one or more of a neurodegenerative disease, a mental disorder, and a metabolic disease related to a mental disorder.

In the use, the disease M is preferably Parkinson's disease, Alzheimer's disease or dementia, schizophrenia, bipolar disorder, depression, hyperactivity, restless leg syndrome, Huntington's disease, male erectile dysfunction, prolactinoma, or drug addiction.

The present invention further provides a method for preventing or treating a disease related to dopamine $D_2$ receptors, and the method comprises administering a therapeutically effective amount of substance A to a subject. The substance A is the compound as shown in formula I, the pharmaceutically acceptable salt thereof, the solvate thereof or the solvate of a pharmaceutically acceptable salt thereof described above, or the pharmaceutical composition described above.

The disease related to dopamine $D_2$ receptors refers to one or more of a neurodegenerative disease, a mental disorder, and a metabolic disease related to a mental disorder, such as Parkinson's disease, Alzheimer's disease, dementia, schizophrenia, bipolar disorder, depression, hyperactivity, restless legs syndrome, Huntington's disease, male erectile dysfunction, prolactinoma, or drug addiction.

The present invention further provides a method for preventing or treating disease M, and the method comprises administering a therapeutically effective amount of substance A to a subject. The substance A is the compound as shown in formula I, the pharmaceutically acceptable salt thereof, the solvate thereof or the solvate of a pharmaceutically acceptable salt thereof described above, or the pharmaceutical composition described above; the disease M is one or more of a neurodegenerative disease, a mental disorder, and a metabolic disease related to a mental disorder.

In the method, the disease M is preferably Parkinson's disease, Alzheimer's disease or dementia, schizophrenia, bipolar disorder, depression, hyperactivity, restless legs syndrome, Huntington's disease, male erectile dysfunction, prolactinoma, or drug addiction.

The present invention further provides a crystal as shown in the formula pNs-(+)-I-10, the crystal system of which belongs to the triclinic crystal system, the P1 space group, and the unit cell parameters are a=9.315 Å, b=6.564 Å, c=23.792 Å, α=90.15°, β=99.368°, γ=90.25°;

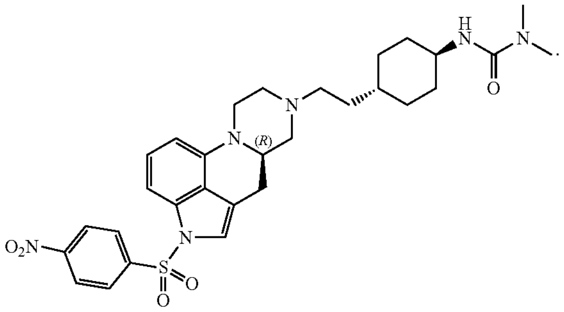

Unless otherwise specified, terms used in the present invention have the following meanings:

As used herein, a substituent employed may be preceded by a single dash "-" to indicate that the named substituent is connected to the parent moiety by a single bond. In addition, a substituent is described by conventional chemical formulas written "left to right" or "top to bottom", for example, "—$C_{1-6}$ alkylene-$C_{3-6}$ cycloalkylene" means that $C_{1-6}$ alkylene is connected to N in the parent moiety through a single bond.

The terms "compound" and "pharmaceutically acceptable salt", if tautomers exist, may exist as a single tautomer or as a mixture of tautomers, preferably in the form in which a relatively stable tautomer is dominant.

The term "halogen" refers to fluorine, chlorine, bromine or iodine.

The term "alkyl" refers to straight or branched alkyl having specified number of carbon atoms (e.g., $C_1$ to $C_{10}$). Alkyl includes but are not limited to methyl, ethyl, n-propyl, isopropyl, n-butyl, tert-butyl, isobutyl, sec-butyl, n-pentyl, n-hexyl, n-heptyl, n-octyl, etc.

The term "alkylene" refers to a divalent group of a straight or branched saturated aliphatic hydrocarbon group having specified number of carbon atoms. Two valences can be on the same atom, such as methylene (—$CH_2$—), ethylene

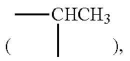

and two valences can also be connected to two atoms respectively, such as 1,2-ethylene (—$CH_2CH_2$—).

The term "alkenylene" refers to a divalent group of a straight or branched aliphatic hydrocarbon group containing one or more double bonds and specified number of carbon atoms (e.g., $C_2$ to $C_{10}$). Two valences can be on the same atom, such as

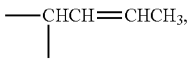

and two valences can also be connected to two atoms respectively, such as $—CH_2CH{=}CHCH_2—$.

The term "alkynylene" refers to a divalent group of a straight or branched aliphatic hydrocarbon group containing one or more triple bonds and specified number of carbon atoms (e.g., $C_2$ to $C_{10}$). Two valences can be on the same atom, such as

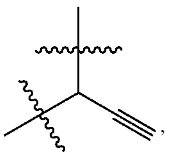 [SMILES: *C(*)C#C]

and two valences can also be connected to two atoms respectively, such as

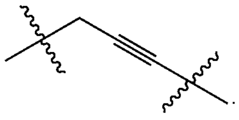 [SMILES: *C#CC*]

The term "cycloalkyl" refers to a saturated monocyclic cyclic group consisting only of carbon atoms and having specified number of carbon atoms (e.g., $C_3$ to $C_6$). Cycloalkyl includes, but is not limited to, cyclopropyl, cyclobutyl, cyclopentyl, cyclohexyl, etc.

The term "cycloalkylene" refers to a divalent group of saturated cyclic alkylene, for example: cyclopropylene (e.g., 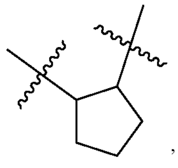 , 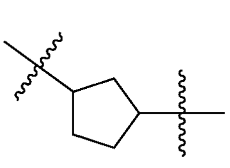 or cyclohexylene, etc.).

The term "heterocycloalkyl" refers to a cyclic group with specified number of ring atoms (for example, 5 to 10 membered), specified number of heteroatoms (for example, 1, 2 or 3) and specified type of heteroatoms (one or more of N, O and S), which is a single ring, a bridged ring or a spiro ring, and each ring is saturated. Heterocycloalkyl includes, but is not limited to, azetidinyl, tetrahydropyrrolyl, tetrahydrofuranyl, morpholinyl, piperidinyl, etc.

The term "aryl" refers to a cyclic group consisting only of carbon atoms and having specified number of carbon atoms (for example, $C_6$ to $C_{10}$), which is a monocyclic ring or a polycyclic ring, and at least one ring is aromatic (according to Huckel's rule). The aryl is connected to other segments in the molecule through an aromatic ring or a non-aromatic ring. Aryl includes, but are not limited to, phenyl, naphthyl, etc.

The term "heteroaryl" refers to a cyclic group with specified number of ring atoms (for example, 5 to 10 membered), specified number of heteroatoms (for example, 1, 2 or 3) and specified type of heteroatoms (one or more of N, O and S), which is a monocyclic ring or a polycyclic ring, and at least one ring is aromatic (according to Huckel's rule). The heteroaryl is connected to other segments in the molecule through an aromatic ring or a non-aromatic ring. Heteroaryl includes, but are not limited to, furyl, pyrrolyl, thienyl, pyrazolyl, imidazolyl, oxazolyl, thiazolyl, pyridyl, pyrimidinyl, indolyl, etc. Heteroaryl is also for example

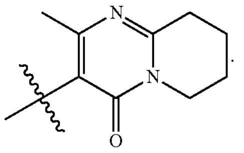 [SMILES: *c1c(C)nc2n(c1=O)CCCC2]

"-" at the end of a group means that the group is connected to other segments in the molecule through this site. For example, $CH_3—C({=}O)—$ refers to acetyl.

" 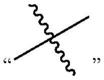 "

in a structural segment means that the structural segment is connected to other segments in the molecule through this site. For example,

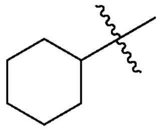 [SMILES: *C1CCCCC1]

refers to cyclohexyl.

The term "more" refers to 2, 3, 4 or 5.

When any variable (such as the group $R^{1-1}$) appears multiple times in the definition of a compound, their definitions are independent from each other and do not interfere with each other. For example, $C_6$-$C_{10}$ aryl substituted with 3 $R^{1-1}$ means that $C_6$-$C_{10}$ aryl would be substituted with 3 $R^{1-1}$, and the definitions of the 3 $R^{1-1}$ are independent from each other and do not interfere with each other.

The term "pharmaceutically acceptable salt" refers to a salt obtained by reacting a compound with a pharmaceutically acceptable (relatively non-toxic, safe, and suitable for use by patients) acid or base. When a compound contains relatively acidic functional groups, base addition salts can be obtained by contacting the free form of the compound with a sufficient amount of a pharmaceutically acceptable base in a suitable inert solvent. Pharmaceutically acceptable base addition salts include, but are not limited to, sodium salts, potassium salts, calcium salts, aluminum salts, magnesium salts, bismuth salts, ammonium salts, etc. When the compound contains relatively basic functional groups, acid addition salts can be obtained by contacting the free form of the compound with a sufficient amount of a pharmaceutically acceptable acid in a suitable inert solvent. Pharmaceutically acceptable acid addition salts include, but are not limited to, hydrochlorides, sulfates, methanesulfonates, etc. For details, see Handbook of Pharmaceutical Salts: Properties, Selection, and Use (P. Heinrich Stahl, 2002).

The term "solvate" refers to a substance formed after crystallization of a compound with a solvent (including but not limited to: water, methanol, ethanol, etc.). Solvates are divided into stoichiometric solvates and non-stoichiometric solvates.

The term "solvate of a pharmaceutically acceptable salt" refers to a substance formed by conjugating a compound with a pharmaceutically acceptable (relatively non-toxic, safe and suitable for use by patients) acid or base and a solvent (including but not limited to: water, methanol, ethanol, etc.). In the term, the pharmaceutically acceptable salt has the same meaning as the term "pharmaceutically acceptable salt" described above, and the solvent is stoichiometric or non-stoichiometric. The solvate of a pharmaceutically acceptable salt includes, but not limited to, hydrochloride monohydrate.

The term "pharmaceutical adjuvant" refers to excipients and additives used in the production of drugs and formulation of prescriptions, and is all substances contained in a pharmaceutical preparation except for active ingredients. For details, see Pharmacopoeia of the People's Republic of China (2020 Edition) or Handbook of Pharmaceutical EMcipients (Raymond C Rowe, 2009).

The term "treat/treating/treatment" refers to any of the following: (1) alleviating one or more biological manifestations of a disease; (2) interfering with one or more points in the biological cascade leading to a disease; and (3) slowing down the progression of one or more biological manifestations of a disease.

The term "prevent/preventing/prevention" refers to reducing the risk of developing a disease.

The term "patient" refers to any animal, preferably a mammal, most preferably a human, who has been or is about to be treated. Mammals include but not limited to cattle, horse, sheep, pig, cat, dog, mouse, rat, rabbit, guinea pig, monkey, human, etc.

On the basis of not departing from common knowledge in the art, the above-mentioned various preferred conditions can be combined in any manner, such that various preferred examples of the present disclosure are obtained.

Reagents and raw materials used in the present disclosure are all commercially available.

The positive effects of the present disclosure lie in: The compounds of the present invention have good affinity, agonistic activity or selectivity for dopamine D2 receptors.

BRIEF DESCRIPTION OF THE DRAWINGS

FIG. 1 shows an X-single crystal diffraction pattern of the crystal of the compound as shown in pNs-(+)-I-10.

DETAILED DESCRIPTION OF THE PREFERRED EMBODIMENT

The present disclosure is further described below by way of examples; however, the present disclosure is not limited to the scope of the described examples. For the experimental methods in which no specific conditions are specified in the following examples, selections are made according to conventional methods and conditions or according to the product instructions.

Materials and Methods

1. Cell Culture

Human renal epithelial cell HEK-293T were cultured in DMEM medium containing 10% fetal bovine serum (FBS), and the culture dish was cultured at 37° C. and 5% $CO_2$. After the culture dish was covered with adherent cells, the culture medium was removed with a pipette. By adding 1 mL of phosphate buffered saline (pH 7.4), the cells were washed slowly to remove excess serum, and then 800 μL of 0.25% trypsin was added. The cells were placed in an incubator and digested for 2 min, and then taken out and observed under the microscope. The cells became round and swam freely at the bottom of the dish. 2 mL of culture medium containing 10% serum was added to stop the digestion, and the cells were gently pipetted with a 1 mL pipette to disperse them into single cells. Finally, further subculture or further experiment was performed according to the experimental needs.

2. Cell Transfection

The day before transfection, HEK-293T cells grown in a 10 cm diameter dish were splitted at 1:4 ratio into a 6 cm culture dish for subculture. After 20 hours, when the cell density reached 50%-70%, the cells were ready for transfection. 500 μL of 150 mM sodium chloride was taken and placed in a clean EP tube, an appropriate amount of plasmids was added, and at the same time, the transfection reagent PEI was added in the amount of 4 times that of the plasmids, mixed well and incubated at room temperature for 20 minutes. 500 μL of transfection solution was added dropwise above the dish to the dish and shaken gently to mix same evenly.

3. Preparation of a Cell Membrane Component Containing Specific Dopamine $D_2$ Receptors A 10 cm diameter dish was used for transfection with 10 ng of the dopamine $D_2$ receptors and 40 μL of PEI. After 48 hours, the 10 cm dish was taken out from the cell culture room and the cultured cells had expressed the dopamine $D_2$ receptors. A vacuum pump was used to suck off the culture medium, 3 mL of lysis buffer (50 mM Tris hydrochloric acid buffer, pH 7.4) was added to each well, and the cells were placed in a 4° C. freezer for 10 minutes. After the cells were detached, the cells were transferred to a 15 mL centrifuge tube and centrifuged at 1500 rpm for 5 minutes at 4° C., and the supernatant was discarded. The cell pellet was transferred to a tissue homogenizer, and 3 mL of lysis buffer was added and fully ground until the cells were broken. Then, cell suspension was equally divided into several EP tubes, centrifuged at 4° C. and 12000 rpm for 5 min, and the supernatant was discarded. The precipitate was the cell membrane component containing the dopamine $D_2$ receptors and stored at −80° C.

4. Radioligand-Receptor Binding Experiment

A ligand-receptor binding experiment was performed on HEK-293T membrane component transiently expressing the dopamine $D_2$ receptors. First, a standard binding buffer (50 mM HEPES, 50 mM NaCl, 5 mM $MgCl_2$, 0.5 mM EDTA, pH 7.4) was added to the cell membrane component containing the dopamine $D_2$ receptors, and the cell membrane was disrupted and resuspended with an electric tissue homogenizer. 30 μL of membrane protein suspension was added to each well of a 96-well plate. Then, 30 μL of different drugs were added to the 96-well plate from left to right to ensure that the final drug concentrations were $10^{-5}$ M, $10^{-6}$ M, $10^{-7}$ M, $10^{-8}$ M, $10^{-9}$ M and 0 M, with two replicates per treatment. Next, 30 μL [$^3$H]—N-Methylspiperone was added to each well of the 96-well plate, and the plate was incubated for 2 hours at room temperature in the dark. The unbound isotopes were removed by Whatman GF/C filter membrane and vacuum pump, and the isotopes bound to the receptors were detected by MicroBeta isotope liquid scintillation counter.

5. G Protein $G\alpha_{i1\text{-}\gamma 9}$ Dissociation Experiment Based on Bioluminescence Resonance Energy Transfer (BRET)

To examine downstream G protein signaling mediated by dopamine $D_2$ receptors, 6 cm dish was used for transfection with 1 μg of dopamine $D_2$ receptors, 1 μg of $G\alpha_{i1}$ fused to seaweed luciferase ($G\alpha_{i1}$-Rluc), 1 μg of $G\beta_3$, 1 μg of $G\gamma_9$ fused to green fluorescent protein ($G\gamma_9$-GFP) and 16 μL of transfection reagent PEI. The next day, the overgrown cells were digested by using 0.25% trypsin and plated a 96-well plate at the amount of cells contained in a 6 cm culture dish with overgrown cells, and 100 μL of culture medium was added to each well. On the third day, the drugs were added for test. The 96-well plate was taken out from the cell culture room to remove the culture medium, 40 μL of buffer (1×HBSS, 20 mM HEPES, pH 7.4) containing the substrate coelenterazine 400a (7.5 μM) was added to each well, and then 20 μL of different drugs were added in turn from left to right to ensure that the final concentration of the drugs decreased gradually from bottom to top, and each treatment was repeated twice. The readings at 395 nm and 510 nm were determined using an LB940 Mithras plate reader (Berthold Technologies), and the ratio of the value at 510 nm to the value at 395 nm was taken as the final value.

6. β-arrestin2 Recruitment Experiment Based on Bioluminescence Resonance Energy Transfer (BRET)

To examine the downstream β-arrestin2 signaling pathway mediated by dopamine $D_2$ receptors, 6 cm dish was used for transfection with 500 μg of dopamine $D_2$ receptors fused to seaweed luciferase ($D_2$-Rluc), 500 μg of G protein-coupled receptor kinase 2 (GRK2), 2500 μg of β-arrestin2 fused to green fluorescent protein (GFP2-ARRB2) and 14 μL of transfection reagent PEI. The next day, the overgrown cells were digested and plated a 96-well plate at the amount of cells contained in a 6 cm culture dish with overgrown cells, and 100 μL of culture medium was added to each well. On the third day, the drugs were added for test. The 96-well plate was taken out from the cell culture room to remove the culture medium, 40 μL of buffer (1×HBSS, 20 mM HEPES, pH 7.4) containing the substrate coelenterazine 400a (7.5 μM) was added to each well, and then 20 μL of different drugs were added in turn from left to right to ensure that the final concentration of the drugs decreased gradually from bottom to top, and each treatment was repeated twice. The readings at 395 nm and 510 nm were determined using an LB940 Mithras plate reader (Berthold Technologies), and the ratio of the value at 510 nm to the value at 395 nm was taken as the final value.

Preparation of Starting Material (A) (6,6a,7,8,9,10-hexahydro-4H-pyrazino[1,2-a]pyrrolo[4,3,2-de]quinoline)

(A)

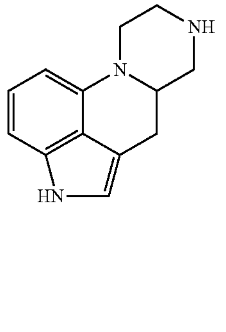

It was prepared according to the method in the literature (Krogsgaard-Larsen et al., J. Med. Chem. 2014, 57, 5823-5828). It is a brown solid. $^1$H NMR (800 MHz, $CDCl_3$) δ 7.82 (s, 1H), 7.08 (t, J=7.8 Hz, 1H), 6.81 (d, J=8.1 Hz, 1H), 6.73 (t, J=1.9 Hz, 1H), 6.34 (d, J=7.6 Hz, 1H), 3.81 (d, J=11.5 Hz, 1H), 3.21 (dd, J=12.4, 3.2 Hz, 2H), 3.10-3.03 (m, 2H), 2.97 (dd, J=15.2, 3.7 Hz, 1H), 2.83-2.79 (m, 3H).

Example 1: 7-(4-(4,6,6a,7,9,10-hexahydro-8H-pyrazino[1,2-a]pyrrolo[4,3,2-de]quinolin-8-yl)butoxy)-3,4-dihydroquinolin-2(1H)-one (Compound I-1)

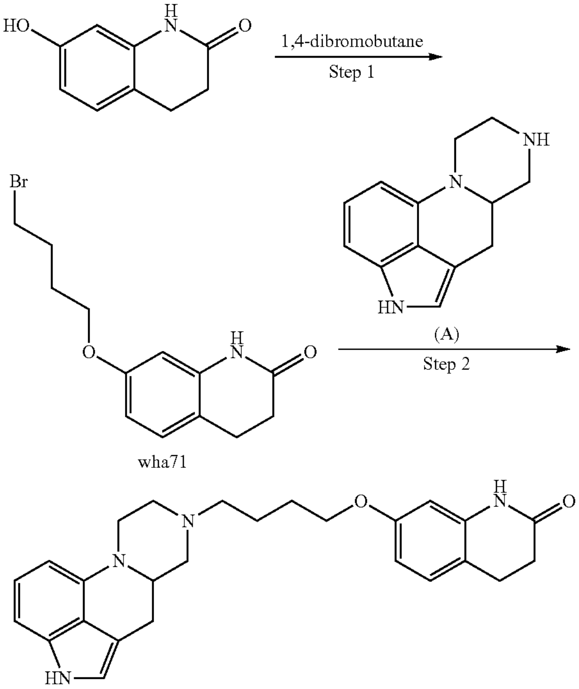

wha71

I-1

Step 1: 7-hydroxy-3,4-dihydroquinolin-2(1H)-one (1.5 g, 9.19 mmol), 1,4-dibromobutane (5.92 g, 27.6 mmol), $K_2CO_3$ (1.9 g, 13.7 mmol) and solvent DMF (20 mL) were successively added into a round bottom flask, and the reaction system was stirred overnight at room temperature. The solvent was evaporated under reduced pressure and the residue was purified by flash column chromatography (eluent: ethyl acetate/petroleum ether mixture containing 20-50% ethyl acetate) to give intermediate wha71 (1.75 g, 64%) as a white solid. $^1$H NMR (800 MHz, $CDCl_3$) δ 7.74 (s, 1H), 7.05 (d, J=8.3 Hz, 1H), 6.52 (dd, J=8.3, 1.9 Hz, 1H), 6.30 (d, J=2.3 Hz, 1H), 3.97 (t, J=6.1 Hz, 2H), 3.48 (t, J=6.6 Hz, 2H), 2.90 (t, J=7.5 Hz, 2H), 2.65-2.60 (m, 2H), 2.09-2.03 (m, 2H), 1.95-1.93 (m, 2H). HR-MS (ESI, m/z): $C_{13}H_{17}BrNO_2^+$ $[M+H]^+$, calculated: 298.0437; found: 298.0432 and 300.0412.

Step 2: The intermediate A (50 mg, 0.23 mmol), the intermediate wha71 (82 mg, 0.28 mmol) and $K_2CO_3$ (0.2 g, 1.38 mmol) were successively added into a round bottom flask, then solvents THF (3 mL) and DMSO (1 mL) were added. The reaction system was heated and stirred at 60° C. for 16 hours. After the reaction was completed, the solvent was removed and purified by flash silica gel column chromatography (eluent: 0-10% methanol/dichloromethane) to obtain compound I-1 (90 mg, 91%) as an off-white solid. $^1$H NMR (800 MHz, DMSO-$d_6$) δ 10.51 (s, 1H), 9.97 (d, J=7.1 Hz, 1H), 7.03 (d, J=8.2 Hz, 1H), 6.88 (t, J=7.7 Hz, 1H), 6.78 (s, 1H), 6.70 (d, J=8.1 Hz, 1H), 6.48 (dd, J=8.2, 2.5 Hz, 1H), 6.43 (d, J=2.5 Hz, 1H), 6.20 (d, J=7.5 Hz, 1H), 3.96-3.86 (m, 2H), 3.74-3.69 (m, 1H), 3.09-3.00 (m, 2H), 2.96-2.87 (m, 2H), 2.76 (t, J=6.8 Hz, 2H), 2.71-2.61 (m, 2H), 2.40 (t, J=7.7 Hz, 4H), 2.20-2.14 (m, 1H), 2.03-1.88 (m, 1H), 1.76-1.68 (m, 2H), 1.65-1.60 (m, 2H); $^{13}$C NMR (201 MHz, DMSO-$d_6$) δ 170.40, 157.75, 140.00, 139.26, 134.17, 128.46, 123.05, 117.70, 116.56, 115.74, 107.57, 106.08, 103.24, 101.80, 98.96, 66.72, 55.71, 55.00, 53.69, 50.62, 43.43, 30.79, 26.26, 25.87, 24.03, 20.32. HR-MS (ES, m/z): $C_{26}H_{31}N_4O_2^+$ [M+H]$^+$, calculated: 431.2442; found: 431.2440.

Example 2: 7-(4-(4,6,6a,7,9,10-hexahydro-8H-pyrazino[1,2-a]pyrrolo[4,3,2-de]quinolin-8-yl)butoxy)quinolin-2(1H)-one (Compound I-2)

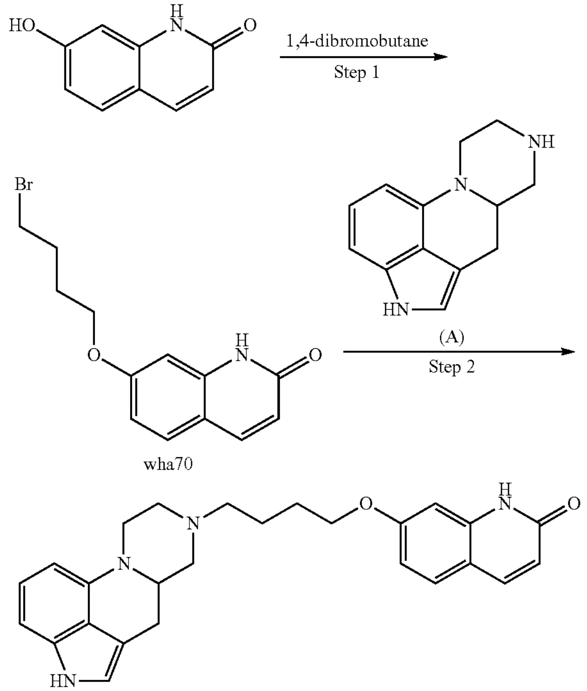

wha70

I-2

Step 1: Following the method of step 1 of example 1, the alkylation reaction was carried out using "7-hydroxy-quinolin-2(1H)-one" and 1,4-dibromobutane as raw materials to prepare intermediate wha70 (1.06 g, 38%) as a white solid. $^1$H NMR (800 MHz, $CDCl_3$) δ 7.79 (d, J=9.4 Hz, 1H), 7.48 (d, J=8.4 Hz, 1H), 6.87-6.83 (m, 2H), 6.60 (d, J=9.3 Hz, 1H), 4.11 (t, J=6.0 Hz, 2H), 3.51 (t, J=6.6 Hz, 2H), 2.12-2.07 (m, 2H), 2.04-1.97 (m, 2H). HR-MS (ESI, m/z): $C_{13}H_{15}BrNO_2^+$ [M+H]$^+$, calculated: 296.0281; found: 296.0220.

Step 2: Following the method of step 2 of example 1, the intermediate wha70 and the starting material (A) were subjected to alkylation reaction to obtain compound I-2 (60 mg, 61%) which was purified by preparative HPLC: $t_R$=18.5 min (20-80% MeOH/$H_2O$) to obtain a white solid. $^1$H NMR (800 MHz, $CD_3OD$) δ 7.91 (d, J=9.4 Hz, 1H), 7.61 (d, J=8.7 Hz, 1H), 7.03 (t, J=7.8 Hz, 1H), 6.92 (dd, J=8.7, 2.4 Hz, 1H), 6.89-6.84 (m, 3H), 6.47 (d, J=9.4 Hz, 1H), 6.40 (d, J=7.5 Hz, 1H), 4.19 (t, J=5.8 Hz, 3H), 3.79 (t, J=10.0 Hz, 2H), 3.41-3.33 (m, 4H), 3.19 (dd, J=15.2, 3.9 Hz, 1H), 3.14-3.06 (m, 2H), 2.90 (dd, J=15.0, 9.5 Hz, 1H), 2.09-2.05 (m, 2H), 2.00-1.96 (m, 2H); $^{13}$C NMR (201 MHz, DMSO-$d_6$) δ 162.35, 160.31, 140.68, 140.08, 139.97, 134.18, 129.32, 123.06, 118.61, 117.70, 116.57, 113.46, 110.81, 106.06, 103.25, 98.97, 98.73, 67.01, 55.65, 54.95, 53.67, 50.59, 43.41, 26.25, 25.76, 20.25; HR-MS (ESI, m/z): $C_{26}H_{29}N_4O_2^+$ [M+H]$^+$, calculated: 429.2285; found: 429.2281.

Compound I-2 was chirally resolved.

Chiral analysis conditions: chiral column Daicel CHIRALCEL OD-H (ODH0CD-TC013) (Daicel), column volume: 0.46 cm (diameter)×15 cm (column length) (5 μm filler); Mobile phase: MeOH/Diethylamine=100/0.1 (V/V/); flow rate: 1.0 mL/min; wavelength: UV 214 nm; temperature: 35° C.; HPLC instrument: Shimadzu LC-20AD. Peak 1 (prepeak) $t_R$=5.805 min; peak 2 (postpeak): $t_R$=7.548 min.

Chiral preparation conditions: chiral column CHIRALCEL OD (Dacel), column volume: 5.0 cm (diameter)×25 cm (column length) (10 μm filler); Mobile phase: MeOH/Diethylamine=100/0.1 (V/V/); flow rate: 30 mL/min; wavelength: UV 214 nm; temperature: 38° C.

Resolution preparation: racemate compound I-2 (0.103 g). Peak 1 (prepeak) $t_R$=5.830 min, 0.048 g obtained, >98% ee; optical rotation $[\alpha]_D^{25}$=+50.33° (c=0.1, MeOH), >98% ee (the compound is a trifluoroacetate). peak 2 (postpeak) $t_R$=7.60 min, 0.042 g obtained, >98% ee; optical rotation $[\alpha]_D^{25}$=−45.00° (c=0.1, MeOH), >98% ee (the compound is a trifluoroacetate).

Example 3: 5-(4-(4,6,6a,7,9,10-hexahydro-8H-pyrazino[1,2-a]pyrazolo[4,3,2-de]quinolin-8-yl)butoxy)benzo[d]thiazole (Compound I-3)

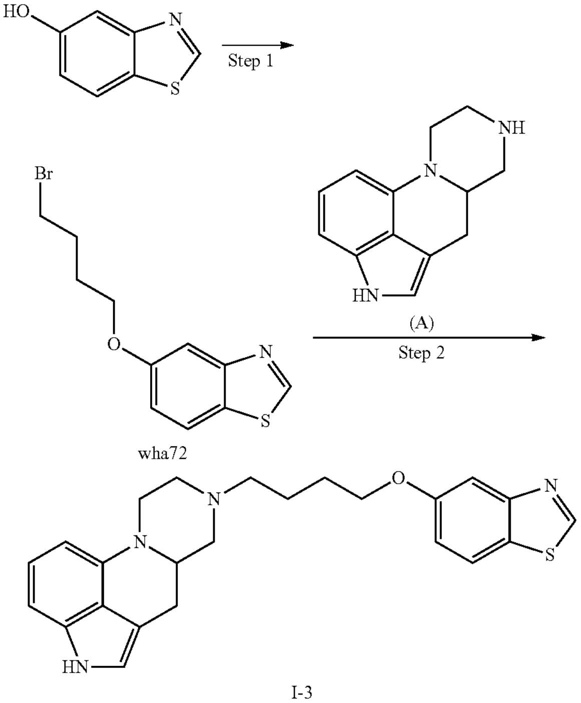

wha72

I-3

Step 1: Following the method in step 1 of example 1, “5-hydroxy-benzo[d]thiazole” and 1,4-dibromobutane were used as raw materials to prepare intermediate wha72 (1.23 g, 65%) as a white solid. $^{1}$H NMR (800 MHz, $CDCl_3$) δ 8.98 (s, 1H), 7.80 (d, J=8.7 Hz, 1H), 7.60 (d, J=2.4 Hz, 1H), 7.09 (dd, J=8.7, 2.4 Hz, 1H), 4.10 (t, J=6.1 Hz, 2H), 3.51 (t, J=6.6 Hz, 2H), 2.13-2.09 (m, 2H), 2.04-1.97 (m, 2H). HR-MS (ESI, m/z): $C_{11}H_{13}BrNOS^+$ $[M+H]^+$, calculated: 285.9896; found: 285.9894 and 287.9875.

Step 2: Following the method of step 2 of example 1, the intermediate wha72 and the starting material (A) were subjected to alkylation reaction to obtain compound I-3 (30 mg, 51%) as a yellow solid. $^{1}$H NMR (800 MHz, $CD_3OD$) δ 9.18 (s, 1H), 7.90 (d, J=8.8 Hz, 1H), 7.59 (d, J=2.4 Hz, 1H), 7.16 (dd, J=8.8, 2.4 Hz, 1H), 6.96 (t, J=7.8 Hz, 1H), 6.78 (d, J=8.1 Hz, 1H), 6.73 (d, J=1.6 Hz, 1H), 6.29 (d, J=7.5 Hz, 1H), 4.15-4.08 (m, 2H), 3.80 (d, J=12.0 Hz, 1H), 3.15-3.10 (m, 2H), 3.09-3.05 (m, 1H), 2.95 (dd, J=15.2, 3.6 Hz, 1H), 2.86-2.83 (m, 1H), 2.79-2.76 (m, 1H), 2.53 (t, J=4.8 Hz, 2H), 2.37-2.34 (m, 1H), 2.12 (t, J=10.9 Hz, 1H), 1.92-1.85 (m, 2H), 1.83-1.77 (m, 2H). $^{13}$C NMR (201 MHz, $CDCl_3$) δ 158.55, 155.05, 154.79, 142.34, 134.44, 125.59, 124.18, 122.15, 118.18, 116.59, 115.04, 109.55, 106.60, 102.06, 99.12, 68.28, 60.25, 58.35, 56.28, 53.13, 46.38, 27.63, 27.36, 23.60. HR-MS (ESI, m/z): $C_{24}H_{27}N_4OS^+$ $[M+H]^+$, calculated: 419.1900; found: 419.1901.

Example 4: 5-(4-(4,6,6a,7,9,10-hexahydro-8H-pyrazino[1,2-a]pyrrolo[4,3,2-de]quinolin-8-yl)butoxy)-2-methylbenzo[d]oxazole (Compound I-4)

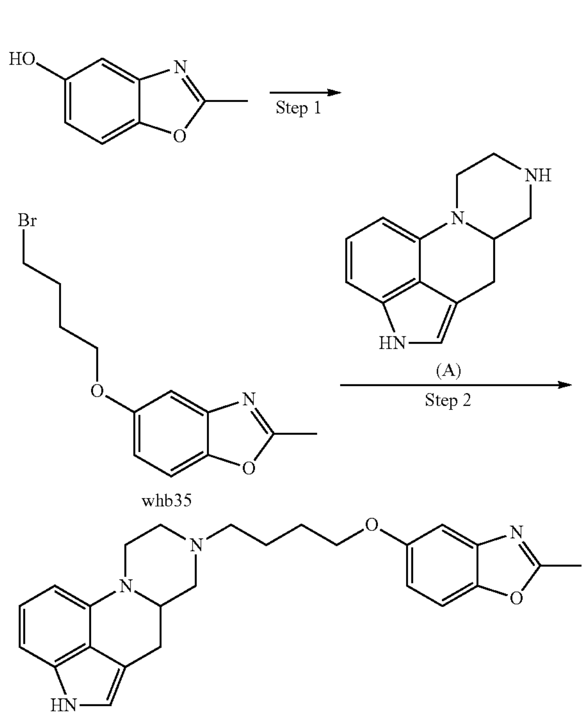

whb35
I-4

Step 1: Following the method of step 1 of example 1, “2-methyl-5-hydroxy-benzo[d]thiazole” and 1,4-dibromobutane were used as raw materials to prepare intermediate whb35 (0.15 g, 31%) as a pale yellow solid. $^{1}$H NMR (800 MHz, $CDCl_3$) δ 7.35 (d, J=8.8 Hz, 1H), 7.14 (d, J=2.5 Hz, 1H), 6.89 (dd, J=8.8, 2.5 Hz, 1H), 4.03 (t, J=6.1 Hz, 2H), 3.50 (t, J=6.7 Hz, 2H), 2.64 (s, 3H), 2.12-2.06 (m, 2H), 2.00-1.94 (m, 2H). $^{13}$C NMR (201 MHz, deuterated chloroform) δ 164.83, 156.41, 145.75, 142.33, 113.34, 110.45, 103.63, 68.18, 67.83, 33.58, 29.64, 28.06, 14.75. HR-MS (ESI, m/z): $C_{12}H_{15}BrNO_2^+$ $[M+H]^+$, calculated: 284.0281; found: 284.0280 and 286.0281.

Step 2: Following the method of step 2 of example 1, the intermediate whb35 and the starting material (A) were subjected to alkylation reaction to obtain compound I-4 (41 mg, 43%) as an off-white solid. $^{1}$H NMR (600 MHz, $CDCl_3$) δ 7.90 (s, 1H), 7.33 (d, J=8.8 Hz, 1H), 7.13 (d, J=1.3 Hz, 1H), 7.07 (t, J=7.7 Hz, 1H), 6.88 (dd, J=8.8, 1.8 Hz, 1H), 6.79 (d, J=8.1, 1.2 Hz, 1H), 6.71 (t, J=1.8 Hz, 1H), 6.33 (d, J=7.6 Hz, 1H), 4.03 (t, J=6.2 Hz, 2H), 3.80 (d, J=12.1 Hz, 1H), 3.23 (t, J=11.0 Hz, 1H), 3.11 (d, J=3.8 Hz, 2H), 3.01-2.93 (m, 2H), 2.81 (dd, J=13.8, 11.0 Hz, 1H), 2.60 (d, J=1.2 Hz, 3H), 2.52 (t, J=7.6 Hz, 2H), 2.41-2.34 (m, 1H), 2.14 (t, J=10.9 Hz, 1H), 1.88-1.85 (m, 2H), 1.82-1.74 (m, 2H). $^{13}$C NMR (201 MHz, $CDCl_3$) δ164.76, 156.53, 145.69, 142.42, 134.44, 124.15, 118.17, 115.10, 113.33, 110.39, 109.40, 103.68, 102.12, 99.14, 68.64, 60.00, 58.31, 56.13, 52.96, 46.24, 29.82, 27.69, 27.43, 23.45, 14.73. HR-MS (ESI, m/z): $C_{25}H_{29}N_4O_2^+$ $[M+H]^+$, calculated: 417.2285; found: 417.2289.

Example 5: 6-(4-(4,6,6a,7,9,10-hexahydro-8H-pyrazino[1,2-a]pyrrolo[4,3,2-de]quinolin-8-yl)butoxy)-3-methylbenzo[d]isoxazole (Compound I-5)

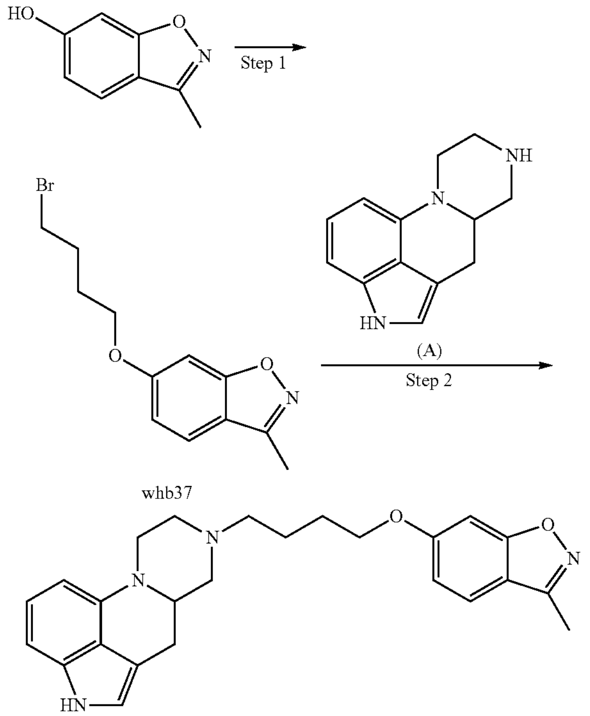

whb37
I-5

Step 1: Following the method of step 1 of example 1, “3-methyl-6-hydroxy-benzo[d]isoxazole” and 1,4-dibromobutane were used as raw materials to prepare intermediate whb37 (0.16 g, 42%) as a pale yellow solid. $^{1}$H NMR (800 MHz, $CDCl_3$) δ 7.52 (d, J=8.6 Hz, 1H), 7.00 (d, J=2.3 Hz, 1H), 6.89 (dd, J=8.7, 2.4 Hz, 1H), 4.03 (t, J=6.1 Hz, 2H), 3.50 (t, J=6.6 Hz, 2H), 2.62 (s, 3H), 2.11-2.07 (m, 2H), 2.01-1.95 (m, 2H). $^{13}$C NMR (201 MHz, $CDCl_3$) δ 162.98, 157.05, 151.85, 135.32, 119.44, 112.62, 96.17, 67.79, 33.52, 29.57, 28.00, 14.58. HR-MS (ESI, m/z): $C_{12}H_{15}BrNO_2^+$ $[M+H]^+$, calculated: 284.0281; found: 284.0261 and 286.0241.

Step 2: Following the method of step 2 of example 1, the intermediate whb37 and the starting material (A) were subjected to alkylation reaction to obtain compound I-5 (58 mg, 60%) as an off-white solid. $^1$H NMR (600 MHz, $CDCl_3$) δ 8.03 (s, 1H), 7.49 (d, J=8.7 Hz, 1H), 7.06 (t, J=7.8 Hz, 1H), 7.00 (d, J=2.5 Hz, 1H), 6.89 (dd, J=8.7, 2.4 Hz, 1H), 6.77 (d, J=8.1 Hz, 1H), 6.69 (s, 1H), 6.32 (d, J=7.6 Hz, 1H), 4.02 (t, J=6.3 Hz, 2H), 3.79 (d, J=12.0 Hz, 1H), 3.21 (t, J=10.8 Hz, 1H), 3.09-3.06 (m, 2H), 2.98-2.90 (m, 2H), 2.81 (dd, J=15.4, 10.9 Hz, 1H), 2.58 (s, 3H), 2.52-2.46 (m, 2H), 2.34 (t, J=11.7 Hz, 1H), 2.11 (t, J=10.9 Hz, 1H), 1.91-1.82 (m, 2H), 1.79-1.73 (m, 2H). $^{13}$C NMR (201 MHz, $CDCl_3$) δ 162.87, 157.17, 151.85, 142.22, 135.21, 134.41, 124.09, 119.37, 118.15, 115.09, 112.65, 109.35, 102.12, 99.07, 96.13, 68.58, 60.10, 58.25, 56.19, 53.01, 46.28, 27.69, 27.34, 23.43, 14.53. HR-MS (ESI, m/z): $C_{25}H_{29}N_4O_2^+$ $[M+H]^+$, calculated: 417.2285; found: 417.2290.

Embodiment 6: 8-(4-((2,3-dihydrobenzofuran-6-yl)oxy)butyl)-6,6a,7,8,9,10-hexahydro-4H-pyrazino[1,2-a]pyrrolo[4,3,2-de]quinoline (Compound I-6)

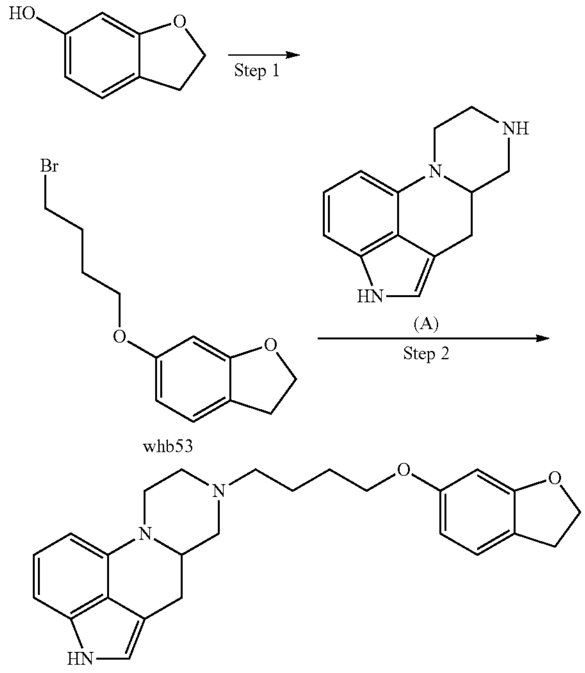

whb53

I-6

Step 1: Following the method in step 1 of example 1, “6-hydroxy-2,3-dihydrobenzofuran” and 1,4-dibromobutane were used as raw materials to prepare intermediate whb53 (0.29 g, 81%) as a white solid. $^1$H NMR (800 MHz, $CDCl_3$) δ 7.05 (d, J=7.9 Hz, 1H), 6.39-6.35 (m, 2H), 4.57 (t, J=8.6 Hz, 2H), 3.95 (t, J=6.1 Hz, 2H), 3.48 (t, J=6.7 Hz, 2H), 3.13 (t, J=8.6 Hz, 2H), 2.08-2.02 (m, 2H), 1.95-1.89 (m, 2H). $^{13}$C NMR (201 MHz, $CDCl_3$) δ 161.44, 159.64, 124.93, 119.03, 106.53, 96.87, 72.16, 67.24, 33.65, 29.64, 29.22, 28.14.

Step 2: Following the method of step 2 of example 1, the intermediate wha53 and the starting material (A) were subjected to alkylation reaction to obtain compound I-6 (30 mg, 32%) as a white solid. $^1$H NMR (800 MHz, $CDCl_3$) δ 7.82 (s, 1H), 7.08 (t, J=7.8 Hz, 1H), 7.06-7.01 (m, 1H), 6.80 (d, J=8.1 Hz, 1H), 6.73 (s, 1H), 6.40-6.37 (m, 2H), 6.33 (d, J=7.6 Hz, 1H), 4.56 (t, J=8.6 Hz, 2H), 3.96 (t, J=6.2 Hz, 2H), 3.82-3.78 (m, 1H), 3.23-3.16 (m, 1H), 3.15-3.10 (m, 2H), 3.11-3.06 (m, 2H), 3.00-2.95 (m, 2H), 2.82 (dd, J=15.3, 10.8 Hz, 1H), 2.51-2.46 (m, 2H), 2.39-2.31 (m, 1H), 2.14-2.07 (m, 1H), 1.85-1.80 (m, 2H), 1.79-1.71 (m, 2H). $^{13}$C NMR (201 MHz, $CDCl_3$) δ161.41, 159.77, 134.44, 124.90, 124.18, 118.85, 118.17, 115.09, 109.46, 106.60, 102.11, 99.16, 96.90, 72.13, 68.06, 59.98, 58.30, 56.12, 52.95, 46.23, 29.21, 27.69, 27.40, 23.40. HR-MS (ESI, m/z): $C_{25}H_{30}N_3O_2^+$ $[M+H]^+$, calculated: 404.2333; found: 404.2330.

Example 7: 7-(3-(4,6,6a,7,9,10-hexahydro-8H-pyrazino[1,2-a]pyrrolo[4,3,2-de]quinolin-8-yl)propoxy)-3,4-dihydroquinolin-2(1H)-one (Compound I-7)

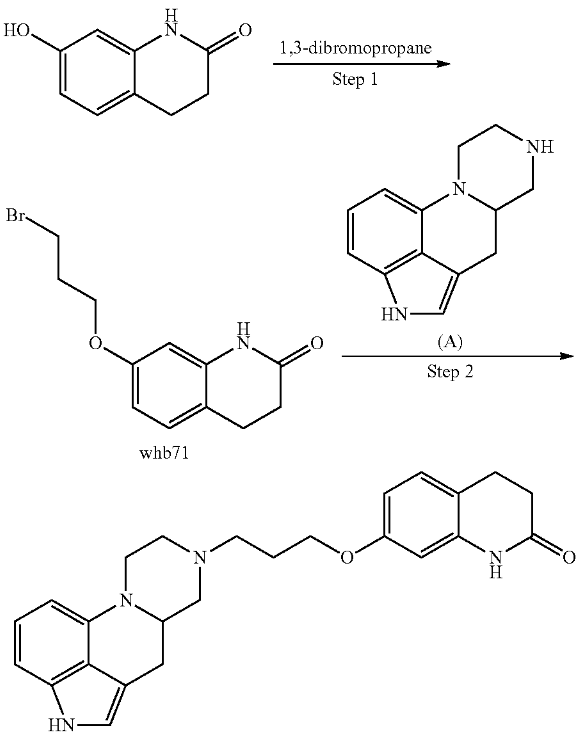

whb71

I-7

Step 1: Following the method in step 1 of example 1, “7-hydroxy-3,4-dihydroquinoline-2(1H)-one” and 1,3-dibromopropane were used as raw materials to prepare intermediate whb71 (2.85 g, 81%) as a white solid. $^1$H NMR (800 MHz, $CDCl_3$) δ 8.94 (s, 1H), 7.05 (d, J=8.1 Hz, 1H), 6.54 (dd, J=7.9, 2.4 Hz, 1H), 6.41 (d, J=2.4 Hz, 1H), 4.07 (t, J=5.8 Hz, 2H), 3.59 (t, J=6.4 Hz, 2H), 2.90 (t, J=8.7 Hz, 2H), 2.63 (t, J=8.7 Hz, 2H), 2.31-2.28 (m, 2H). HR-MS (ESI, m/z): $C_{12}H_{15}BrNO_2^+$ $[M+H]^+$, calculated: 284.0281, found: 284.0273 and 286.0255.

Step 2: Following the method of step 2 of example 1, the intermediate whb71 and the starting material (A) were subjected to alkylation reaction to obtain compound I-7 (60 mg, 63%) as an off-white solid. $^{1}H$ NMR (800 MHz, $CDCl_3$) δ 7.95 (s, 1H), 7.89 (s, 1H), 7.08 (t, J=7.8 Hz, 1H), 7.04 (d, J=8.3 Hz, 1H), 6.80 (d, J=8.1 Hz, 1H), 6.72 (s, 1H), 6.54 (dd, J=8.3, 2.4 Hz, 1H), 6.34 (d, J=7.6 Hz, 1H), 6.32 (d, J=2.4 Hz, 1H), 4.02 (t, J=6.3 Hz, 2H), 3.81 (d, J=11.8 Hz, 1H), 3.22 (t, J=9.7 Hz, 1H), 3.12-3.07 (m, 2H), 3.02-2.93 (m, 2H), 2.89 (t, J=7.5 Hz, 2H), 2.83 (dd, J=15.2, 11.0 Hz, 1H), 2.39 (t, J=11.6 Hz, 1H), 2.16 (t, J=10.56 Hz, 1H), 2.05-2.01 (m, 2H), 1.81-1.67 (m, 4H). $^{13}C$ NMR (201 MHz, DMSO-$d_6$) δ 170.31, 157.88, 141.95, 139.21, 134.02, 128.42, 122.97, 117.86, 115.56, 107.66, 102.07, 101.69, 98.01, 65.86, 59.55, 56.06, 54.40, 52.51, 45.91, 30.76, 27.09, 26.17, 24.00. HR-MS (ESI, m/z): $C_{25}H_{29}N_4O_2^+$ $[M+H]^+$, calculated: 417.2285; found: 417.2284.

Example 8: 7-(3-(4,6,6a,7,9,10-hexahydro-8H-pyrazino[1,2-a]pyrrolo[4,3,2-de]quinolin-8-yl)propoxy)quinolin-2(1H)-one (Compound I-8)

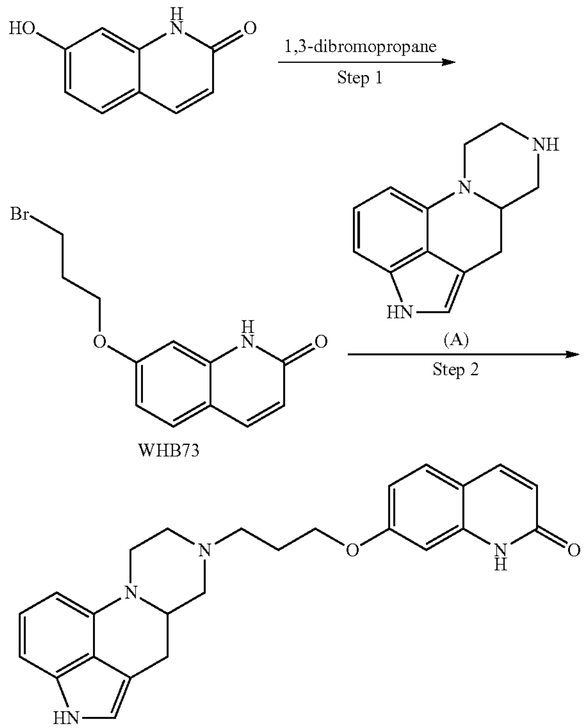

I-8

Step 1: Following the method in step 1 of example 1, "7-hydroxy-quinolin-2(1H)-one" and 1,3-dibromopropane were used as raw materials to prepare intermediate whb73 (1.36 g, 39%) as a white solid. $^{1}H$ NMR (800 MHz, $CDCl_3$) δ 12.45 (s, 1H), 7.74 (d, J=9.3 Hz, 1H), 7.46 (d, J=8.6 Hz, 1H), 6.88 (d, J=2.3 Hz, 1H), 6.82 (dd, J=8.0 and 2.4 Hz, 1H), 6.57 (d, J=9.4 Hz, 1H), 4.21 (t, J=5.7 Hz, 2H), 3.62 (t, J=6.5 Hz, 2H), 2.37-2.34 (m, 2H). HR-MS (ESI, m/z): $C_{12}H_{13}BrNO_2^+$ $[M+H]^+$, calculated: 282.0124; found: 282.0128 and 284.0109.

Step 2: Following the method of step 2 of example 1, the intermediate whb73 and the starting material (A) were subjected to alkylation reaction to obtain compound I-8 (0.10 g, 51%) as a white solid. $^{1}H$ NMR (600 MHz, $CD_3OD$) δ 7.91 (d, J=9.4 Hz, 1H), 7.62 (d, J=8.7 Hz, 1H), 7.07-7.01 (m, 1H), 6.94 (dd, J=8.7, 2.4 Hz, 1H), 6.91-6.85 (m, 3H), 6.48 (d, J=9.4 Hz, 1H), 6.42 (d, J=7.6 Hz, 1H), 4.26 (t, J=5.7 Hz, 2H), 3.88-3.82 (m, 2H), 3.52-3.46 (m, 2H), 3.42-3.38 (dd, J=12.6, 3.5 Hz, 1H), 3.24-3.08 (m, 3H), 2.92 (dd, J=15.3, 9.6 Hz, 1H), 2.41-2.36 (m, 2H), 2.07-2.03 (m, 1H), 1.62 (t, J=7.4 Hz, 1H). $^{13}C$ NMR (201 MHz, DMSO-$d_6$) δ 162.32, 160.03, 140.63, 140.05, 134.16, 129.37, 123.05, 118.78, 117.70, 116.56, 113.60, 110.58, 106.08, 103.23, 98.90, 65.09, 53.78, 53.50, 50.77, 48.62, 43.51, 26.29, 23.44. HR-MS (ESI, m/z): $C_{25}H_{27}N_4O_2^+$ $[M+H]^+$, calculated: 415.2129; found: 415.2129.

Example 9: 8-(3-(benzo[d][1,3]dioxol-5-yloxy)propyl)-6,6a,7,8,9,10-hexahydro-4H-pyrazino[1, 2-a]pyrrolo[4,3,2-de]quinoline (Compound I-9)

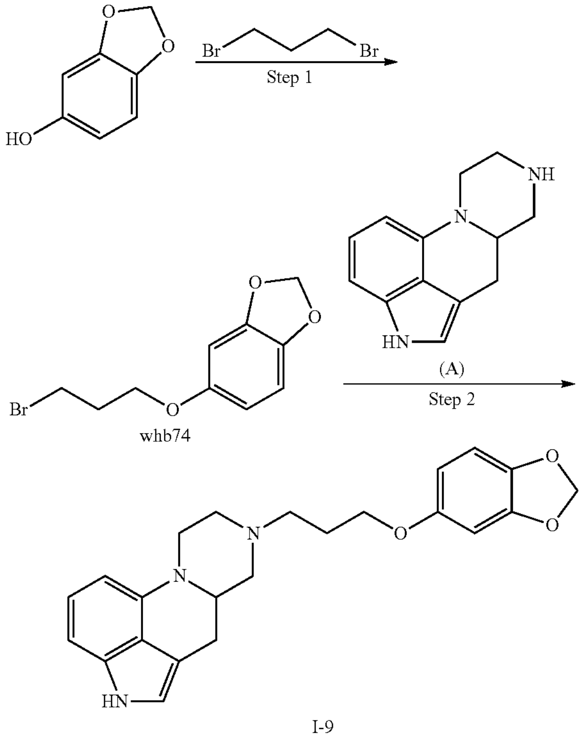

I-9

Step 1: Following the method in step 1 of example 1, sesamol (CAS #533-31-3) and 1,3-dibromopropane were used as raw materials to prepare intermediate whb74 (1.67 g, 45%) as a white solid. $^{1}H$ NMR (800 MHz, $CDCl_3$) δ 6.70 (d, J=8.5 Hz, 1H), 6.49 (d, J=2.5 Hz, 1H), 6.33 (dd, J=8.5, 2.5 Hz, 1H), 5.91 (s, 2H), 4.02 (t, J=5.8 Hz, 2H), 3.59 (t, J=6.4 Hz, 2H), 2.29-2.26 (m, 2H).

Step 2: Following the method of step 2 of example 1, the intermediate whb74 and the starting material (A) were subjected to alkylation reaction to prepare compound I-9 (20 mg, 22%) as an off-white solid. $^{1}H$ NMR (600 MHz, $CDCl_3$) δ 7.87 (s, 1H), 7.07 (t, J=7.8 Hz, 1H), 6.79 (d, J=8.1 Hz, 1H), 6.72-6.67 (m, 2H), 6.50 (d, J=2.4 Hz, 1H), 6.37-6.30 (m, 2H), 5.90 (s, 2H), 3.97 (t, J=6.3 Hz, 2H), 3.80 (d, J=11.9 Hz, 1H), 3.21 (t, J=10.7 Hz, 1H), 3.08-3.07 (m, 2H), 3.02-2.89 (m, 2H), 2.82 (dd, J=15.3, 11.0 Hz, 1H), 2.59 (t, J=7.4 Hz, 2H), 2.37 (t, J=11.7 Hz, 1H), 2.14 (t, J=10.8 Hz, 1H), 2.05-1.96 (m, 2H). $^{13}C$ NMR (201 MHz, DMSO-$d_6$) δ 154.09, 147.91, 141.95, 141.01, 134.01, 122.96, 117.85, 115.54, 108.02, 107.65, 105.72, 102.05, 100.92, 97.99, 97.82, 66.64, 59.54, 56.05, 54.40, 52.50, 45.91, 27.09, 26.22. HR-MS (ESI, m/z): $C_{23}H_{26}N_3O_3^+$ [M+H]$^+$, calculated: 392.1969; found: 392.1970.

Example 10: 3-(4-(2-(4,6,6a,7,9,10-hexahydro-8H-pyrazino[1,2-a]pyrrolo[4,3,2-de]quinolin-8-yl)ethyl) trans-cyclohexyl)-1,1-dimethylurea (Compound I-10)

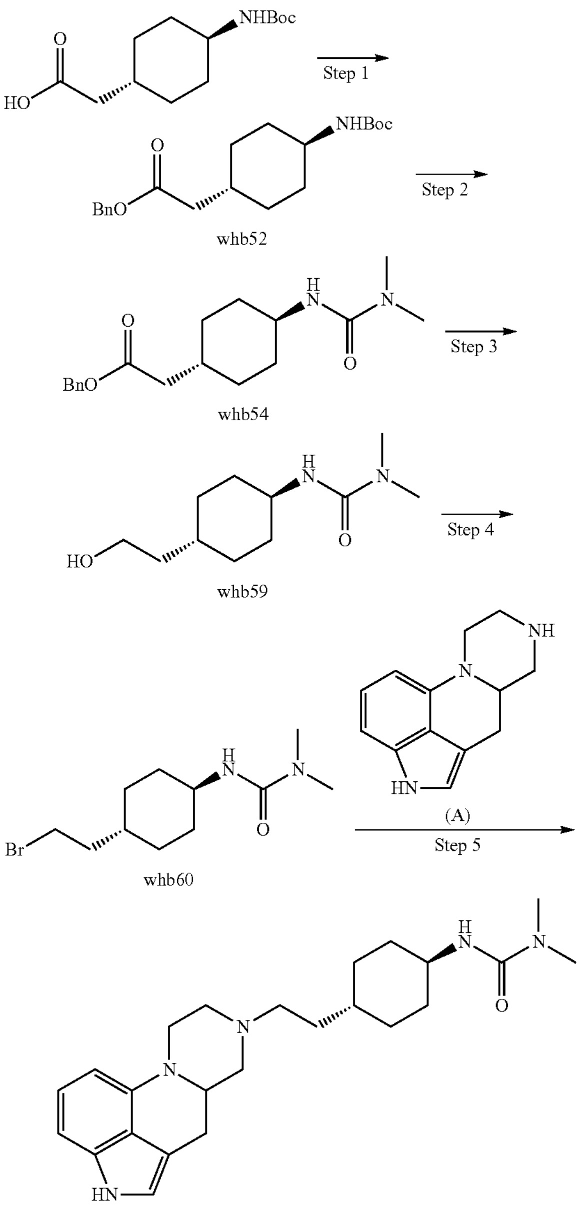

whb52 whb54 whb59

(A)

whb60

I-10

Step 1: 2-(4-((tert-butoxycarbonyl)amino)trans-cyclohexyl)acetic acid (2.0 g, 7.77 mmol) and solvent DMF (15 mL) were added to a round-bottomed flask, and then $Cs_2CO_3$ (7.6 g, 23.3 mmol) and benzyl bromide BnBr (5.32 g, 11.7 mmol) were successively added, and stirred overnight at room temperature. After the reaction was completed, the reaction was filtered, the filtrate was concentrated and the residue was purified by column chromatography (eluent:

dichloromethane containing 0-20% methanol) to obtain the compound whb52 of interest (2.36 g, yield 87%) as a white solid. $^1$H NMR (800 MHz, $CDCl_3$) δ 7.39-7.30 (m, 5H), 5.11 (s, 2H), 4.36 (s, 1H), 3.36 (s, 1H), 2.24 (d, J=6.7 Hz, 2H), 2.00-1.96 (m, 2H), 1.79-1.72 (m, 3H), 1.43 (s, 9H), 1.14-1.04 (m, 4H). HR-MS (ESI, m/z): $C_{20}H_{29}NO_4Na^+$ [M+Na]$^+$, calculated: 370.1989; found: 370.1989 (M+Na$^+$).

Step 2: whb52 (0.16 g, 0.46 mmol) from the previous step was dissolved in dichloromethane (3 mL), and trifluoroacetic acid (1.5 mL) was added and stirred at room temperature for 3 hours. The resulting mixture was concentrated under reduced pressure, the residue was dissolved in THF (5 mL), and then $Et_3N$ (1 mL) and dimethylcarbamoyl chloride (54 mg, 0.5 mmol) were successively added. The reaction system was stirred overnight at room temperature. After the reaction was completed, the solvent was removed and the residue was purified by silica gel column chromatography (eluent: dichloromethane containing 0-20% methanol) to obtain the compound whb54 of interest (0.78 g, 83%) as a white solid. $^1$H NMR (800 MHz, $CDCl_3$) δ 7.38-7.30 (m, 5H), 5.11 (s, 2H), 3.60-3.55 (m, 1H), 2.88 (s, 6H), 2.26 (d, J=6.7 Hz, 2H), 2.04-1.99 (m, 2H), 1.80-1.76 (m, 3H), 1.17-1.09 (m, 4H). $^{13}$C NMR (151 MHz, $CDCl_3$) δ172.80, 157.86, 136.07, 128.59, 128.23, 128.19, 66.12, 49.49, 41.47, 36.19, 34.23, 33.69, 31.76. HR-MS (ESI, m/z): $C_{18}H_{27}N_2O_3^+$ [M+H]$^+$, calculated: 319.2016; found: 319.2201.

Step 3: whb54 (0.78 g, 2.45 mmol) was dissolved in THF (20 mL), and cooled down to −10° C. under the protection of argon (Ar). Then DABAL-H (14.7 mL, 1 M) was added. Then the reaction system was further stirred at 0° C. for 5 hours. After the reaction was completed, the reaction was quenched with saturated sodium potassium tartrate solution (5 mL). After removal of the solvent, the residue was purified by silica gel column chromatography (eluent: dichloromethane containing 0-20% methanol) to give whb59 (0.50 g, yield 95%) as a white solid. $^1$H NMR (600 MHz, $CDCl_3$) δ 4.27 (d, J=7.7 Hz, 1H), 3.65 (t, J=6.7 Hz, 2H), 3.59-3.52 (m, 1H), 2.88 (s, 6H), 2.00 (d, J=10.6 Hz, 2H), 1.81-1.75 (m, 2H), 1.49-1.46 (m, 2H), 1.40-1.34 (m, 1H), 1.15-1.01 (m, 4H). HR-MS (ESI, m/z): $C_{11}H_{23}N_2O_2^+$ [M+H]$^+$, calculated: 215.1754; found: 215.1983.

Step 4: whb59 (0.65 g, 3.04 mmol) and $CBr_4$ (1.5 g, 4.56 mmol) were dissolved in dichloromethane (15 mL), cooled and stirred under an ice-water bath. $PPh_3$ (1.2 g, 4.56 mmol) was added, then moved to room temperature and stirred for 4 hours. The solvent was evaporated under reduced pressure, and the residue was purified by silica gel column chromatography (mobile phase: dichloromethane containing 0-3% methanol) to obtain whb60 (0.25 g, 38%) as a white solid. $^1$H NMR (800 MHz, $CDCl_3$) δ 4.16-4.00 (m, 1H), 3.61-3.57 (m, 1H), 3.43 (t, J=7.0 Hz, 1H), 2.88 (s, 6H), 2.03 (d, J=10.0, Hz, 2H), 1.80-1.74 (m, 4H), 1.47-1.43 (m, 1H), 1.14-1.03 (m, 4H). HR-MS (ESI, m/z): $C_{11}H_{22}BrN_2O^+$ [M+H]$^+$, calculated: 277.0910; found: 277.0924 and 279.0925.

Step 5: The experimental method was the same as step 2 of example 1, and whb60 and the starting material (A) were subjected to alkylation reaction to prepare compound I-10 (0.18 g, 95%) as an off-white solid. $^1$H NMR (800 MHz, $CDCl_3$) δ 7.93 (s, 1H), 7.07 (t, J=7.8 Hz, 1H), 6.79 (d, J=8.1 Hz, 1H), 6.72 (t, J=1.7 Hz, 1H), 6.33 (d, J=7.6 Hz, 1H), 4.12 (d, J=7.6 Hz, 1H), 3.79 (d, J=11.7, 2.7 Hz, 1H), 3.61-3.56 (m, 1H), 3.21 (s, 1H), 3.07 (d, J=10.2 Hz, 2H), 2.97 (dd, J=15.2, 3.7 Hz, 1H), 2.93 (t, J=11.8 Hz, 1H), 2.88 (s, 6H), 2.84-2.78 (m, 1H), 2.43 (t, J=7.9 Hz, 2H), 2.32 (t, J=10.9 Hz, 1H), 2.09 (t, J=10.8 Hz, 1H), 2.04-1.99 (m, 2H), 1.81-1.75 (m, 2H), 1.49-1.46 (m, 2H), 1.29-1.24 (m, 1H), 1.14-1.04

(m, 3H). $^{13}C$ NMR (201 MHz, $CDCl_3$) δ157.97, 142.19, 134.40, 123.92, 118.14, 115.13, 109.19, 102.14, 98.90, 65.92, 60.19, 56.70, 56.18, 53.11, 49.93, 46.26, 40.99, 36.22, 35.70, 34.05, 33.80, 32.14, 27.70, 15.34. HR-MS (ESI, m/z): $C_{24}H_{36}N_5O^+$ $[M+H]^+$, calculated: 410.2914, found: 410.2914.

Chiral Resolution of Compound I-10

Chiral analysis conditions: chiral column CHIRALPAK IG (Dacel), column volume: 0.46 cm (diameter)×15 cm (column length) (5 μm particle size filler); mobile phase: methanol/acetonitrile/diethylamine=80/20/0.1 (V/V/V); flow rate: 1.0 mL/min; wavelength: UV 210 nm; temperature: 25° C.; HPLC instrument: Shimadzu LC-2010 BJ. Peak 1 (prepeak) $t_R$=3.113 min; peak 2 (postpeak): $t_R$=4.622 min.

Chiral preparation conditions: chiral column CHIRALPAK IG (Dacel), column volume: 2.5 cm (diameter)×25 cm (column length) (10 μm particle size filler); mobile phase: methanol/acetonitrile/diethylamine=80/20/0.1 (V/V/V); flow rate: 1.0 mL/min; wavelength: UV 210 nm; temperature: 25° C.; HPLC instrument: Shimadzu LC-2010 BJ. Peak 1 (prepeak) $t_R$=3.113 min; peak 2 (postpeak): $t_R$=4.622 min.

Chiral resolution: racemate compound I-10 (1.20 g), (−)-I-10 is the prepeak (peak 1), $t_R$=3.057 min, 0.566 g obtained, >99% ee, optical rotation $[\alpha]_D^{25}$=−56.67° (c=0.1, $CHCl_3$); (+)-I-10 is the postpeak (peak 2), $t_R$=4.512 min, 0.599 g obtained, >99% ee, optical rotation $[\alpha]_D^{25}$=+50.33° (c=0.1, $CHCl_3$).

Synthesis of pNs-(+)-I-10 and Determination of its Chiral Configuration:

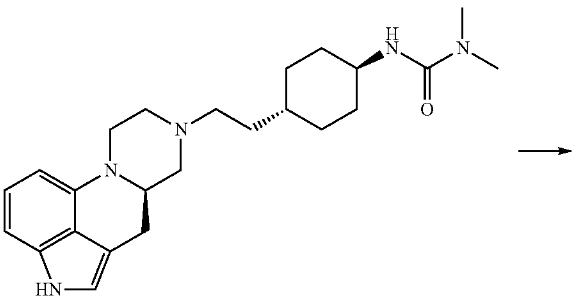

(+)-I-10

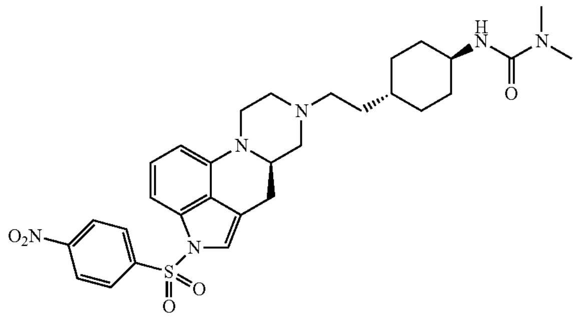

pNs-(+)-I-10

Step: (+)-I-10 (23 mg, 0.056 mmol) was dissolved in DMF (3 mL), then potassium tert-butoxide (13 mg, 0.116 mmol) and p-nitrobenzenesulfonyl chloride (14 mg, 0.063 mmol) were successively added, and the reaction liquid was stirred at room temperature for one hour. After the reaction was completed, water was added, and then extracted three times with dichloromethane solvent, and the organic phases were combined and concentrated. The crude product obtained by concentration was purified by flash silica gel column chromatography (eluent: 0-10% methanol/dichloromethane) to obtain pNs-(+)-I-10 (20 mg, yield 60%) as an orange-yellow solid. $^1H$ NMR (800 MHz, $CDCl_3$) δ 8.27-8.23 (m, 2H), 8.05-8.01 (m, 2H), 7.32 (d, J=8.2 Hz, 1H), 7.22 (t, J=8.0 Hz, 1H), 7.01 (d, J=1.9 Hz, 1H), 6.50 (d, J=7.9 Hz, 1H), 4.10 (d, J=7.6 Hz, 1H), 3.71-3.68 (m, 1H), 3.60-3.55 (m, 1H), 3.16-3.12 (m, 1H), 3.07-3.04 (m, 2H), 2.90-2.88 (m, 7H), 2.69-2.65 (m, 1H), 2.44-2.40 (m, 2H), 2.28-2.25 (m, 1H), 2.11-1.96 (m, 3H), 1.78-1.75 (m, 2H), 1.47-1.42 (m, 2H), 1.33-1.27 (m, 1H), 1.13-1.03 (m, 4H). HR-MS (ESI, m/z): $C_{30}H_{39}N_6O_5S^+$ $[M+H]^+$, calculated: 595.2697; found: 595.2663. Optical rotation $[\alpha]_D^{25}$=+47.67° (c=0.1, $CDCl_3$).

Single Crystal Preparation of the Compound as Shown in Formula pNs-(+)-I-10

Single crystal growth by volatilization method: 10 mg of compound pNs-(+)-I-10 was weighed in 1 mL of chloroform, and then 10 mL of petroleum ether was added. The test tube was placed at room temperature for slow volatilization for crystallization.

Detection Method X-Ray Single Crystal Diffraction

After detection, the crystal system of the compound as shown in the formula pNs-(+)-I-10 belonged to the triclinic crystal system, the P1 space group, and the unit cell parameters were a=9.315 Å, b=6.564 Å, c=23.792 Å, α=90.15°, β=99.368°, γ=90.25°, the number of asymmetric unit Z in the unit cell was 2; the X-ray single crystal diffraction is shown in FIG. 1.

The characterization results of X-ray single crystal diffraction can determine that the configuration of compound pNs-(+)-I-10 is

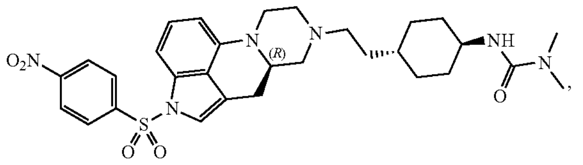

thus it can be deduced that the configuration of (+)-I-10 compound is

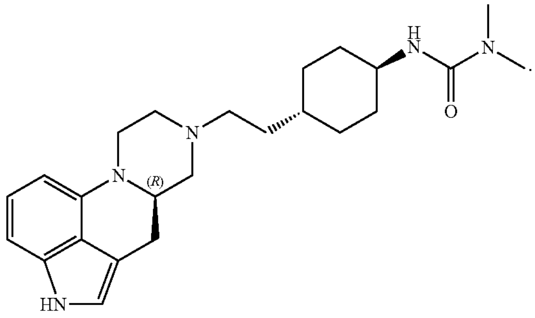

Correspondingly, the configuration of compound (−)-I-10 is

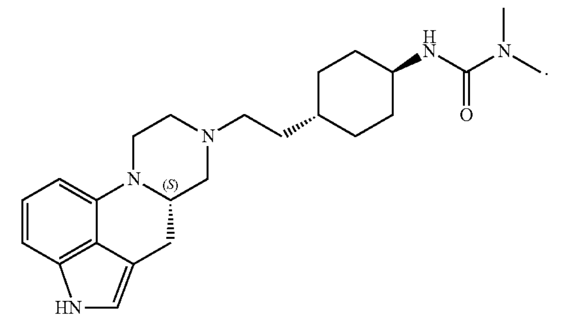

Example 11: N-(4-(2-(4,6,6a,7,9,10-hexahydro-8H-pyrazino[1,2-a]pyrrolo[4,3,2-de]quinolin-8-yl)ethyl) trans-cyclohexyl)tetrahydropyrrole-1-carboxamide (Compound I-11)

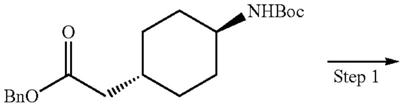

whb52

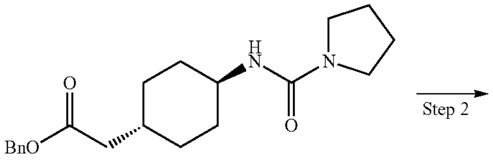

whb77

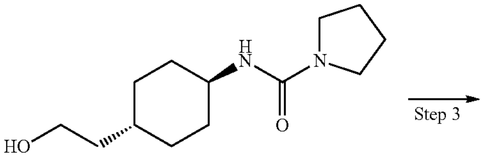

whb81

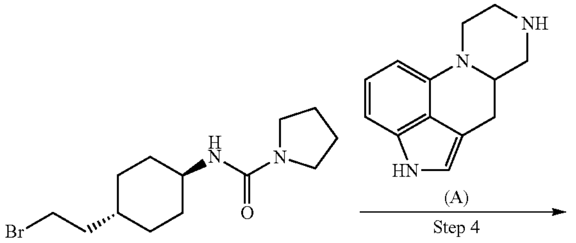

whb87

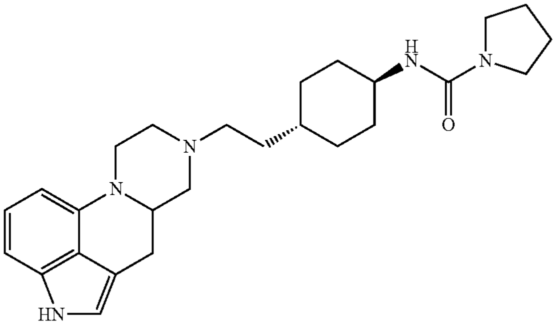

I-11

Step 1: Using whb52 as a raw material, following the method of step 2 of example 10 and replacing "dimethylcarbamoyl chloride" with "tetrahydropyrrole-1-formyl chloride", the intermediate whb77 (0.54 g, 87%) was prepared as a white solid. $^1$H NMR (800 MHz, $CDCl_3$) δ 7.39-7.30 (m, 5H), 5.11 (s, 2H), 3.95 (br, 1H), 3.61-3.56 (m, 1H), 3.31-3.29 (m, 4H), 2.25 (d, J=6.8 Hz, 2H), 2.06-2.00 (m, 2H), 1.91-1.87 (m, 4H), 1.65-1.59 (m, 2H), 1.17-1.07 (m, 4H).

Step 2: Following the method of step 3 of example 10, whb77 was converted to whb81 (0.36 g, 96%) as a white solid. $^1$H NMR (800 MHz, $CDCl_3$) δ 3.69 (t, J=6.7 Hz, 2H), 3.63-3.59 (m, 1H), 3.34-3.32 (d, J=6.4 Hz, 4H), 2.06-2.01 (m, 2H), 1.93-1.88 (m, 4H), 1.82-1.77 (m, 2H), 1.50-1.47 (m, 2H), 1.40-1.36 (m, 1H), 1.15-1.05 (m, 4H). HR-MS (ESI, m/z): $C_{13}H_{25}N_2O_2^+$ $[M+H]^+$, calculated: 241.1911; found: 241.1945.

Step 3: Following the method of step 4 of example 10, the intermediate whb81 was converted into whb87 (0.34 g, yield 76%) as a white solid. $^1$H NMR (600 MHz, $CDCl_3$) δ 3.99-3.93 (m, 1H), 3.63-3.58 (m, 1H), 3.44 (t, J=7.0 Hz, 2H), 3.32-3.29 (m, 4H), 2.08-2.01 (m, 2H), 1.93-1.85 (m, 3H), 1.83-1.73 (m, 4H), 1.50-1.40 (m, 1H), 1.17-1.02 (m, 4H). HR-MS (ESI, m/z): $C_{13}H_{24}BrN_2O^+$ $[M+H]^+$, calculated: 303.1067; found: 303.1073 and 305.1080.

Step 4: Following the method of step 5 of example 10, whb87 and the starting material (A) were subjected to alkylation reaction to obtain compound I-11 (50 mg, 50%) as an off-white solid. $^1$H NMR (800 MHz, $CDCl_3$) δ 7.97 (d, J=4.7 Hz, 1H), 7.07 (t, J=7.8 Hz, 1H), 6.79 (d, J=8.1 Hz, 1H), 6.72 (d, J=1.8 Hz, 1H), 6.33 (d, J=7.6 Hz, 1H), 3.95 (d, J=7.8 Hz, 1H), 3.79 (d, J=11.9 Hz, 1H), 3.63-3.58 (m, 1H), 3.32-3.29 (m, 4H), 3.22 (t, J=10.24 Hz, 1H), 3.10-3.06 (m, 2H), 2.98 (dd, J=15.3, 3.8 Hz, 1H), 2.94 (d, J=11.9 Hz, 1H), 2.82 (dd, J=15.3, 10.9 Hz, 1H), 2.44 (t, J=7.9 Hz, 2H), 2.36-2.30 (m, 1H), 2.10 (t, J=10.8 Hz, 1H), 2.05-2.01 (m, 2H), 1.92-1.85 (m, 3H), 1.80-1.75 (m, 2H), 1.51-1.44 (m, 2H), 1.29-1.24 (m, 1H), 1.13-1.05 (m, 4H). $^{13}$C NMR (201 MHz, $CDCl_3$) δ156.13, 141.91, 134.14, 123.77, 117.87, 114.85, 114.83, 109.04, 101.83, 98.74, 98.72, 59.86, 56.45, 55.87, 52.82, 49.30, 45.97, 45.29, 35.45, 33.93, 33.52, 31.91, 27.42, 25.37. HR-MS (ESI, m/z): $C_{26}H_{38}N_5O^+$ $[M+H]^+$, calculated: 436.3071; found: 436.3072.

Example 12: N-(4-(2-(4,6,6a,7,9,10-hexahydro-8H-pyrazino[1,2-a]pyrrolo[4,3,2-de]quinolin-8-yl)ethyl) trans-cyclohexyl)piperidine-1-carboxamide (Compound I-12)

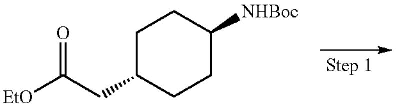

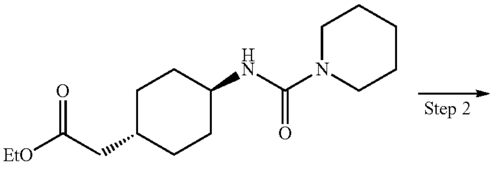

whb80

-continued

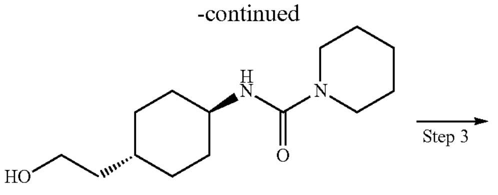

whb86

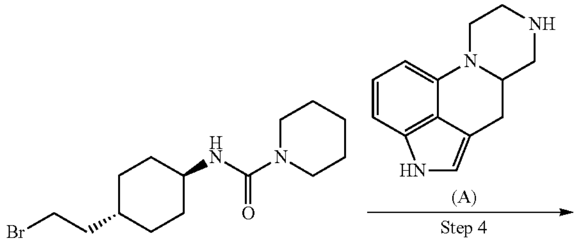

whb87

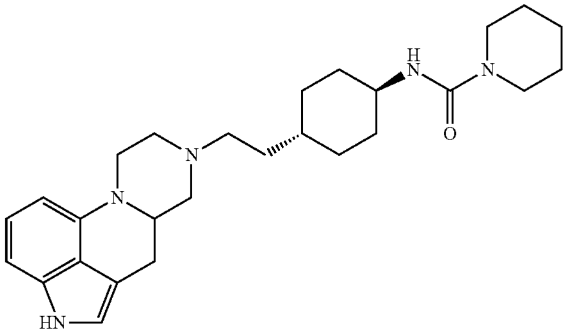

I-12

Step 1: Following the method of step 2 of example 10 and replacing “dimethylcarbamoyl chloride” with “piperidine-1-formyl chloride”, the intermediate whb80 was prepared as a white solid. $^1$H NMR (800 MHz, $CDCl_3$) δ 4.28-4.17 (m, 1H), 4.12 (q, J=7.1 Hz, 2H), 3.62-3.56 (m, 1H), 3.31-3.27 (m, 4H), 2.19 (d, J=7.0 Hz, 2H), 2.02 (m, 2H), 1.80-1.77 (m, 2H), 1.59-1.57 (m, 2H), 1.56-1.53 (m, 4H), 1.25 (t, J=7.1 Hz, 3H), 1.15-1.08 (m, 4H). HR-MS (ESI, m/z): $C_{16}H_{29}N_2O_3^+$ [M+H]$^+$, calculated: 297.2173; found: 297.2373.

Step 2: Following the method of step 3 of example 11, whb80 was converted to whb86 as a white solid. $^1$H NMR (800 MHz, $CDCl_3$) δ 4.27 (s, 1H), 3.69 (t, J=6.6 Hz, 2H), 3.59 (s, 1H), 3.31-3.27 (m, 4H), 2.02 (dd, J=7.0, 3.7 Hz, 2H), 1.81-1.75 (m, 2H), 1.59-1.53 (m, 6H), 1.48 (q, J=6.7 Hz, 2H), 1.40-1.36 (m, 1H), 1.12-1.04 (m, 4H). HR-MS (ESI, m/z): $C_{14}H_{27}N_2O_2^+$ [M+H]$^+$, calculated: 255.2067; found: 255.2057.

Step 3: Following the method of step 4 of example 10, the intermediate whb86 was converted into whb89 (yield 80%) as a white solid. $^1$H NMR (600 MHz, $CDCl_3$) δ 4.25 (s, 1H), 3.59 (s, 1H), 3.44 (t, J=7.0 Hz, 2H), 3.32-3.27 (m, 4H), 2.04-2.02 (m, 2H), 1.78-1.75 (m, 4H), 1.62-1.50 (m, 5H), 1.48-1.43 (m, 1H), 1.17-1.00 (m, 4H). HR-MS (ESI, m/z): $C_{14}H_{26}BrN_2O^+$ [M+H]$^+$, calculated: 317.1223; found: 317.1260 and 319.1141.

Step 4: Following the method of step 5 of example 10, whb89 and the starting material (A) were subjected to alkylation reaction to obtain compound I-12 (62 mg, 98%) as a white solid. $^1$H NMR (800 MHz, $CDCl_3$) δ 7.91 (s, 1H), 7.07 (t, J=7.8 Hz, 1H), 6.80 (d, J=8.1 Hz, 1H), 6.72 (t, J=1.8 Hz, 1H), 6.33 (d, J=7.6 Hz, 1H), 4.20 (d, J=7.5 Hz, 1H), 3.79 (d, J=11.9 Hz, 1H), 3.61-3.57 (m, 1H), 3.29 (t, J=5.5 Hz, 4H), 3.22 (s, 1H), 3.07 (d, J=10.9 Hz, 2H), 2.98 (dd, J=15.2, 3.8 Hz, 1H), 2.94 (d, J=12.0 Hz, 1H), 2.82 (dd, J=15.3, 11.0 Hz, 1H), 2.44 (t, J=8.0 Hz, 2H), 2.33 (t, J=11.6 Hz, 1H), 2.09 (t, J=10.8 Hz, 1H), 2.04-1.99 (m, 2H), 1.79 (d, J=12.3 Hz, 2H), 1.61-1.54 (m, 5H), 1.49-1.46 (m, 2H), 1.29-1.23 (m, 1H), 1.14-1.03 (m, 4H). $^{13}$C NMR (201 MHz, $CDCl_3$) δ 156.97, 141.98, 134.13, 123.79, 117.86, 114.77, 109.13, 101.78, 98.74, 65.67, 59.95, 56.46, 55.91, 52.87, 49.61, 49.50, 46.01, 44.66, 40.82, 35.49, 33.77, 33.60, 31.90, 27.43, 25.39, 24.25. HR-MS (ESI, m/z): $C_{27}H_{40}N_5O^+$ [M+H]$^+$, calculated: 450.3227; found: 450.3227.

Example 13: N-(4-(2-(4,6,6a,7,9,10-hexahydro-8H-pyrazino[1,2-a]pyrrolo[4,3,2-de]quinolin-8-yl)ethyl) trans-cyclohexyl)-1H-indole-2-carboxamide (Compound I-13)

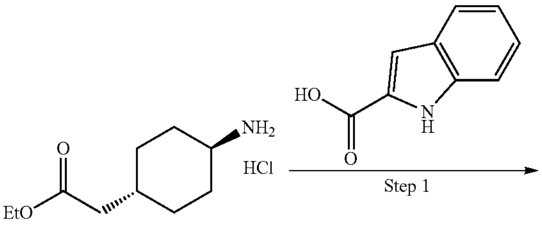

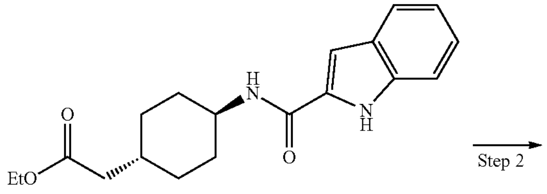

whb108

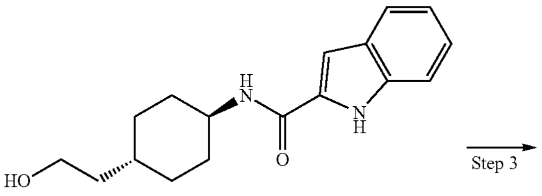

whb149

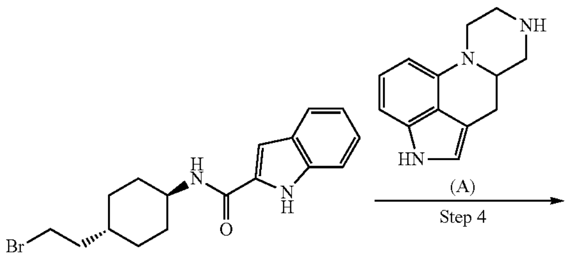

whb150

-continued

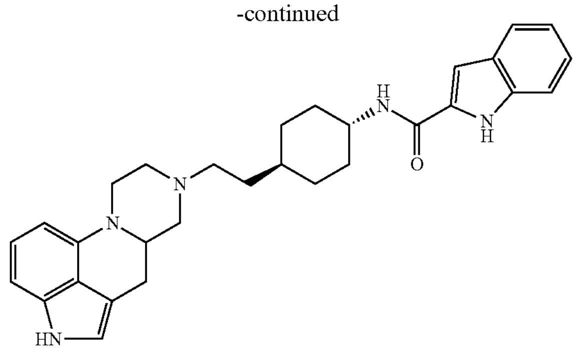

I-13

Step 1: methyl 2-(4-aminotrans-cyclohexyl)acetate (0.19 g, 1.02 mmol) was dissolved in tetrahydrofuran (5 mL) in a round bottom flask, then HATU (0.505 g, 1.33 mmol), DIPEA (1 mL) and 1H-indole-2-carboxylic acid (0.214 g, 1.33 mmol) were added, and the reaction system was stirred overnight at room temperature. The solvent was evaporated under reduced pressure, and the residue was purified by silica gel column chromatography (eluent: petroleum ether containing 40-50% ethyl acetate) to obtain intermediate whb108 (0.30 g, 90%) as a white solid. $^1$H NMR (800 MHz, $CDCl_3$) δ 9.41 (d, J=62.1 Hz, 1H), 7.64 (d, J=8.0 Hz, 1H), 7.43 (d, J=8.2 Hz, 1H), 7.28 (d, J=8.3 Hz, 1H), 7.13 (t, J=7.4 Hz, 1H), 6.85 (d, J=4.9 Hz, 1H), 6.16 (d, J=33.4 Hz, 1H), 4.14 (q, J=7.1 Hz, 2H), 3.98-3.93 (m, 1H), 2.24 (dd, J=13.8, 7.0 Hz, 2H), 2.12 (d, J=13.4 Hz, 2H), 1.86 (d, J=13.4 Hz, 2H), 1.83-1.79 (m, 1H), 1.31 (q, J=12.8 Hz, 2H), 1.26 (t, J=7.2 Hz, 3H), 1.21-1.17 (q, J=12.8 Hz, 2H). HR-MS (ESI, m/z): $C_{19}H_{25}N_2O_3^+$ [M+H]$^+$, calculated: 329.1860; found: 329.1795.

Step 2: Following the method described in step 3 of example 10, the intermediate whb108 was reduced to obtain intermediate whb149 (80 mg, 47%) as a white solid. $^1$H NMR (800 MHz, $CDCl_3$) δ 9.23 (s, 1H), 7.64 (d, J=8.0 Hz, 1H), 7.43 (d, J=8.3 Hz, 1H), 7.28 (t, J=8.2 Hz, 1H), 7.14 (t, J=7.8 Hz, 1H), 6.82-6.79 (m, 1H), 3.97-3.93 (m, 1H), 3.72 (t, J=6.6 Hz, 2H), 2.15-2.10 (m, 2H), 1.89-1.83 (m, 2H), 1.54-1.51 (m, 2H), 1.49-1.43 (m, 1H), 1.31-1.23 (m, 2H), 1.18-1.13 (m, 2H). HR-MS (ESI, m/z): $C_{17}H_{23}N_2O_2^+$ [M+H]$^+$, calculated: 287.1754; found: 287.1752.

Step 3: Following the method of step 4 of example 10, the alcohol intermediate whb149 was converted into bromide whb150 (0.11 g, 45%) as a white solid. $^1$H NMR (800 MHz, $CDCl_3$) δ 9.31 (s, 1H), 7.64 (d, J=8.0 Hz, 1H), 7.43 (d, J=8.4 Hz, 1H), 7.31-7.27 (m, 1H), 7.13 (t, J=7.12 Hz, 1H), 6.84 (d, J=2.2 Hz, 1H), 6.10 (d, J=8.2 Hz, 1H), 3.97-3.91 (m, 1H), 3.46 (t, J=7.0 Hz, 2H), 2.13 (d, J=13.4 Hz, 2H), 1.88-1.83 (m, 2H), 1.81 (q, J=6.9 Hz, 2H), 1.55-1.51 (m, 1H), 1.33-1.29 (m, 2H), 1.16-1.11 (m, 2H). HR-MS (ESI, m/z): $C_{17}H_{22}BrN_2O^+$ [M+H]$^+$, calculated: 349.0910; found: 349.0901 and 351.0884.

Step 4: Following the method of step 5 of example 10, whb150 and the starting material (A) were subjected to alkylation reaction to obtain compound I-13 (33 mg, yield 30%) as a white solid. $^1$H NMR (800 MHz, $CDCl_3$) δ 9.16 (s, 1H), 7.83 (s, 1H), 7.64 (dd, J=8.0, 1.1 Hz, 1H), 7.43 (dd, J=8.3, 1.1 Hz, 1H), 7.28 (dd, J=8.2, 7.0 Hz, 1H), 7.14 (dd, J=8.0, 7.0 Hz, 1H), 7.08 (t, J=7.8 Hz, 1H), 6.82-6.79 (m, 2H), 6.73 (d, J=1.9 Hz, 1H), 6.34 (d, J=7.6 Hz, 1H), 5.95 (d, J=8.2 Hz, 1H), 3.97-3.93 (m, 1H), 3.82-3.78 (m, 1H), 3.21 (s, 1H), 3.08 (d, J=10.8 Hz, 2H), 2.98 (dd, J=15.2, 3.8 Hz, 1H), 2.94 (t, J=11.8 Hz, 1H), 2.83 (dd, J=15.2, 11.1 Hz, 1H), 2.46 (t, J=7.9 Hz, 2H), 2.35-2.30 (m, 1H), 2.16-2.06 (m, 3H), 1.87 (d, J=11.96 Hz, 2H), 1.52-1.50 (m, 2H), 1.36-1.32 (m, 1H), 1.29-1.24 (m, 2H), 1.20-1.14 (m, 2H). $^{13}$C NMR (201 MHz, DMSO-$d_6$) δ 160.22, 141.98, 136.35, 134.02, 132.02, 127.10, 123.11, 122.97, 121.39, 119.61, 117.86, 115.54, 112.26, 107.69, 102.46, 102.05, 98.00, 59.62, 56.07, 55.75, 52.55, 48.21, 45.92, 34.90, 33.46, 32.35, 31.74, 27.12. HR-MS (ESI, m/z): $C_{30}H_{36}N_5O^+$ [M+H]$^+$, calculated: 482.2914; found: 482.2918.

Example 14: N-(4-(2-(4,6,6a,7,9,10-hexahydro-8H-pyrazino[1,2-a]pyrrolo[4,3,2-de]quinolin-8-yl)ethyl) trans-cyclohexyl)benzamide (Compound I-14)

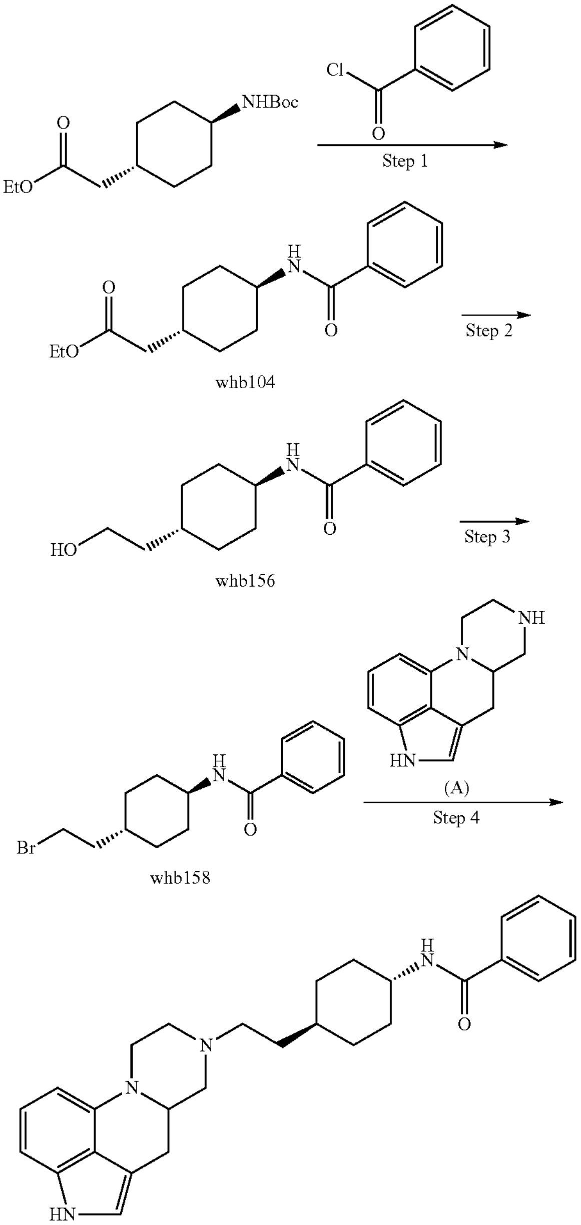

I-14

Step 1: Using "ethyl 2-(4-((tert-butoxycarbonylamino-trans-cyclohexyl) acetate" as a raw material, following the method of step 2 of example 10 and replacing "dimethylcarbamoyl chloride" with "benzoyl chloride", intermediate whb104 (0.20 g, yield 69%) was obtained as a white solid. $^1$H NMR (800 MHz, $CDCl_3$) δ 7.74 (d, J=7.6 Hz, 2H), 7.49 (t, J=7.4 Hz, 1H), 7.42 (t, J=7.5 Hz, 2H), 5.95-5.91 (br, 1H), 4.14 (q, J=7.1 Hz, 2H), 3.96-3.91 (m, 1H), 2.23 (dd, J=13.9, 7.0 Hz, 2H), 2.11 (d, J=12.2 Hz, 2H), 1.85 (d, J=13.3 Hz, 2H), 1.82-1.77 (m, 1H), 1.30-1.23 (m, 5H), 1.21-1.16 (m, 2H). HR-MS (ESI, m/z): $C_{17}H_{24}NO_3^+$ $[M+H]^+$, calculated: 290.1751; found: 290.1748 and 312.1526 ($M+Na^+$).

Step 2: Following the method described in step 3 of example 10, the intermediate whb104 was reduced to obtain intermediate whb156 (0.11 g, yield 65%) as a white solid. $^1$H NMR (800 MHz, $CDCl_3$) δ 7.77-7.73 (m, 2H), 7.51-7.46 (m, 1H), 7.45-7.40 (m, 2H), 5.89 (d, J=8.1 Hz, 1H), 3.96-3.91 (m, 1H), 3.71 (t, J=6.8 Hz, 2H), 2.14-2.09 (m, 2H), 1.87-1.83 (m, 2H), 1.53-1.50 (m, 2H), 1.47-1.42 (m, 1H), 1.28-1.20 (m, 2H), 1.18-1.11 (m, 2H). HR-MS (ESI, m/z): $C_{15}H_{22}NO_2^+$ $[M+H]^+$, calculated: 248.1645; found: 248.1772.

Step 3: Following the method of step 4 of example 10, the alcohol intermediate whb156 was converted into bromide whb158 (78 mg, 57%) as a white solid. $^1$H NMR (800 MHz, $CDCl_3$) δ 7.76-7.73 (m, 2H), 7.51-7.47 (m, 1H), 7.43 (dd, J=8.3, 7.1 Hz, 2H), 5.89 (d, J=8.1 Hz, 1H), 3.97-3.90 (m, 1H), 3.46 (t, J=7.0 Hz, 2H), 2.13 (d, J=13.2 Hz, 2H), 1.87-1.82 (m, 2H), 1.81-1.79 (m, 2H), 1.54-1.48 (m, 1H), 1.27-1.22 (m, 2H), 1.16-1.11 (m, 2H). HR-MS (ESI, m/z): $C_{15}H_{21}BrNO^+$ $[M+H]^+$, calculated: 310.0801; found: 310.0792 and 312.0772.

Step 4: Following the method of step 5 of example 10, the whb158 and the starting material (A) were subjected to alkylation reaction to obtain compound I-14 (30 mg, yield 32%) as a yellow solid. $^1$H NMR (800 MHz, $CDCl_3$) δ 7.84 (s, 1H), 7.76-7.73 (m, 2H), 7.52-7.46 (m, 1H), 7.43 (dd, J=8.3, 7.1 Hz, 2H), 7.08 (t, J=7.8 Hz, 1H), 6.80 (d, J=8.1 Hz, 1H), 6.73 (d, J=1.9 Hz, 1H), 6.34 (d, J=7.5 Hz, 1H), 5.89 (d, J=8.1 Hz, 1H), 3.97-3.92 (m, 1H), 3.81 (d, J=11.7 Hz, 1H), 3.25-3.21 (m, 1H), 3.08 (d, J=10.9 Hz, 2H), 2.99-2.93 (m, 2H), 2.83 (dd, J=15.3, 11.0 Hz, 1H), 2.48-2.44 (s, 2H), 2.36-2.32 (m, 1H), 2.12 (dd, J=12.1, 3.8 Hz, 3H), 1.85 (d, J=12.8 Hz, 2H), 1.53-1.50 (m, 2H), 1.37-1.30 (m, 1H), 1.26-1.13 (m, 4H). $^{13}$C NMR (201 MHz, DMSO-$d_6$) δ 165.87, 142.44, 135.36, 134.48, 131.38, 128.59, 127.71, 123.43, 118.32, 116.02, 108.13, 102.53, 98.47, 56.51, 56.20, 53.01, 49.04, 46.36, 40.91, 35.37, 33.88, 32.65, 32.23, 27.58. HR-MS (ESI, m/z): $C_{28}H_{35}N_4O^+$ $[M+H]^+$, calculated: 443.2805; found: 443.2807.

Example 15: N-(4-(2-(4,6,6a,7,9,10-hexahydro-8H-pyrazino[1,2-a]pyrrolo[4,3,2-de]quinolin-8-yl)ethyl)cyclohexyl)phenylsulfonamide (Compound I-15)

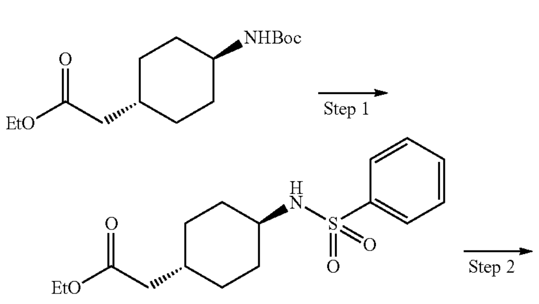

whb105

-continued

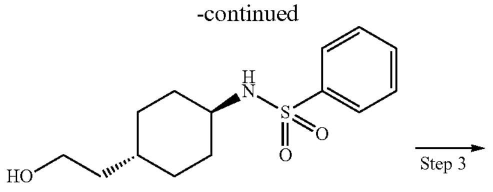

whb155

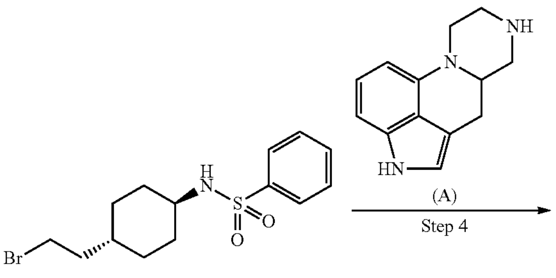

whb159

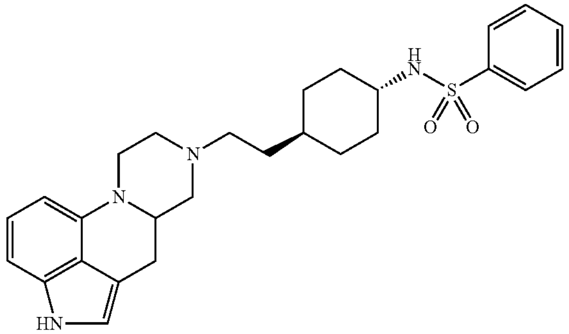

I-15

Step 1: Using "ethyl 2-(4-((tert-butoxycarbonylamino-trans-cyclohexyl) acetate" as a raw material, following the method of step 2 of example 10 and replacing "dimethylcarbamoyl chloride" with "benzenesulfonyl chloride", intermediate whb105 (0.30 g, yield 89%) was obtained as a white solid. $^1$H NMR (800 MHz, $CDCl_3$) δ 7.88 (d, J=7.7 Hz, 2H), 7.57 (t, J=7.4 Hz, 1H), 7.51 (t, J=7.6 Hz, 2H), 4.51 (br, 1H), 4.09 (q, J=7.1 Hz, 2H), 3.1-3.07 (m, 1H), 2.14 (dd, J=14.4, 6.9 Hz, 2H), 1.83 (d, J=13.3 Hz, 2H), 1.72 (d, J=13.6 Hz, 2H), 1.69-1.65 (m, 1H), 1.23 (t, J=7.1 Hz, 3H), 1.20-1.15 (m, 2H), 1.00-0.96 (m, 2H). HR-MS (ESI, m/z): $[C_{16}H_{23}NO_4S+Na]^+$ $[M+Na]^+$, calculated: 348.1240; found: 348.1245.

Step 2: Following the method described in step 3 of example 10, intermediate whb105 was reduced to obtain intermediate whb155 (0.22 g, 87%) as a white solid. $^1$H NMR (800 MHz, $CDCl_3$) δ 7.90-7.86 (m, 2H), 7.59-7.55 (m, 1H), 7.51 (dd, J=8.4, 7.1 Hz, 2H), 4.34 (s, NH, 1H), 3.64 (t, J=6.6 Hz, 2H), 3.11-3.06 (m, 1H), 1.86-1.82 (m, 2H), 1.72 (d, J=13.2 Hz, 2H), 1.42 (q, J=6.7 Hz, 2H), 1.36-1.28 (m, 1H), 1.16-1.11 (m, 2H), 0.96-0.90 (m, 2H). HR-MS (ESI, m/z): $C_{14}H_{22}NO_3S^+$ $[M+H]^+$, calculated: 284.1315; found: 284.1332.

Step 3: Following the method of step 4 of example 10, the alcohol intermediate whb155 was converted into bromide whb159 (0.10 g, 37%) as a white solid. $^1$H NMR (800 MHz, $CDCl_3$) δ 7.90-7.86 (m, 2H), 7.59-7.55 (m, 1H), 7.53-7.49 (m, 2H), 4.38 (br, 1H), 3.38 (t, J=7.0 Hz, 2H), 3.12-3.07 (m, 1H), 1.88-1.82 (m, 2H), 1.74-1.68 (m, 4H), 1.43-1.35 (m, 1H), 1.19-1.12 (m, 2H), 0.96-0.86 (m, 2H). HR-MS (ESI, m/z): $C_{14}H_{21}BrNO_2S^+$ $[M+H]^+$, calculated: 346.0471; found: 346.0457 and 348.0435.

Step 4: Following the method of step 5 of example 10, the whb159 and the starting material (A) were subjected to alkylation reaction to obtain compound I-15 (40 mg, 98%) as a pale yellow solid. $^{1}$H NMR (800 MHz, $CDCl_3$) δ 7.90-7.86 (m, 2H), 7.83 (s, 1H), 7.59-7.55 (m, 1H), 7.51 (dd, J=8.3, 7.1 Hz, 2H), 7.07 (t, J=7.8 Hz, 1H), 6.80 (d, J=8.1 Hz, 1H), 6.72 (s, 1H), 6.32 (d, J=7.6 Hz, 1H), 4.28 (d, J=7.6 Hz, 1H), 3.80-3.77 (s, 1H), 3.23-3.16 (m, 1H), 3.12-3.08 (m, 1H), 3.06-3.01 (m, 2H), 2.97 (d, J=15.0 Hz, 1H), 2.80 (dd, J=15.3, 10.6 Hz, 1H), 2.43-2.36 (s, 2H), 2.31 (s, 1H), 2.08-2.04 (s, 1H), 1.84 (d, J=12.8 Hz, 3H), 1.73 (d, J=13.4 Hz, 2H), 1.45-1.39 (m, 2H), 1.23-1.19 (m, 1H), 1.17-1.09 (m, 2H), 0.99-0.92 (m, 2H). $^{13}$C NMR (201 MHz, $CDCl_3$) δ142.12, 141.61, 141.59, 134.37, 132.46, 129.10, 126.89, 123.98, 118.12, 115.15, 109.17, 102.19, 99.00, 60.04, 56.50, 56.09, 53.20, 52.98, 46.17, 40.89, 35.08, 33.88, 33.48, 31.90, 27.65. HR-MS (ESI, m/z): $C_{27}H_{35}N_4O_2S^+$ $[M+H]^+$, calculated: 479.2475; found: 479.2487.

Example 16: 3-(4-((4,6,6a,7,9,10-hexahydro-8H-pyrazino[1,2-a]pyrrolo[4,3,2-de]quinolin-8-yl)methyl)trans-cyclohexyl)-1,1-dimethylurea (Compound I-16)

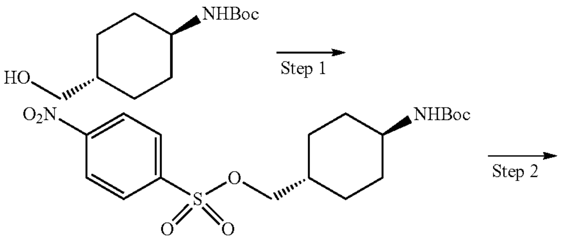

whb132

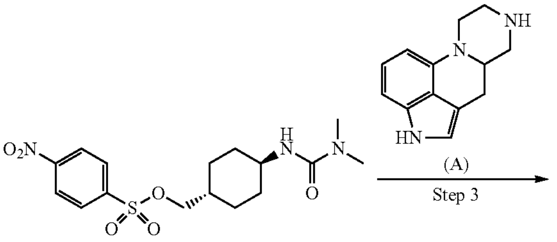

whb133

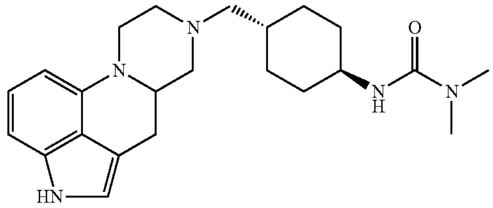

I-16

Step 1: tert-butyl(4-(hydroxymethyl)trans-cyclohexyl) carbamate (0.23 g, 1 mmol) was dissolved in DMF (5 mL), then triethylamine (1 mL) and 4-nitrobenzenesulfonyl chloride (0.27 g, 1.2 mmol) were successively added, and the reaction system was stirred overnight at room temperature. After the reaction was completed, the reaction was concentrated under reduced pressure, and the residue was purified by silica gel column chromatography (eluent: dichloromethane containing 0-10% methanol) to obtain intermediate whb132 (0.12 g, 29%) as a white solid. $^{1}$H NMR (800 MHz, $CDCl_3$) δ 8.43-8.38 (m, 2H), 8.12-8.08 (m, 2H), 3.93 (d, J=6.5 Hz, 2H), 3.42-3.29 (m, 1H), 2.06-2.00 (m, 2H), 1.78-1.76 (m, 2H), 1.70-1.65 (m, 1H), 1.43 (s, 9H), 1.17-1.07 (m, 4H). HR-MS (ESI, m/z): $C_{18}H_{26}N_2O_7SNa^+$ $[M+Na]^+$, calculated: 437.1358; found: 437.1323.

Step 2: the intermediate whb132 (0.12 g, 0.29 mmol) was dissolved in dichloromethane (3 mL), and trifluoroacetic acid (1.5 mL) was added and stirred at room temperature for 3 hours. After the reaction was completed, the reaction was concentrated under reduced pressure, and the residue was dissolved in tetrahydrofuran (5 mL), then triethylamine (2 mL) and dimethylcarbamoyl chloride (37 mg, 0.35 mmol) were added, and the reaction system was stirred overnight at room temperature. After the reaction was completed, the reaction was concentrated under reduced pressure, and the residue was purified by silica gel column chromatography (eluent: dichloromethane containing 10-20% methanol) to obtain intermediate whb133 (30 mg, 27%) as a white solid. $^{1}$H NMR (800 MHz, DMSO-$d_6$) δ 8.48-8.43 (m, 2H), 8.21-8.17 (m, 2H), 5.86 (d, J=7.8 Hz, 1H), 3.98 (d, J=6.4 Hz, 2H), 3.29-3.25 (m, 1H), 2.73 (s, 6H), 1.76-1.71 (m, 2H), 1.66-1.60 (m, 2H), 1.57-1.51 (m, 1H), 1.17-1.12 (m, 2H), 0.97-0.92 (m, 2H). HR-MS (ESI, m/z): $C_{16}H_{24}N_3O_6S^+$ $[M+H]^+$, calculated: 386.1380; found: 386.1391.

Step 3: the starting material (A) (50 mg, 0.23 mmol), the intermediate whb133 (30 mg, 0.078 mmol) and $K_2CO_3$ (127 mg, 0.92 mmol) were added into a round bottom flask, then solvents tetrahydrofuran (3 mL) and dimethyl sulfoxide (1 mL) were added. The reaction system was heated and stirred at 60° C. for 16 hours. After the reaction was completed, the reaction was concentrated under reduced pressure, and the residue was purified by silica gel column chromatography (eluent: dichloromethane containing 0-10% methanol) to obtain compound I-16 (12 mg, 13%) as an off-white solid. $^{1}$H NMR (800 MHz, $CDCl_3$) δ 7.92 (s, 1H), 7.06 (t, J=7.8 Hz, 1H), 6.79 (d, J=8.1 Hz, 1H), 6.71 (d, J=1.8 Hz, 1H), 6.32 (d, J=7.6 Hz, 1H), 4.14 (d, J=7.6 Hz, 1H), 3.76 (d, J=11.8 Hz, 1H), 3.63-3.58 (m, 1H), 3.26-3.21 (m, 1H), 3.03-2.94 (m, 3H), 2.88 (s, 6H), 2.80 (dd, J=15.3, 10.9 Hz, 1H), 2.34-2.30 (m, 1H), 2.24-2.21 (m, 2H), 2.11-2.07 (m, 1H), 2.07-2.03 (m, 2H), 1.91-1.85 (m, 2H), 1.55-1.50 (m, 1H), 1.14-1.02 (m, 4H). $^{13}$C NMR (201 MHz, $CDCl_3$) δ 157.94, 142.25, 134.37, 123.81, 118.13, 115.09, 109.13, 102.07, 98.78, 65.01, 60.65, 56.13, 53.38, 50.10, 46.23, 40.93, 36.19, 34.49, 33.83, 30.61, 27.62. HR-MS (ESI, m/z): $C_{23}H_{34}N_5O^+$ $[M+H]^+$, calculated: 396.2758; found: 396.2755.

Example 17: 3-(2-(4,6,6a,7,9,10-hexahydro-8H-pyrazino[1,2-a]pyrrolo[4,3,2-de]quinolin-8-yl)ethyl)-2-methyl-6,7,8,9-tetrahydro-4H-pyrido[1,2-a]pyrimidin-4-one (Compound I-17)

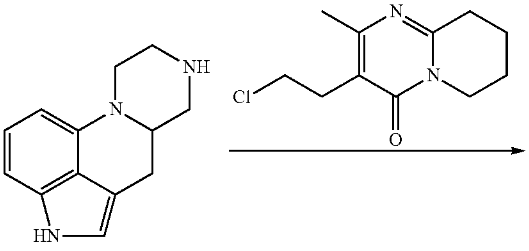

Raw material (A)

-continued

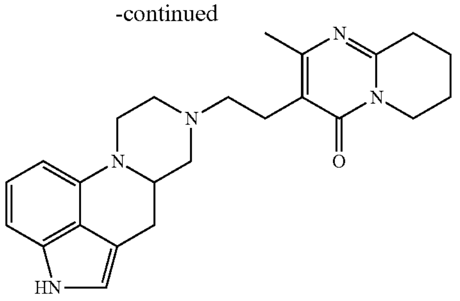

I-17

Following the method of step 2 of example 1, the starting material (A) and "3-(2-chloroethyl)-2-methyl-6,7,8,9-tetrahydro-4H-pyrido[1,2-a]pyrimidin-4-one" (cas #63234-80-0, commercially available) were subjected to alkylation reaction to prepare compound I-17 as a dark green solid, which was further purified by preparative HPLC (mobile phase: 20-80% MeOH/$H_2O$), $t_R$=16 min, to obtain 10 mg (yield 10%). $^1H$ NMR (800 MHz, DMSO-$d_6$) δ 10.68 (s, 1H), 10.03 (s, 1H), 6.97-6.92 (m, 1H), 6.90 (s, 1H), 6.80 (d, J=8.1 Hz, 1H), 6.33 (d, J=7.5 Hz, 1H), 4.11-4.05 (m, 1H), 3.90-3.82 (m, 2H), 3.80 (t, J=6.2 Hz, 2H), 3.23-3.15 (m, 2H), 3.08 (d, J=15.4 Hz, 2H), 3.00-2.95 (m, 1H), 2.93-2.84 (m, 2H), 2.79 (t, J=6.7 Hz, 2H), 2.75 (dd, J=15.4, 9.2 Hz, 1H), 2.26 (s, 3H), 2.03-1.96 (m, 1H), 1.88-1.85 (m, 2H), 1.79-1.75 (m, 2H), 1.48-1.43 (m, 1H). $^{13}C$ NMR (201 MHz, DMSO-$d_6$) δ 161.57, 158.89, 157.56, 139.89, 134.14, 123.03, 117.65, 116.57, 114.91, 105.99, 103.20, 98.97, 54.84, 53.65, 50.49, 43.45, 42.42, 30.65, 26.26, 21.14, 21.12, 20.79, 20.76, 18.35. HR-MS (ESI, m/z): $C_{24}H_{30}N_5O^+$ [M+H]$^+$, calculated: 404.2445; found: 404.2444.

Example 18: 7-(4-(4-methyl-4,6,6a,7,9,10-hexahydro-8H-pyrazino[1,2-a]pyrrolo[4,3,2-de]quinolin-8-yl)butoxy)quinolin-2(1H)-one (Compound I-18)

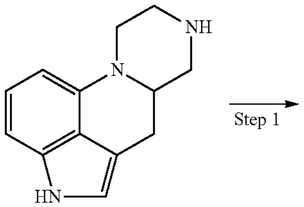

Raw material A

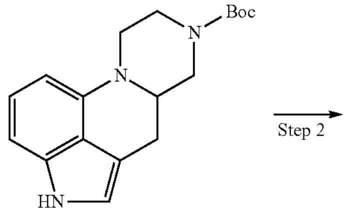

whb163

-continued

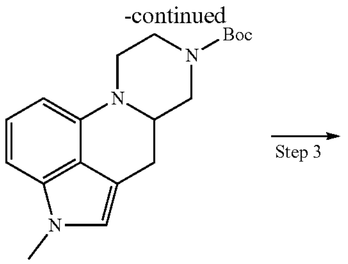

whb165

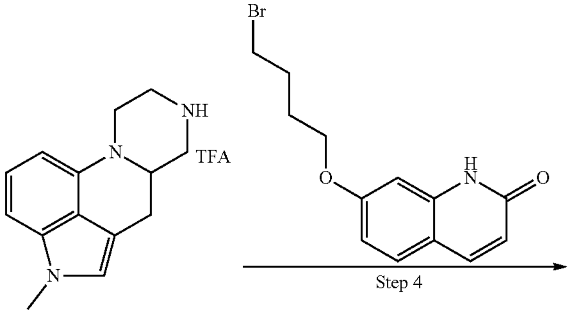

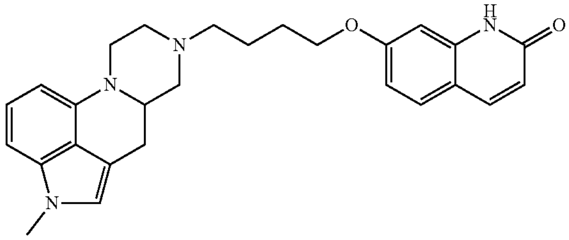

I-18

Step 1: the starting material (A) (0.20 g, 0.94 mmol), triethylamine (0.4 g, 3.76 mmol), DMAP (12 mg, 0.094 mmol) and solvent DMF (5 mL) were added into a round bottom flask, then $Boc_2O$ (0.23 g, 1.03 mmol) was added and stirred at room temperature for 12 hours. After the reaction was completed, the reaction was concentrated under reduced pressure to remove the solvent, and the residue was purified by silica gel column chromatography (eluent: dichloromethane containing 0-10% methanol) to obtain intermediate whb163 (0.22 g, 75%) as an off-white solid. $^1H$ NMR (800 MHz, $CDCl_3$) δ 7.85 (s, 1H), 7.09 (t, J=7.8 Hz, 1H), 6.82 (d, J=8.0 Hz, 1H), 6.75 (d, J=1.9 Hz, 1H), 6.35 (d, J=7.6 Hz, 1H), 4.31-4.21 (m, 1H), 4.20-4.08 (m, 1H), 3.81 (d, J=11.9 Hz, 1H), 3.19-3.11 (m, 1H), 3.11-3.01 (m, 2H), 2.94-2.72 (m, 3H), 1.49 (s, 9H). HR-MS (ESI, m/z): $C_{18}H_{24}N_3O_2^+$ [M+H]$^+$, calculated: 314.1863; found: 314.1862.

Step 2: the intermediate whb163 (0.21 g, 0.67 mmol), potassium tert-butoxide (0.091 g, 0.81 mmol) and DMF (8 mL) were added into a round bottom flask, and stirred for 30 minutes. Iodomethane (0.19 g, 1.34 mmol) was added and further stirred at room temperature for 3 hours. After the reaction was completed, water (3 mL) was added to the reaction system to quench the reaction, and a solid was precipitated out. Crude intermediate whb165 (0.18 g, 82%) was obtained by filtration as a yellow solid, which was directly used in the next step. $^1H$ NMR (800 MHz, $CDCl_3$) δ 7.13-7.08 (m, 1H), 6.75 (d, J=8.1 Hz, 1H), 6.59 (s, 1H), 6.33 (d, J=7.6 Hz, 1H), 4.29-4.24 (m, 1H), 4.21-4.08 (m, 2H), 3.82-3.80 (m, 1H), 3.73 (s, 3H), 3.17-3.10 (m, 1H), 3.09-3.04 (m, 1H), 3.01 (d, J=15.2 Hz, 1H), 2.80 (t, J=13.0

Hz, 2H), 1.48 (s, 9H). HR-MS (ESI, m/z): $C_{19}H_{26}N_3O_2^+$ $[M+H]^+$, calculated: 328.2020; found: 328.1990.

Step 3: the intermediate whb165 (50 mg) was dissolved in dichloromethane (3 mL), and TFA (1 mL) was added and stirred at room temperature for 1 hour. The solvent was evaporated under reduced pressure to obtain a crude product, which was directly used in the next step.

Step 4: the crude product obtained in step 3 was dissolved in tetrahydrofuran THF (3 mL), then DMSO (1.5 mL), $K_2CO_3$ (0.12 g, 0.87 mmol) and the intermediate wha70 of example 2 (49 mg, 0.17 mmol) were added, heated and stirred at 60° C. for 16 hours. The solvent was evaporated under reduced pressure, and the residue was purified by silica gel column chromatography (eluent: dichloromethane containing 0-10% methanol) to obtain compound I-18 of interest (30 mg, 45%) as a pale yellow solid. $^1H$ NMR (800 MHz, $CD_3OD$) δ 7.89 (d, J=9.4 Hz, 1H), 7.59 (d, J=8.7 Hz, 1H), 7.03 (t, J=7.8 Hz, 1H), 6.91 (dd, J=8.7, 2.4 Hz, 1H), 6.87 (d, J=2.4 Hz, 1H), 6.78 (d, J=8.2 Hz, 1H), 6.67 (s, 1H), 6.45 (d, J=9.4 Hz, 1H), 6.34 (d, J=7.5 Hz, 1H), 4.18-4.14 (m, 2H), 3.85 (d, J=12.0 Hz, 1H), 3.74 (s, 3H), 3.21-3.16 (s, 2H), 3.11-3.05 (m, 1H), 2.96 (d, J=15.3 Hz, 1H), 2.87 (t, J=12.0 Hz, 1H), 2.80-2.76 (m, 1H), 2.63-2.57 (m, 2H), 2.46-2.40 (m, 1H), 2.23-2.16 (m, 1H), 1.94-1.90 (m, 2H), 1.86-1.81 (m, 2H). $^{13}C$ NMR (201 MHz, $CDCl_3$) δ 165.14, 161.51, 142.23, 141.00, 140.50, 135.48, 129.14, 123.76, 119.86, 118.39, 117.98, 114.32, 112.78, 108.19, 100.42, 99.15, 98.64, 68.23, 60.01, 58.27, 56.31, 53.00, 46.31, 32.96, 27.67, 27.28, 23.39. HR-MS (ESI, m/z): $C_{27}H_{31}N_4O_2^+$ $[M+H]^+$, calculated: 443.2442; found: 443.2445.

Example 19: 1,1-dimethyl-3-(4-(2-(4-methyl-4,6,6a,7,9,10-hexahydro-8H-pyrazino[1,2-a]pyrrolo[4,3,2-de]quinolin-8-yl)ethyl)trans-cyclohexyl)urea (Compound I-19)

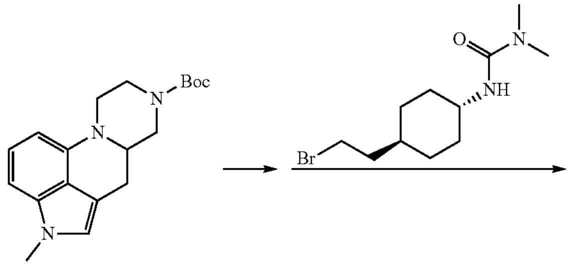

whb165

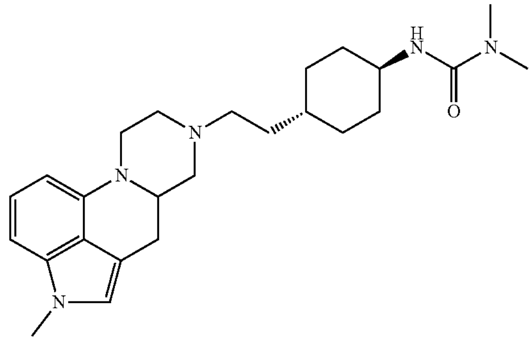

I-19

Using the method similar to that of example 17, the whb165 was subjected to removal of Boc protecting group first, and then subjected to alkylation reaction with the intermediate whb60 to obtain the compound I-19 (50 mg, 79%) as a pale yellow solid, which was further purified by HPLC (mobile phase: 20-80% MeOH/$H_2O$), $t_R$=19.5 min, to obtain 40 mg. $^1H$ NMR (800 MHz, $CD_3OD$) δ 7.08-7.04 (m, 1H), 6.83 (d, J=8.2 Hz, 1H), 6.75 (s, 1H), 6.39 (d, J=7.6 Hz, 1H), 4.15 (d, J=14.1 Hz, 1H), 3.73 (s, 3H), 3.73-3.68 (m, 2H), 3.51-3.47 (m, 1H), 3.37-3.32 (m, 1H), 3.26-3.20 (m, 3H), 3.15-3.12 (m, 1H), 3.05 (t, J=13.32 Hz, 1H), 3.00 (t, J=11.9 Hz, 1H), 2.87 (s, 6H), 2.87-2.81 (m, 1H), 1.95-1.89 (m, 2H), 1.85-1.84 (m, 2H), 1.74-1.65 (m, 2H), 1.39-1.32 (m, 1H), 1.32-1.26 (m, 2H), 1.16-1.10 (m, 2H). $^{13}C$ NMR (201 MHz, $CD_3OD$) δ 159.12, 139.54, 135.63, 123.24, 120.54, 118.09, 105.75, 101.38, 99.12, 55.68, 55.45, 54.33, 50.96, 49.78, 43.76, 35.04, 34.70, 32.64, 31.54, 31.52, 30.33, 26.24. HR-MS (ESI, m/z): $C_{25}H_{38}N_5O^+$ $[M+H]^+$, calculated: 424.3071; found: 424.3089.

Example 20: (E)-7-(4-(4,6,6a,7,9,10-hexahydro-8H-pyrazino[1,2-a]pyrrolo[4,3,2-de]quinolin-8-yl)-2-buten-1-yl)oxy)-3,4-dihydroquinolin-2(1H)-one (Compound I-20)

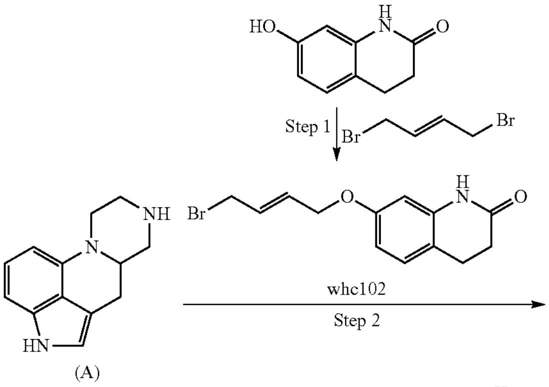

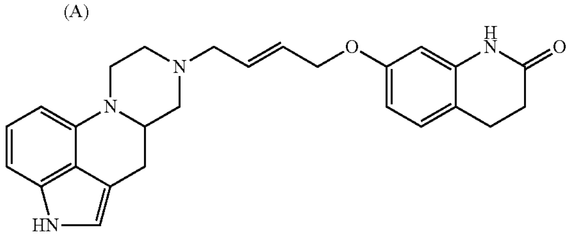

I-20

Step 1: following the method of step 1 of example 1, the alkylation reaction was carried out using 7-hydroxy-3,4-dihydroquinolin-2(1H)-one and (E)-1,4-dibromo-2-butene as raw materials to prepare intermediate whc102 (0.82 g, 45%) as a yellow solid. $^1H$ NMR (800 MHz, $CDCl_3$) δ 8.45 (s, 1H), 7.05 (d, J=8.2 Hz, 1H), 6.57-6.49 (m, 1H), 6.37 (d, J=2.5 Hz, 1H), 6.07 (dt, J=15.2, 7.4 Hz, 1H), 5.97 (dt, J=15.2, 5.3 Hz, 1H), 4.52 (d, J=5.4 Hz, 2H), 3.99 (d, J=7.5 Hz, 2H), 2.90 (t, J=7.5 Hz, 2H), 2.62 (t, J=7.5 Hz, 2H). HR-MS (ESI, m/z): $C_{13}H_{15}BrNO_2^+$ $[M+H]^+$, calculated: 296.0281; found: 296.0294 and 298.0277.

Step 2: following the method of step 2 of example 1, the intermediate A and the whc102 were subjected to alkylation reaction to obtain the compound I-20 (40 mg, 33%) as a pale yellow solid. HR-MS (ESI, m/z): $C_{26}H_{29}N_4O_2^+$ $[M+H]^+$, calculated: 429.2285; found: 429.2288.

Example 21: (E)-7-((4-(4,6,6a,7,9,10-hexahydro-8H-pyrazino[1,2-a]pyrrolo[4,3,2-de]quinolin-8-yl)-2-buten-1-yl)oxy)quinolin-2(1H)-one (Compound I-21)

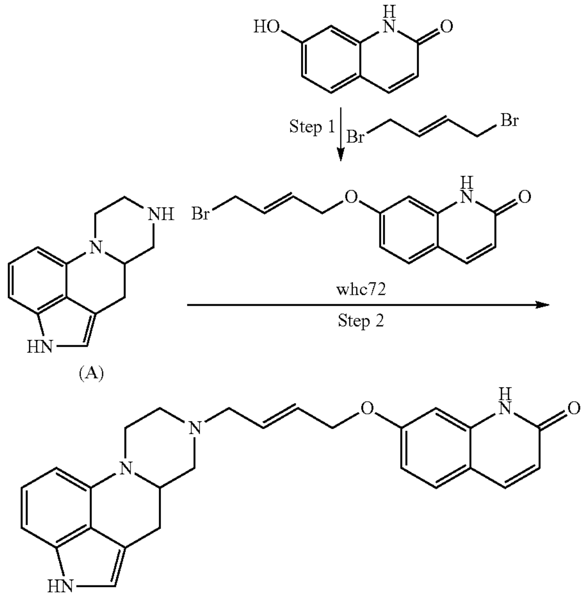

I-21

Step 1: following the method of step 1 of example 1, the alkylation reaction was carried out using 7-hydroxy-quinolin-2(1H)-one and (E)-1,4-dibromo-2-butene as raw materials to prepare intermediate whc72 (0.25 g, 14%) as a yellow solid. $^1$H NMR (600 MHz, $CDCl_3$) δ 7.74 (d, J=9.4 Hz, 1H), 7.46 (d, J=8.7 Hz, 1H), 6.88 (d, J=2.4 Hz, 1H), 6.86-6.80 (m, 1H), 6.59-6.47 (m, 1H), 6.14 (dt, J=15.0, 7.4 Hz, 1H), 6.01 (dt, J=15.4, 5.5 Hz, 1H), 4.66 (d, J=5.3 Hz, 2H), 4.01 (d, J=7.5 Hz, 2H). HR-MS (ESI, m/z): $C_{13}H_{13}BrNO_2^+$ $[M+H]^+$, calculated: 294.0124; found: 294.0124 and 296.0106.

Step 2: following the method of step 2 of example 1, the intermediate A and the whc72 were subjected to alkylation reaction to obtain the compound I-21 (50 mg, 51%) as an off-white solid. $^1$H NMR (800 MHz, $CDCl_3$) δ 10.12 (s, 1H), 7.83 (s, 1H), 7.69 (d, J=9.4 Hz, 1H), 7.45 (d, J=8.7 Hz, 1H), 7.07 (t, J=7.8 Hz, 1H), 6.85-6.82 (m, 1H), 6.80 (d, J=8.1 Hz, 1H), 6.72 (d, J=2.0 Hz, 1H), 6.69 (s, 1H), 6.51 (d, J=9.4 Hz, 1H), 6.32 (d, J=7.6 Hz, 1H), 6.03-5.98 (m, 1H), 5.95-5.91 (m, 1H), 4.65 (d, J=5.6 Hz, 2H), 4.14-4.10 (m, 1H), 3.80 (d, J=11.7 Hz, 1H), 3.22-3.20 (m, 1H), 3.14 (t, J=8.7 Hz, 1H), 3.07 (t, J=14.4 Hz, 2H), 2.94 (dd, J=15.1, 3.7 Hz, 2H), 2.83-2.77 (m, 1H), 2.40-2.36 (m, 1H), 2.12 (t, J=10.8 Hz, 1H). HR-MS (ESI, m/z): $C_{26}H_{27}N_4O_2^+$ $[M+H]^+$, calculated: 427.2129; found: 427.2129.

Example 22: (E)-7-((4-(4-methyl-4,6,6a,7,9,10-hexahydro-8H-pyrazino[1,2-a]pyrrolo[4,3,2-de]quinolin-8-yl)-2-buten-1-yl)oxy)-3,4-dihydroquinolin-2(1H)-one (Compound I-22)

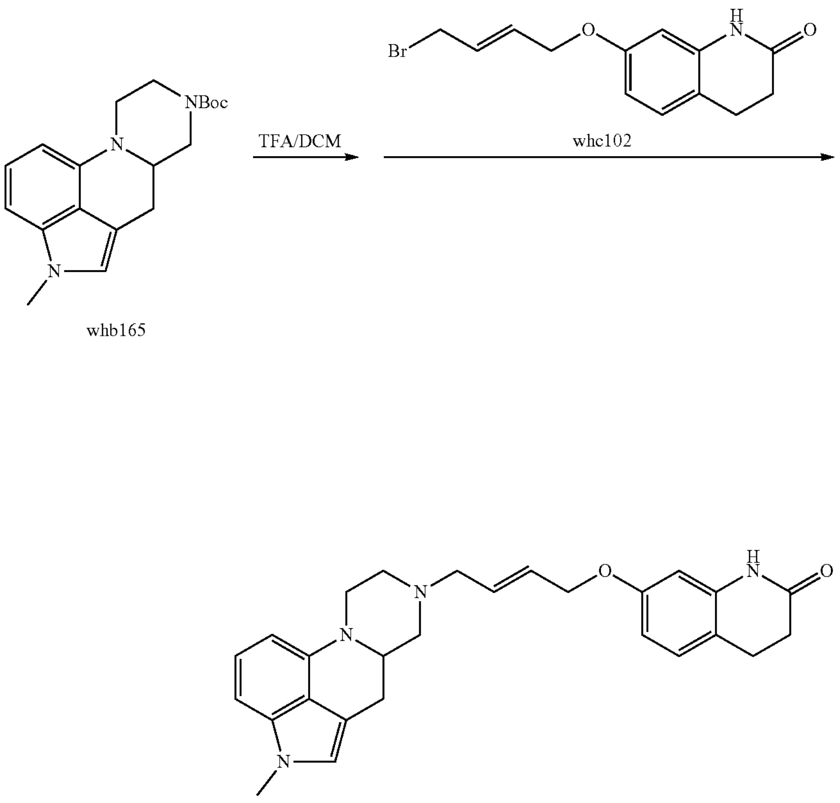

I-22

Following the method of step 3 of example 18, the intermediate whb165 was subjected to removal of Boc protecting group, and then subjected to alkylation reaction with the intermediate whc102 to obtain the compound I-22 of interest (90 mg, 30%) as a brown foamy solid. $^1$H NMR (800 MHz, $CD_3OD$) δ 7.09-7.04 (m, 2H), 6.82 (d, J=8.2 Hz, 1H), 6.72 (s, 1H), 6.58 (dd, J=8.3, 2.5 Hz, 1H), 6.49 (d, J=2.5 Hz, 1H), 6.36 (d, J=7.5 Hz, 1H), 6.26-6.22 (m, 1H), 5.97-5.93 (m, 1H), 4.66-4.62 (m, 2H), 4.11-4.05 (m, 1H), 3.84-3.75 (m, 2H), 3.71 (s, 3H), 3.64-3.59 (m, 1H), 3.56-3.52 (m, 1H), 3.13-3.09 (m, 1H), 3.08-3.00 (m, 2H), 2.82 (t, J=8.0 Hz, 3H), 2.77 (dd, J=15.6, 8.0 Hz, 1H), 2.48 (t, J=8.0 Hz, 2H). HR-MS (ESI, m/z): $C_{27}H_{31}N_4O_2^+$ [M+H]$^+$, calculated: 443.2442; found: 443.2442.

Example 23: (E)-7-((4-(4-methyl-4,6,6a,7,9,10-hexahydro-8H-pyrazino[1,2-a]pyrrolo[4,3,2-de]quinolin-8-yl)-2-buten-1-yl)oxy)quinolin-2(1H)-one (Compound I-23)

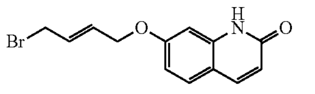

whc72

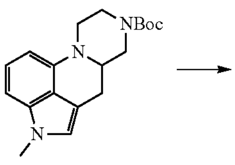

whb165

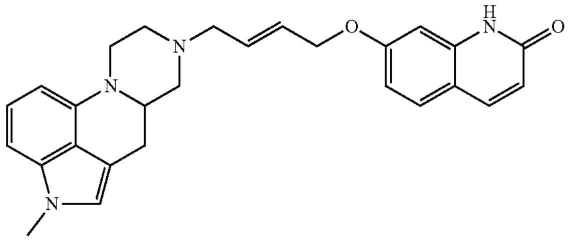

I-23

Following the method of step 3 of example 18, the intermediate whb165 was subjected to removal of Boc protecting group, and then subjected to alkylation reaction with the intermediate whc72 to obtain the compound I-23 of interest (23 mg, 20%) as a brown-yellow solid. $^1$H NMR (800 MHz, DMSO-$d_6$) δ 11.60 (s, 1H), 7.80 (d, J=9.5 Hz, 1H), 7.56 (d, J=8.3 Hz, 1H), 6.94 (t, J=7.8 Hz, 1H), 6.84-6.80 (m, 2H), 6.76-6.71 (m, 2H), 6.31 (d, J=9.4 Hz, 1H), 6.22 (d, J=7.5 Hz, 1H), 5.94-5.90 (m, 2H), 4.63 (d, J=5.1 Hz, 2H), 3.72-3.69 (m, 1H), 3.68 (s, 3H), 3.06-3.02 (m, 2H), 2.98-2.94 (m, 3H), 2.82 (d, J=15.2 Hz, 1H), 2.69-2.65 (m, 1H), 2.63-2.57 (m, 1H), 2.21-2.17 (m, 1H), 1.97-1.93 (m, 1H). HR-MS (ESI, m/z): $C_{27}H_{29}N_4O_2^+$ [M+H]$^+$, calculated: 441.2285; found: 441.2286.

Example 24: 1-(4-fluorobenzene)-4-(4,6,6a,7,9,10-hexahydro-8H-pyrazino[1,2-a]pyrrolo[4,3,2-de]quinolin-8-yl)-1-butanone (Compound I-24)

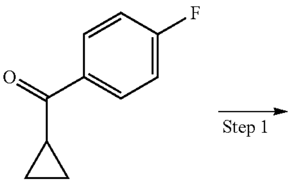

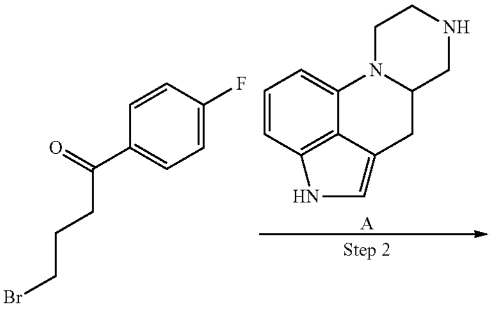

whc48

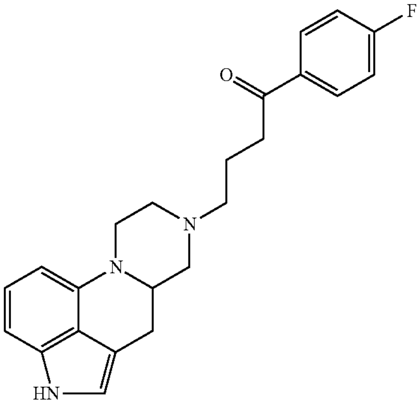

I-24

Step 1: cyclopropanyl(4-fluorobenzene)ketone (0.5 g, 3 mmol) and aqueous hydrobromic acid (3 mL) were added to a round bottom flask, and the reaction system was stirred at 80° C. for 2 hours. After the reaction was completed, the reaction was cooled, and water was added and extracted three times with DCM. The organic phases were combined and concentrated under reduced pressure to give crude product whc48 (0.73 g, 98%) as a yellow liquid. $^1$H NMR (800 MHz, $CDCl_3$) δ 8.04-7.99 (m, 2H), 7.17-7.12 (m, 2H), 3.55 (t, J=6.3 Hz, 2H), 3.16 (t, J=6.9 Hz, 2H), 2.31 (p, J=6.6 Hz, 2H).

Step 2: following the method of step 2 of example 1, the intermediate A and the whc48 were subjected to alkylation reaction to obtain the compound I-24 (0.3 g, 57%) as a pale yellow solid. $^1$H NMR (800 MHz, $CDCl_3$) δ 8.03-7.98 (m, 2H), 7.81 (s, 1H), 6.80 (d, J=8.1 Hz, 1H), 6.72 (d, J=1.9 Hz, 1H), 6.32 (d, J=7.6 Hz, 1H), 3.77 (d, J=11.7 Hz, 1H), 3.16-3.12 (m, 1H), 3.05-3.01 (m, 4H), 2.96 (dd, J=15.2, 3.7 Hz, 1H), 2.88-2.78 (m, 2H), 2.49 (t, J=7.1 Hz, 2H), 2.35 (t, J=8.0 Hz, 1H), 2.11 (t, J=8.0 Hz, 1H), 2.03-2.00 (m, 2H). HR-MS (ESI, m/z): $C_{23}H_{25}FN_3O^+$ [M+H]$^+$, calculated: 378.1976; found: 378.1976.

Example 25: 1-(4-fluorobenzene)-4-(4,6,6a,7,9,10-hexahydro-8H-pyrazino[1,2-a]pyrrolo[4,3,2-de]quinolin-8-yl)-1-butanol (Compound I-25)

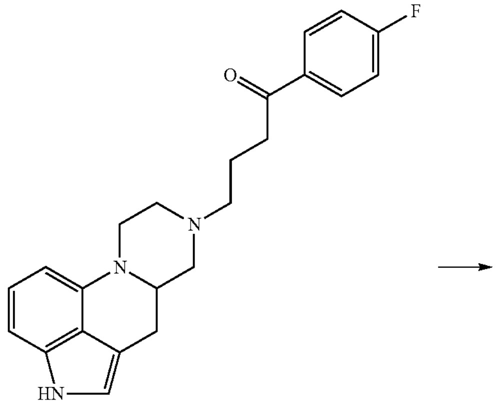

I-24

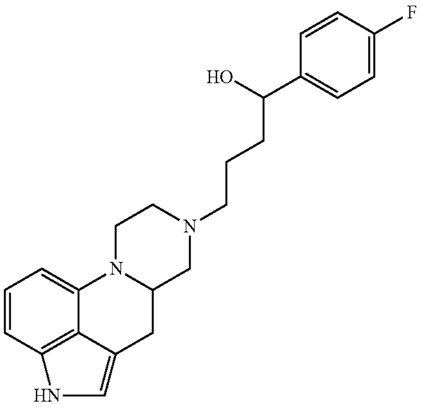

I-25

I-24 (50 mg, 0.13 mmol) was dissolved in methanol (5 mL), then $NaBH_4$ (7.6 mg, 0.19 mmol) was added, and the reaction system was stirred at room temperature for 2 hours. After the reaction was completed, the reaction was quenched by adding water and concentrated under reduced pressure, and the residue was purified by flash silica gel column chromatography (eluent: dichloromethane containing 20-30% methanol) to obtain I-25 (30 mg, 61%) as an off-white solid. $^1H$ NMR (600 MHz, $CDCl_3$) δ 7.82 (s, 1H), 7.36-7.30 (m, 2H), 7.10-7.04 (m, 1H), 7.01-6.97 (m, 2H), 6.81 (d, J=8.1, 1.3 Hz, 1H), 6.73 (d, J=7.7 Hz, 1H), 6.34 (dd, J=7.6, 2.4 Hz, 1H), 4.69 (td, J=8.2, 2.8 Hz, 1H), 3.87-3.80 (m, 1H), 3.34-3.30 (m, 1H), 3.23-3.19 (m, 1H), 3.08-2.91 (m, 3H), 2.83-2.79 (m, 1H), 2.54-2.50 (m, 2H), 2.48-2.37 (m, 1H), 2.25-2.14 (m, 1H), 2.00-1.96 (m, 1H), 1.88-1.84 (m, 1H), 1.76-1.72 (m, 2H). HR-MS (ESI, m/z): $C_{23}H_{27}FN_3O^+$ $[M+H]^+$, calculated: 380.2133; found: 380.2133.

Example 26: 1-(4-fluorobenzene)-4-(4-methyl-4,6,6a,7,9,10-hexahydro-8H-pyrazino[1,2-a]pyrrolo[4,3,2-de]quinolin-8-yl)-1-butanone (Compound I-26)

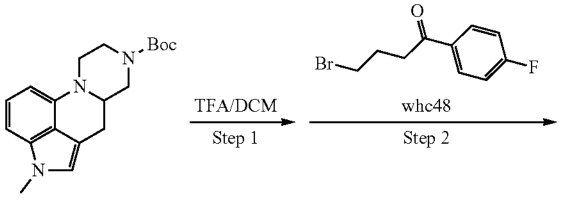

whb165

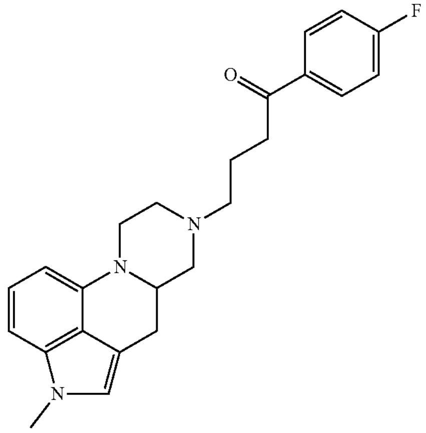

I-26

Following the method of step 3 of example 18, the intermediate whb165 was subjected to removal of Boc protecting group, and then subjected to alkylation reaction with the intermediate whc48 to obtain the compound I-26 (20 mg, 15%) as a pale yellow solid. $^1H$ NMR (800 MHz, DMSO-$d_6$) δ 8.04 (dd, J=8.6, 5.5 Hz, 2H), 7.32 (t, J=8.7 Hz, 2H), 6.93 (t, J=7.8 Hz, 1H), 6.75 (s, 1H), 6.71 (d, J=8.1 Hz, 1H), 6.20 (d, J=7.5 Hz, 1H), 3.69-3.68 (m, 1H), 3.67 (s, 3H), 3.04-3.00 (m, 3H), 2.99-2.95 (m, 1H), 2.91-2.84 (m, 2H), 2.63-2.60 (m, 1H), 2.59-2.55 (m, 1H), 2.42-2.38 (m, 2H), 2.20-2.16 (m, 1H), 2.00-1.95 (m, 1H), 1.88-1.84 (m, 2H). HR-MS (ESI, m/z): $C_{24}H_{27}FN_3O^+$ $[M+H]^+$, calculated: 392.2133; found: 393.2133.

Example 27: 1-(4-fluorobenzene)-4-(4-methyl-4,6,6a,7,9,10-hexahydro-8H-pyrazino[1,2-a]pyrrolo[4,3,2-de]quinolin-8-yl)-1-butanol (Compound I-27)

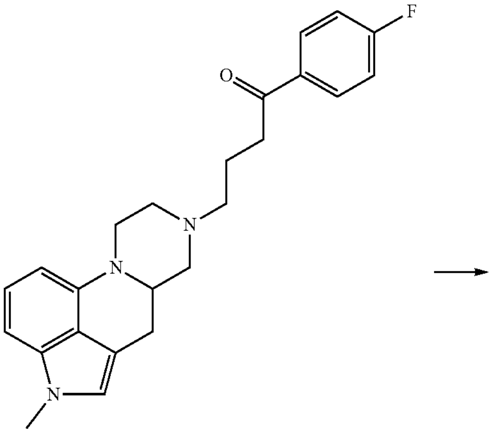

I-26

-continued

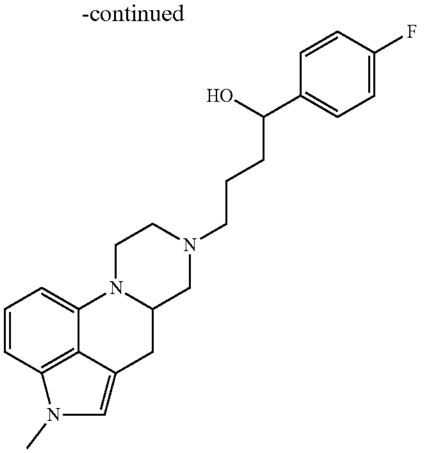

I-27

I-26 (63 mg, 0.16 mmol) was dissolved in methanol (8 mL), then NaBH 4 (9 mg, 0.24 mmol) was added, and the reaction system was stirred at room temperature for 2 hours. After the reaction was completed, the reaction was quenched by adding water and concentrated under reduced pressure, and the residue was purified by flash silica gel column chromatography (eluent: dichloromethane containing 20-30% methanol) to obtain I-27 (10 mg, 16%) as a pale yellow solid. $^1$H NMR (800 MHz, $CDCl_3$) δ 7.36-7.31 (m, 2H), 7.09 (t, J=7.7 Hz, 1H), 7.00-6.97 (m, 2H), 6.73 (d, J=7.8 Hz, 1H), 6.59-6.55 (m, 1H), 6.31 (d, J=7.7 Hz, 1H), 4.70-4.67 (m, 1H), 3.86-3.79 (m, 1H), 3.72 (s, 3H), 3.33-3.29 (m, 1H), 3.19-3.15 (m, 1H), 3.05-2.92 (m, 3H), 2.85-2.76 (m, 1H), 2.52-2.48 (m, 2H), 2.43-2.39 (m, 1H), 2.19-2.15 (m, 1H), 2.00-1.96 (m, 1H), 1.87-1.83 (m, 1H), 1.77-1.73 (m, 1H), 1.72-1.68 (m, 1H). HR-MS (ESI, m/z): $C_{24}H_{29}FN_3O^+$ $[M+H]^+$, calculated: 394.2289; found: 394.2297.

Test Example 1: Test of the Affinity of the Compounds of the Present Invention for Dopamine $D_2$ Receptors The affinity of the compounds of the present invention for the dopamine $D_2$ receptors was determined by the method of radioligand competition experiment. In the first step, a cell membrane component containing specific dopamine $D_2$ receptors was prepared. A 10 cm dish was used for transfection with 10 ng of the dopamine $D_2$ receptors and 40 μL of PEI. After 48 hours, the 10 cm dish was taken out from the cell culture room and the cultured cells had expressed the dopamine $D_2$ receptors. A vacuum pump was used to suck off the culture medium, 3 mL of lysis buffer was added to each well, and the cells were placed in a 4° C. freezer for 10 minutes. After the cells were detached, the cells were transferred to a 15 mL centrifuge tube and centrifuged at 1500 rpm for 5 minutes at 4° C., and the supernatant was discarded. The cell pellet was transferred to a tissue homogenizer, and 3 mL of lysis buffer was added and fully ground until the cells were broken. Then, cell suspension was equally divided into several EP tubes, centrifuged at 4° C. and 12000 rpm for 5 min, and the supernatant was discarded. The precipitate was the cell membrane component containing the dopamine $D_2$ receptors. In the second step, a ligand-receptor binding experiment was performed on HEK-293T membrane component transiently expressing the dopamine $D_2$ receptors. First, a standard binding buffer was added to the cell membrane component containing the dopamine $D_2$ receptors, and the cell membrane was disrupted and resuspended with an electric tissue homogenizer. 30 μL of membrane protein suspension was added to each well of a 96-well plate. Then, 30 μL of different drugs were added to the 96-well plate from left to right to ensure that the final drug concentrations were $10^{-5}$ M, $10^{-6}$ M, $10^{-7}$ M, $10^{-8}$ M, $10^{-9}$ M and 0 M, with two replicates per treatment. Next, 30 μL [$^3$H]-Methylspiperone was added to each well of the 96-well plate. The plate was incubated for 2 hours at room temperature in the dark. Detection. The machine reading value reflected the amount of [$^3$H]-Methylspiperone bound on the membrane, and after further data processing, the affinity $K_i$ value of different compounds for dopamine $D_2$ receptors was obtained.

The results are shown in Table 1. The results show that compound I-1 to compound I-27 have certain affinity activity for dopamine $D_2$ receptors, and it can be seen that the compounds of the invention have certain affinity activity for dopamine $D_2$ receptors.

TABLE 1

| Compound | Affinity $K_i$ ($pK_i$ ± SEM) |
|---|---|
| I-1 | 33.65 nM (7.47 ± 0.16) |
| I-2 | 9.03 nM (8.04 ± 0.12) |
| (+)-I-2 | 8.87 nM (8.05 ± 0.05) |
| (−)-I-2 | 1.75 nM (8.76 ± 0.13) |
| I-3 | 49.58 nM (7.30 ± 0.20) |
| I-4 | 30.34 nM (7.52 ± 0.08) |
| I-5 | 37.07 nM (7.43 ± 0.09) |
| I-6 | 51.56 nM (7.29 ± 0.10) |
| I-7 | 402.71 nM (6.40 ± 0.12) |
| I-8 | 0.49 nM (9.31 ± 0.15) |
| I-9 | 751.97 nM (6.12 ± 0.10) |
| I-10 | 50.64 nM (7.30 ± 0.08) |
| (−)-I-10 | 22.44 nM (7.65 ± 0.08) |
| (+)-I-10 | 1135.01 nM (5.95 ± 0.17) |
| I-11 | 22.23 nM (7.65 ± 0.06) |
| I-12 | 27.14 nM (7.57 ± 0.03) |
| I-13 | 16.31 nM (7.79 ± 0.07) |
| I-14 | 40.71 nM (7.39 ± 0.05) |
| I-15 | 77.45 nM (7.11 ± 0.12) |
| I-16 | 1992.20 nM (5.70 ± 0.14) |
| I-17 | 55.75 nM (7.25 ± 0.12) |
| I-18 | 60.95 nM (7.22 ± 0.02) |
| I-19 | 52.68 nM (7.28 ± 0.15) |
| I-20 | 70.9 nM |
| I-21 | 33.2 nM |
| I-22 | 176 nM |
| I-23 | 100.5 nM |
| I-24 | 32.4 nM |
| I-25 | 10.8 nM |
| I-26 | 1352 nM |
| I-27 | 383.1 nM |
| Aripiprazole | 5.95 nM (8.23 ± 0.08) |

Remark: data use [$^3$H]-Methylspiperone (0.3-0.5 nM) as the average $K_i$ ($pK_i$ ± SEM) of the competitive binding experiment of radioactive ligands. Wherein, all data of compounds I-1 to 19 are mean ± SEM of three independent determinations (n = 3 independent experiments); compounds I-20 to 27 were tested in a single determination, respectively.

Test Example 2: Test of the Functional Activity of the Compounds for Dopamine $D_2$ Receptors To examine downstream G-protein signaling pathway mediated by dopamine $D_2$ receptors, on the first day, 6 cm dish was used for transfection with 1 μg of dopamine $D_2$ receptors, 1 μg of $G\alpha_{i1}$ containing C-terminal seaweed luciferase ($G\alpha_{i1}$-Rluc), 1 μg of $G_{\beta 3}$, 1 μg of $G\gamma_9$ containing C-terminal green fluorescent protein ($G\gamma_9$-GFP) and 16 μL of PEI. At the same time, in order to examine the downstream β-arrestin2 signaling pathway mediated by dopamine $D_2$ receptors, on the first day, 6 cm dish was used for transfection with 500 μg of dopamine $D_2$ receptors containing C-terminal seaweed luciferase ($D_2$-Rluc), 500 μg of G protein-coupled receptor kinase 2 (GRK2), 2500 μg of β-arrestin2 containing N-terminal green fluorescent protein (GFP2-ARRB2) and 14 μL of PEI. The next day, the overgrown cells were digested and plated a 96-well plate at the amount of cells contained in a 6 cm culture dish with overgrown cells, and 100 μL of culture medium was added to each well. On the third day, the drugs were added for test. The 96-well plate was taken out from the cell culture room to remove the culture medium, 40 μL of the substrate coelenterazine 400a (final concentration of 5 μM) was added to each well, and then 20 μL of different drugs were added in turn from left to right to ensure that the final concentration of the drugs decreased gradually from bottom to top, and each treatment was repeated twice. Finally, the prepared samples were loaded on machine for test. The machine reading value reflected the intracellular β-arrestin2 on the membrane and the dissociation of G protein trimer. The former indicated the degree of activation of the β-arrestin2 signaling pathway downstream of the dopamine $D_2$ receptors, and the latter indicated the degree of activation of the G protein signaling pathway downstream of the dopamine $D_2$ receptors. Thus, the agonistic effect of various compounds on dopamine $D_2$ receptors can be revealed. The results are shown in Table 2.

The results show that compounds I-1 to I-25 all have certain agonistic activity for dopamine $D_2$ receptors.

TABLE 2

| Compound | $G_{\alpha i1}$ BRET $EC^1_{50}$ (Emax %[2] ± SEM) ($pEC_{50}$ ± SEM) | β-arrestin2 BRET $EC_{50}$ (Emax % ± SEM) ($pEC_{50}$ ± SEM) |
|---|---|---|
| I-1 | 16.21 nM (100 ± 2%) (7.79 ± 0.03) | 56.23 nM (100 ± 2%)(7.25 ± 0.05) |
| I-2 | 14.79 nM (101 ± 2%) (7.83 ± 0.03) | 48.98 nM (103 ± 2%) (7.31 ± 0.04) |
| (+)-I-2 | 1 nM (95 ± 2%) (9.07 ± 0.01) | 16 nM (89 ± 5%) (7.80 ± 0.05) |
| (−)-I-2 | 3 nM (91 ± 3%) (8.56 ± 0.06) | 18 nM (76 ± 2%) (7.74 ± 0.08) |
| I-3 | 43.65 nM (92 ± 2%) (7.36 ± 0.03) | 64.57 nM (93 ± 1%) (7.19 ± 0.03) |
| I-4 | 6.68 nM (80 ± 2%) (8.18 ± 0.15) | 71.01 nM (66 ± 2%) (7.15 ± 0.13) |
| I-5 | 7.44 nM (83 ± 1%) (8.13 ± 0.07) | 53.99 nM (61 ± 1%) (7.27 ± 0.06) |
| I-6 | 6.64 nM (86 ± 3%) (8.18 ± 0.08) | 61.61 nM (61 ± 2%) (7.21 ± 0.09) |
| I-7 | 138.04 nM (104 ± 1%) (6.86 ± 0.02) | 275.42 nM (97 ± 1%) (6.56 ± 0.10) |
| I-8 | 38.90 nM (94 ± 1%) (7.41 ± 0.01) | 109.65 nM (98 ± 1%) (6.96 ± 0.11) |
| I-9 | 165.96 nM (92 ± 1%) (6.78 ± 0.04) | 147.91 nM (96 ± 1%) (6.83 ± 0.12) |
| I-10 | 3.89 nM (80 ± 7%) (8.41 ± 0.21) | 6.61 nM (84 ± 1%) (8.18 ± 0.20) |
| (−)-I-10 | 1.38 nM (78 ± 1%) (8.86 ± 0.01) | 2.75 nM (89 ± 1%) (8.56 ± 0.06) |
| (+)-I-10 | 9.55 nM (86 ± 1%) (8.02 ± 0.02) | 5.25 nM (90 ± 1%) (8.28 ± 0.06) |
| I-11 | 9.33 nM (91 ± 1%) (8.03 ± 0.01) | 11.22 nM (87 ± 2%) (7.95 ± 0.05) |
| I-12 | 17.38 nM (92 ± 1%) (7.76 ± 0.03) | 20.42 nM (89 ± 3%) (7.69 ± 0.08) |
| I-13 | 6.74 nM (92 ± 3%) (8.17 ± 0.08) | 145.80 nM (48 ± 8%) (6.84 ± 0.12) |
| I-14 | 1.67 nM (72 ± 3%) (8.78 ± 0.08) | 27.71 nM (41 ± 2%) (7.56 ± 0.17) |
| I-15 | 2.65 nM (94 ± 2%) (8.58 ± 0.02) | 31.55 nM (80 ± 2%) (7.50 ± 0.05) |
| I-16 | 58.88 nM (84 ± 1%) (7.23 ± 0.01) | 40.74 nM (90 ± 1%) (7.39 ± 0.04) |
| I-17 | 32.65 nM (61 ± 2%) (7.49 ± 0.03) | 201.84 nM (38 ± 3%) (6.70 ± 0.03) |
| I-18 | 11.0 nM (77 ± 4%) (7.96 ± 0.02) | 110 nM (50 ± 2%) (6.96 ± 0.11) |
| I-19 | 4.0 nM (71 ± 5%) (8.38 ± 0.15) | 29 nM (34 ± 4%) (7.54 ± 0.05) |
| I-20 | 10.19 nM (74%) | 98.22 nM (88%) |
| I-21 | 7.71 nM (77%) | 61.90 nM (90%) |
| I-22 | 38.05 nM (41%) | 91.61 nM (32%) |
| I-23 | 54.77 nM (38%) | 294.40 nM (36%) |
| I-24 | 11.41 nM (38%) | 10.43 nM (26%) |
| I-25 | 7.48 nM (29%) | 9.60 nM (30%) |
| I-26 | 7621 nM (antagonistic activity) | Inactive |
| I-27 | 1204 nM (antagonistic activity) | 1540 nM (antagonistic activity) |
| Aripiprazole | 426.58 (60 ± 1%) (6.37 ± 0.05) | 309.03 (58 ± 3%) (6.51 ± 0.10) |

Remark: all data of compounds I-1 to 19 are mean ± SEM of three independent determinations (n = 3 independent experiments); compounds I-20 to 27 were tested in a single determination, respectively.

[1]$EC_{50}$ is the concentration of a compound that gives half the maximal response in the experiment.

[2]The $E_{max}$ % in the bracket indicates the percentage of the maximum response intensity ($E_{max}$) produced by the compound in the experiment relative to the endogenous ligand dopamine.

Example 3: Test of the Affinity of the Compounds of the Present Invention for 5-$HT_{2A}$ Receptor The affinity of the compounds of the present invention for the 5-$HT_{2A}$ receptors was determined by the method of radioligand competition experiment. In the first step, a cell membrane component containing specific 5-$HT_{2A}$ receptor was prepared. A 10 cm dish was used for transfection with 10 ng of the 5-$HT_{2A}$ receptor and 40 μL of PEI. After 48 hours, the 10 cm dish was taken out from the cell culture room and the cultured cells had expressed the 5-$HT_{2A}$ receptor. A vacuum pump was used to suck off the culture medium, 3 mL of lysis buffer was added to each well, and the cells were placed in a 4° C. freezer for 10 minutes. After the cells were detached, the cells were transferred to a 15 mL centrifuge tube and centrifuged at 1500 rpm for 5 minutes at 4° C., and the supernatant was discarded. The cell pellet was transferred to a tissue homogenizer, and 3 mL of lysis buffer was added and fully ground until the cells were broken. Then, cell suspension was equally divided into several EP tubes, centrifuged at 4° C. and 12000 rpm for 5 min, and the supernatant was discarded. The precipitate was the cell membrane component containing the 5-$HT_{2A}$ receptor. In the second step, a ligand-receptor binding experiment was performed on HEK-293T membrane component transiently expressing the 5-$HT_{2A}$ receptor. First, a standard binding buffer was added to the cell membrane component containing the 5-$HT_{2A}$ receptor, and the cell membrane was disrupted and resuspended with an electric tissue homogenizer. 30 μL of membrane protein suspension was added to each well of a 96-well plate. Then, 30 μL of different drugs were added to the 96-well plate from left to right to ensure that the final drug concentrations were $10^{-5}$ M, $10^{-6}$ M, $10^{-7}$ M, $10^{-8}$ M, $10^{-9}$ M and 0 M, with two replicates per treatment. Next, 30 μL [$^3$H]-ketanserin was added to each well of the 96-well plate. The plate was incubated for 2 hours at room temperature in the dark. Detection. The machine reading value reflected the amount of [$^3$H]-ketanserin bound on the membrane, and after further data processing, the affinity $K_i$ value of different compounds for 5-$HT_{2A}$ receptor was obtained. The results are shown in Table 3.

TABLE 3

| Compound | $K_i$, nM ($pK_i$ ± SEM) |
|---|---|
| I-1 | 3639.15 (5.44 ± 0.02) |
| I-2 | 906.78 (6.04 ± 0.01) |
| I-10 | 2371.37 (5.63 ± 0.04) |
| (−)-I-10 | 2627.24 (5.58 ± 0.09) |
| (+)-I-10 | 2480.28 (5.61 ± 0.09) |
| Aripiprazole | 42.17 (7.38 ± 0.03) |

The results in Table 3 show that compounds I-1, I-2, I-10, (−)-I-10 and (+)-I-10 have very weak affinity for 5-$HT_{2A}$ receptor. Comparing the data in Table 1, the binding selectivity of compounds I-1, I-2, (−)-I-10 to 5-$HT_{2A}$ receptor is more than 100 times, it can be seen that the compounds of the invention have good selectivity for dopamine $D_2$ receptor.

Test Example 3: Test of the Pharmacokinetic Properties of the Compounds of the Present Invention in Mice 1. Test of the Pharmacokinetic Properties of Compound (−)-I-10 Administered to C57 Male Mice by Single Intragastric Administration, Intraperitoneal Injection and Intravenous Injection (1) Purpose of the Experiment Compound (−)-I-10 was administered in a single dose in C57 male mice, and then blood samples were collected at different time points, the concentration of the compound in mouse plasma was determined by LC-MS/MS and the relevant pharmacokinetic parameters were calculated to investigate the pharmacokinetics of the compound in the mice.

(2) Experimental Design 27 male C57 mice were provided by Suzhou Zhaoyan Experimental Animal Co., Ltd., and the experiment was carried out according to Table 4 below.

TABLE 4

| Group | Test substance | Administration dosage (mg/kg) | Administration concentration (mg/mL) | Administration volume (mL/kg) | Sample collection | Administration mode | Vehicle |
|---|---|---|---|---|---|---|---|
| G1 | (−)-I-10 | 1.0 | 0.2 | 5.0 | Plasma | IP | 5% DMSO + |
| G2 | (−)-I-10 | 5.0 | 0.5 | 10.0 | Plasma | PO | 95% normal |
| G3 | (−)-I-10 | 1.0 | 0.2 | 5.0 | Plasma | IV | saline |

(3) Sample Collection 0.030 mL of blood was taken from each animal through the orbit each time and anticoagulated with EDTA-K2, and the collection time points were: 0, 5, 15, 30 min, 1, 2, 4, 6, 8, 24 h after administration of the test substance. Blood samples were placed on ice after collection, and the plasma was separated by centrifugation within 30 minutes (centrifugation conditions: 5000 rpm, 10 minutes, 4° C.) and stored at −80° C. until analysis.

(4) Data Processing

Data acquisition and control system software was Analyst 1.5.1 software (Applied Biosystem). The sample peak integration method of the spectrum was automatic integration; the ratio of the peak area of the sample to the peak area of the internal standard was used as an index, and regression was performed with the concentration of the sample. Regression method: linear regression with a weight factor of 1/X2. Pharmacokinetic parameters were analyzed using WinNonlin Professional v6.3 (Pharsight, USA) using non-compartmental models. Cmax was the measured maximum drug concentration in blood, the area under the drug concentration in blood-time curve AUC (0→t) was calculated by the trapezoidal method, and Tmax was the time to peak of the drug concentration in blood after administration. The experimental data were expressed by "mean±standard deviation" (Mean±ICR, n≥3) or "mean" (Mean, n=2).

(5) Experimental Results

The pharmacokinetic results of compound (−)-I-10 are shown in the table below. It can be seen that the compound has good pharmacokinetic properties in C57 male mice. See Table 5 for details.

TABLE 5

| Pharmacokinetic parameters | | Intravenous injection | Intraperitoneal injection | Oral administration |
|---|---|---|---|---|
| Administration dosage | mg · $kg^{-1}$ | 1 | 1 | 5 |
| Terminal elimination rate $K_{el}$ | $h^{-1}$ | 0.805 | 0.886 | 0.604 |
| Terminal elimination half-life $t_{1/2}$ | h | 0.861 | 0.782 | 1.15 |
| Time to peak $t_{max}$ | h | — | 0.0833 | 0.0833 |
| Drug peak concentration $C_{max}$ | ng · $mL^{-1}$ | — | 271 | 558 |
| Area under the drug-time curve $AUC_{0-t}$ | h · ng · $mL^{-1}$ | 211 | 172 | 591 |
| Area under the drug-time curve $AUC_{0-inf}$ | h · ng · $mL^{-1}$ | 215 | 175 | 596 |
| Clearance CL | mL/min/kg | 77.6 | — | — |
| Mean residence time $MRT_{PO}$ | h | 1.04 | 0.770 | 1.49 |
| Apparent volume of distribution Vdss | L/kg | 4.86 | — | — |
| Bioavailability F | % | — | 81.4 | 55.9 |

Remark: "—" indicates not applicable.

2. Test of the Brain Permeability of Compound (−)-I-10 Administered to C57 Male Mice by Single Intragastric Administration, Intraperitoneal Injection and Intravenous Injection Using the same method as the pharmacokinetic experiment, 0.030 mL of blood was taken from each animal through the orbit at 0.5 and 2.0 hours, respectively, and anticoagulated with EDTA-K2. Blood samples were placed on ice after collection, and the plasma was separated by centrifugation within 30 minutes (centrifugation conditions: 5000 rpm, 10 minutes, 4° C.) and stored at −80° C. until analysis. After the animal was euthanized by bloodletting, the brain tissue samples were taken, homogenized with 50% methanol according to the body weight of 1:3 (m/v=1:3), and stored at −80° C. before homogenate analysis. The drug concentrations in plasma and brain tissue were analyzed by LC/MS/MS and compared. Table 6 shows the drug concentration and ratio of compound (−)-I-10 in plasma and brain tissue at 0.5 and 2.0 h.

TABLE 6

| | Intravenous injection 1 mg/kg | Intraperitoneal injection 1 mg/kg | Oral administration 5 mg/kg |
|---|---|---|---|
| Drug concentration at 0.5 h in brain (ng/mL) | 219 ± 21 | 193 ± 13 | 346 ± 217 |
| Drug concentration at 0.5 h in plasma (ng/mL) | 133 ± 19 | 124 ± 15 | 231 ± 153 |
| Brain/blood concentration ratio at 0.5 h | 1.65 | 1.56 | 1.50 |
| Drug concentration at 2.0 h in brain (ng/mL) | 77.0 ± 7.0 | 42.7 ± 4.0 | 169 ± 23 |
| Drug concentration at 2.0 h in plasma (ng/mL) | 24.9 ± 5.0 | 13.8 ± 2.7 | 95 ± 16 |
| Brain/blood concentration ratio at 2.0 h | 3.09 | 3.10 | 1.78 |

Test Example 4: Pharmacodynamic Test of Compounds on Schizophrenia-Like Animal Behavioral Model 1. Open Field Athletic Ability Test Experimental method: The experimental animals were C57B6 male mice, n=8 in each group. This model used C57B6 mice as experimental animals. The behavioral representation of hyperkinesia in open field environment in mice was induced by acute injection of NMDA antagonist MK801 and modeled to test the inhibitory effect of different compounds on hyperkinesia phenotype induced by MK801. All mouse behavior experiments were carried out during the light period of the mice, and the whole experiment was recorded by the camera and automatic tracking and data statistics were carried out by behavioral tracking software. The compound was administered by intraperitoneal injection. Immediately after the injection, the mice entered the open field and their movement trajectories began to record. After 30 minutes, the mice received 0.2 mg/kg of MK801 by intraperitoneal injection and returned to the open field immediately after administration and the movement trajectories were further recorded for 120 min. The accumulative moving distance of the mice was counted at a data sampling point every five minutes. Data statistics were carried out using Student-t-test, $p<0.05$ was *, $p<0.01$ was , $p<0.001$ was *, $p<0.0001$ was ****. The total moving distance of the mice in 0-45 minutes under the combined action of different doses of (−)-I-10 and MK801 (0.2 mg/kg) is shown in Table 7.

The test results of open field athletic ability show that compound (−)-I-10 at 0.4/0.1/0.025 mg/kg could significantly inhibit the improvement of athletic ability of the mice induced by MK801.

TABLE 7

| | Normal | MK801 (0.2 mg/kg) | | | | |
|---|---|---|---|---|---|---|
| Administration condition | saline Normal saline | Normal saline | (−)-I-10 0.4 mg/kg | (−)-I-10 0.1 mg/kg | (−)-I-10 0.025 mg/kg | (−)-I-10 0.00625 mg/kg |
| 45 minutes moving distance (cm) | 3180 ± 406.4 | 13335 ± 930 | 2644 ± 294.2 | 3833 ± 272.7 | 8643 ± 668.3 | 11626 ± 1820 |

2. Animal "Depression-Like" Behavior Test

The experimental animals were C57B6 male mice, n=8 in each group. Firstly, the C57B6 mice were induced to develop depression-related behavioral representations by restraining the mice for 5 hours, and then the effects of the compounds on their "depression-like" behaviors were determined by tail suspension and forced swimming experiments. The specific experimental procedure was as follows. First, the mice were restrained using a mouse fixator for tail vein injection. During the restraint process, all behavioral abilities of the mice were restricted under the condition of ensuring minimal pain to the mice. The mice were administered intraperitoneally once before and after restraint, respectively. After the restraint, the mice returned to the cage to recover for 30 minutes. After the 30 minutes, the mice in different groups were subjected to tail suspension or forced swimming to detect their "depression-like" behavior, respectively.

Tail suspension experiment: the tip of the tail of the mouse was fixed on the suspension rod of the iron stand by adhesive tape, and the mouse remained in the hanging position for 6 minutes. The first 2 minutes was the adaptation period, and no data collection was performed, and the time of the intermittent immobility behavior of the mouse was recorded in the next 4 minutes. The duration of this immobility state was used to measure the degree of behavioral despair in the mouse. Data statistics were carried out using Student-t-test, $p<0.05$ was *, $p<0.01$ was , $p<0.001$ was *, $p<0.0001$ was ****.

Forced swimming experiment: the mouse was placed in a 5 L glass beaker filled with water, the water surface height was 15 cm, and the mouse needed to swim continuously in the beaker for 6 minutes. The first two minutes was the adaptation period and no data collection was performed. The time of the intermittent immobility behavior of the mouse was recorded in the next four minutes, and the immobility behavior of the mouse was defined as: the mouse float passively on the surface of the water without movement, with only small local movements required to maintain afloat. The duration of this immobility state was used to measure the degree of behavioral despair in the mouse. Data statistics were carried out using Student-t-test, $p<0.05$ was *, $p<0.01$ was , $p<0.001$ was *, $p<0.0001$ was ****. The results of statistical data of restrained and unrestrained mouse tail suspension experiment and forced swimming experiment are shown in Table 8.

The test results of "depression-like" behavior show that compound (−)-I-10 at 0.4 mg/kg and 0.1 mg/kg could significantly inhibit the restraint-induced "depression-like" behavior.

TABLE 8

| Treatment condition | | Unrestrained Normal saline | Restraint for five hours | | | | |
|---|---|---|---|---|---|---|---|
| | | | Normal saline | (−)-I-10 0.4 mg/kg | (−)-I-10 0.1 mg/kg | (−)-I-10 0.025 mg/kg | (−)-I-10 0.00625 mg/kg |
| Immobility time (seconds) | Tail suspension experiment | 74.81 ± 11.00 | 125.4 ± 8.083 | 72.66 ± 6.486 | 90.31 ± 10.26 | 101.8 ± 10.85 | 132.6 ± 5.708 |
| | Forced swimming experiment | 25.40 ± 6.387 | 81.62 ± 3.242 | 22.40 ± 5.272 | 42.76 ± 6.698 | 56.59 ± 9.965 | 76.09 ± 5.943 |

3. Old and Novel Object Recognition

The experimental animals were C57B6 male mice, n=8 in each group. Firstly, mice were intraperitoneally injected with MK801 at 0.3 mg/kg twice a day for seven consecutive days to establish a recognition impairment model, and control mice were intraperitoneally injected with normal saline containing the same amount of DMSO. The mice then underwent a seven-day recovery in home cages. After the recovery period expired, the old and novel object distinguishing experiment was performed on the mice to determine the effect of the compounds on the recognition ability of the mice.

Novel and old object recognition experiment: The experiment was carried out in a low-light environment. Before the experiment started, the mice were placed in the experimental field in advance and adapted to the environment for one hour in the low-light environment. After environmental adaptation, the mice were administered intraperitoneally. 30 minutes after the administration, the mice were put in an open field (diameter of the open field of 40 cm) in which two identical objects had been placed beforehand. The mice explored freely in the open field for 10 minutes, and then were removed from the open field and returned to the cage. After a one-hour interval, the mice returned to the open field, where an old object and a novel object were placed in advance in the same position in the open field. Again, the mice explored freely in the open field for 10 minutes. The distinguishing time of the mice for the old object and the novel object was recorded separately and the distinguishing index was calculated. The calculation method of the distinguishing index was (exploration time for novel object−exploration time for old object)/(exploration time for novel object+exploration time for old object). Object exploration by the mice was defined as sniffing, climbing, and direct contact with the object. Data statistics were carried out using Student-t-test, $p<0.05$ was *, $p<0.01$ was **, $p<0.001$ was

*, p<0.0001 was **. Table 9 shows the statistical data results of old and novel object distinguishing index.

The results of old and novel object distinguishing show that compound (−)-I-10 at 0.1 mg/kg and 0.025 mg/kg could significantly improve MK801-induced recognition impairment in mice.

The results of Morris water maze show that compound (−)-I-10 at 0.1 mg/kg could significantly improve MK801-induced spatial recognition impairment in mice; compound (−)-I-10 at 0.1 mg/kg and 0.025 mg/kg could significantly improve MK801-induced memory impairment in mice.

TABLE 9

| | | MK801 (0.3 mg/kg) 14 injections in 7 days; 7 days recovery modeling | | | |
|---|---|---|---|---|---|
| Administration condition | Normal saline Normal saline | Normal saline | (−)-I-10 0.1 mg/kg | (−)-I-10 0.025 mg/kg | (−)-I-10 0.00625 mg/kg |
| Distinguishing index (DI) | 0.3032 ± 0.04355 | 0.08611 ± 0.01956 | 0.2789 ± 0.04036 | 0.3320 ± 0.06367 | 0.05971 ± 0.03658 |

4. Morris Water Maze

The experimental animals were C57B6 male mice, n=8 in each group. Firstly, mice were intraperitoneally injected with 0.2 mg/kg of MK801 twice a day for ten consecutive days to establish a recognition impairment model, and control mice were intraperitoneally injected with normal saline containing the same amount of DMSO, and then the mice were subjected to the Morris water maze test.

Experimental setup: Experiments were conducted in a blue circular water reservoir with a diameter of 130 cm. The reservoir was filled with pure water about 30 cm deep. The reservoir was divided into 4 fan-shaped areas by a cross, and the escape platform (6 cm in diameter) was located in the center of one of the fan-shaped areas and was hidden 0.5 cm below the water surface. The position where the mice entered the water was fixed at the edges of the other three fan-shaped areas. The position where the mice entered the water was basically consistent with the straight-line distance of the platform.

Acquisition phase: 30 minutes before the start of the experiment, the mice were administered intraperitoneally. After the experiment started, the mouse was put into the water with its head facing the reservoir wall, and the placement position was randomly selected from one of the three starting positions in the east, west, and south, and the underwater hidden platform was located in the north quadrant. The time taken by the mouse to find the underwater platform was recorded. If the mouse did not find the platform within 1 minute, the mouse was guided to the platform and stayed on the platform for 30 seconds. Then the above steps were repeated 2 times at another starting position. Each animal was trained three times a day for 5 consecutive days.

Probe trial: on the second day after the last acquisition phase, the platform was removed and a 60-second probe trial began. The animal was placed in the water from the opposite side of the original platform quadrant. The number of times the animal crossed the original platform location was recorded as a detection index of spatial memory. Data statistics were carried out using Student-t-test, p<0.05 was *, p<0.01 was , p<0.001 was *, p<0.0001 was ****. For water maze acquisition phase, the results of daily platform exploration time are shown in Table 10.

TABLE 10

| | | Normal | MK801 (0.2 mg/kg) 20 injections in 10 days for modeling | | | |
|---|---|---|---|---|---|---|
| Administration condition | | saline Normal saline | Normal saline | (−)-I-10 0.1 mg/kg | (−)-I-10 0.025 mg/kg | (−)-I-10 0.00625 mg/kg |
| Platform exploration time (seconds) | First day | 162.9 ± 9.672 | 160.3 ± 6.917 | 146.2 ± 9.984 | 161.2 ± 9.932 | 173.0 ± 5.086 |
| | Second day | 130.3 ± 15.86 | 151.7 ± 10.57 | 128.5 ± 16.33 | 154.0 ± 11.34 | 145.3 ± 14.15 |
| | Third day | 95.23 ± 18.99 | 128.3 ± 11.41 | 88.38 ± 11.66 | 96.66 ± 20.94 | 108.1 ± 18.03 |
| | Fourth day | 70.60 ± 13.36 | 116.7 ± 19.28 | 68.62 ± 10.98 | 96.66 ± 19.27 | 87.77 ± 13.59 |
| | Fifth day | 48.16 ± 6.160 | 109.5 ± 18.62 | 62.86 ± 12.34 | 92.23 ± 12.25 | 97.94 ± 14.27 |

| | Normal | MK801 (0.2 mg/kg) 20 injections in 10 days for modeling | | | |
|---|---|---|---|---|---|
| Administration condition | saline Normal saline | Normal saline | (−)-I-10 0.1 mg/kg | (−)-I-10 0.025 mg/kg | (−)-I-10 0.00625 mg/kg |
| Times of crossing platform area | 6.600 ± 0.4989 | 1.900 ± 0.3480 | 5.800 ± 0.7860 | 4.500 ± 0.4282 | 2.600 ± 0.3712 |

5. Freezing Behavior Test

Experimental method: The experimental animals were C57B6 male mice, n=8 in each group. Mice were first injected with different compounds, and after a certain period of time (30 min or 60 min), the mice were in an upright and unnatural state by placing their forelimbs on a high glass hanging rod (about 5 cm from the ground). Then the time for the mice to maintain this state was measured, and the length of time was used to determine the freezing effect of the drug on the mice. The test results of the freezing behavior of the mice 30 and 60 minutes after injection of different drugs are shown in Table 11.

The freezing behavior test show that compound (−)-I-10 at 10 mg/kg has no freezing induction effect on mice.

TABLE 11

| Time after | Freezing time (seconds) | |
|---|---|---|
| administration (minutes) | Haloperidol (10 mg/kg) | (−)-I-10 (10 mg/kg) |
| 30 minutes | 61.05 ± 3.239 | 2.194 ± 0.2524 |
| 60 minutes | 53.19 ± 2.443 | 2.165 ± 0.3256 |

What is claimed is:

1. A compound as shown in formula I, a pharmaceutically acceptable salt thereof:

I

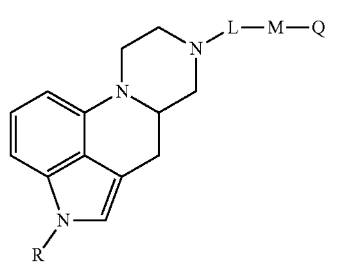

wherein L is $C_{1-10}$ alkylene, $C_{2-10}$ alkenylene, $C_{2-10}$ alkynylene or —$C_{1-6}$ alkylene-$C_{3-6}$ cycloalkylene-;

M is —O—, —NH—, —$CH_2$—, —(CH—OH)— or —C(═O)—;

Q is $C_{6-18}$ aryl, $C_{6-18}$ aryl substituted with one or more $Q^{1-1}$, 5 to 10 membered heteroaryl, 5 to 10 membered heteroaryl substituted with one or more $Q^{1-2}$, —C(═O)$R^1$ or —S(═O)$_2R^2$; the heteroatoms in the 5 to 10 membered heteroaryl are one or more of N, S or O, and the number is 1, 2 or 3; the heteroatoms in the 5 to 10 membered heteroaryl substituted with one or more $Q^{1-2}$ are one or more of N, S or O, and the number is 1, 2 or 3;

when Q is $C_{6-18}$ aryl or $C_{6-18}$ aryl substituted with one or more $Q^{1-1}$, M is —O—, —NH—, —(CH—OH)— or —C(═O)—;

$Q^{1-1}$ is independently halogen or $C_{1-4}$ alkyl;

$Q^{1-2}$ is independently $C_{1-4}$ alkyl, oxo or hydroxyl;

$R^1$ and $R^2$ are independently —$NR^{1-1}R^{1-2}$, 3 to 6 membered heterocycloalkyl, $C_{6-18}$ aryl, $C_{6-18}$ aryl substituted with one or more $R^{1-3}$, 5 to 10 membered heteroaryl or 5 to 10 membered heteroaryl substituted with one or more $R^{1-4}$; the heteroatoms in the 3 to 6 membered heterocycloalkyl are one or more of N, S or O, and the number is 1, 2 or 3; the heteroatoms in the 5 to 10 membered heteroaryl are one or more of N, S or O, and the number is 1, 2 or 3; the heteroatoms in the 5 to 10 membered heteroaryl substituted with one or more $R^{1-4}$ are one or more of N, S or O, and the number is 1, 2 or 3;

$R^{1-1}$, $R^{1-2}$, $R^{1-3}$ and $R^{1-4}$ are independently $C_{1-4}$ alkyl;

R is hydrogen or $C_{1-4}$ alkyl.

2. The compound or the pharmaceutically acceptable salt thereof according to claim 1, wherein the compound as shown in formula I is described in any one of the following situations:

situation 1:

the compound as shown in formula I is a compound as shown in formula Ia, Ib or Ic:

Ia

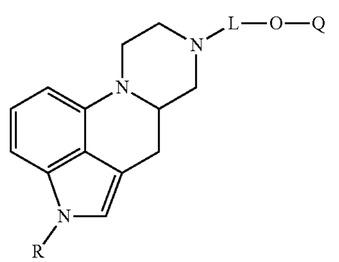

-continued

Ib

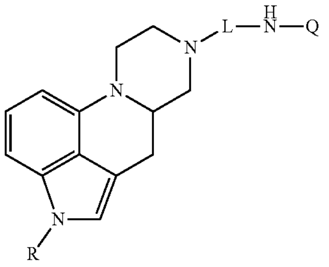

Ic

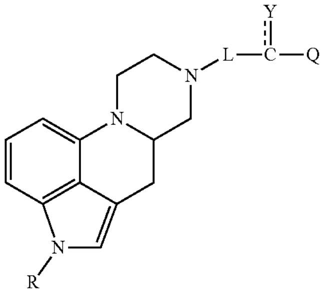

in formula Ic, “ ” represents a double bond or a single bond; Y is hydrogen, hydroxyl or oxygen;

situation 2:

the compound as shown in formula I is a compound as shown in formula Id and/or Ie;

Id

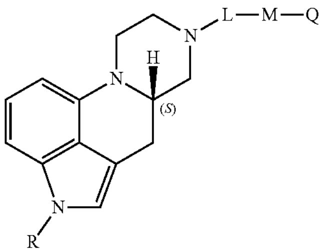

Ie

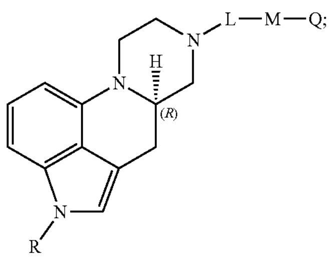

situation 3:

when the compound as shown in formula I has only one chiral center in

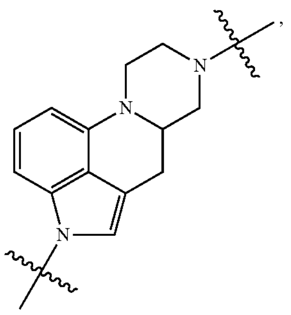

I

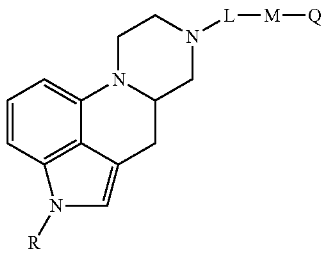

is (+)-I

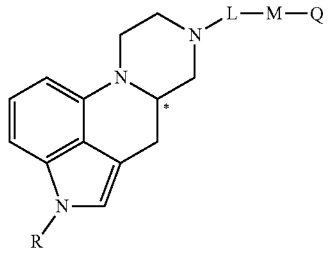

and/or (-)-I

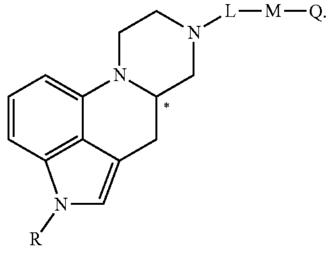

3. The compound or the pharmaceutically acceptable salt thereof according to claim 1, wherein the compound as shown in formula I is described in any one of the following schemes:

scheme 1:

L is $C_{1-10}$ alkylene or —$C_{1-6}$ alkylene-$C_{3-6}$ cycloalkylene-;

M is —O—, —NH— or —$CH_2$—;

Q is $C_{6-18}$ aryl, 5 to 10 membered heteroaryl, 5 to 10 membered heteroaryl substituted with one or more $Q^{1-2}$, —C(═O)$R^1$ or —S(═O)$_2R^2$;

when Q is $C_{6-18}$ aryl, M is —O— or —NH—;

scheme 2:

L is $C_{1-10}$ alkylene or —$C_{1-6}$ alkylene-$C_{3-6}$ cycloalkylene-;

M is —O—, —NH— or —$CH_2$—;

Q is $C_{6-18}$ aryl, 5 to 10 membered heteroaryl, 5 to 10 membered heteroaryl substituted with one or more $Q^{1-2}$, —C(═O)$R^1$ or —S(═O)$_2R^2$;

when Q is $C_{6-18}$ aryl, M is —O— or —NH—;

when M is —O—, $Q^{1-2}$ is $C_{1-4}$ alkyl or hydroxyl;

when the heteroatom in the 5 to 10 membered heteroaryl is O, the number of heteroatoms in the 5 to 10 membered heteroaryl is 1;

scheme 3:

L is $C_{1-10}$ alkylene or —$C_{1-6}$ alkylene-$C_{3-6}$ cycloalkylene-;

M is —O—, —NH— or —$CH_2$—;

Q is $C_{6-18}$ aryl, 5 to 10 membered heteroaryl, 5 to 10 membered heteroaryl substituted with one or more $Q^{1-2}$, —C(═O)$R^1$ or —S(═O)$_2R^2$;

when Q is $C_{6-18}$ aryl, M is —O— or —NH—;

when L is —$C_{1-6}$ alkylene-$C_{3-6}$ cycloalkylene-, the $C_{1-6}$ alkylene in the —$C_{1-6}$ alkylene-$C_{3-6}$ cycloalkylene- is ethylene;

scheme 4:

L is $C_{1-10}$ alkylene or —$C_{1-6}$ alkylene-$C_{3-6}$ cycloalkylene-;

M is —O— or —NH—;

Q is —C(═O)$R^1$ or 5 to 10 membered heteroaryl substituted with one or more $Q^{1-2}$;

$R^1$ is —$NR^{1-1}R^{1-2}$;

scheme 5:

the molecular structure of formula I is as shown in formula Ia:

Ia

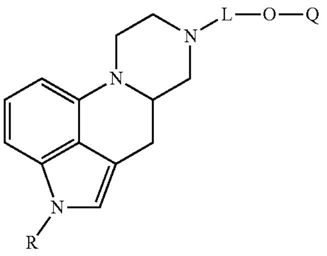

L is $C_{1-10}$ alkylene or $C_{2-10}$ alkenylene;

Q is $C_{6-18}$ aryl substituted with one or more $Q^{1-1}$, 5 to 10 membered heteroaryl or 5 to 10 membered heteroaryl substituted with one or more $Q^{1-2}$;

$Q^{1-1}$ is halogen;

scheme 6:

the molecular structure of formula I is as shown in formula Ib:

Ib

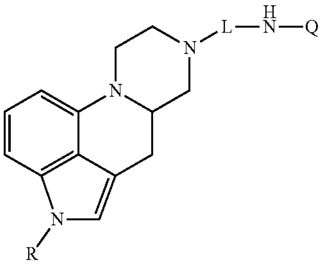

L is —$C_{1-6}$ alkylene-$C_{3-6}$ cycloalkylene-;

Q is —C(═O)$R^1$ or —S(═O)$_2R^2$;

$R^1$ and $R^2$ are independently —$NR^{1-1}R^{1-2}$, 3 to 6 membered heterocycloalkyl, $C_{6-18}$ aryl or 5 to 10 membered heteroaryl;

scheme 7:

the molecular structure of formula I is as shown in formula Ic:

Ic

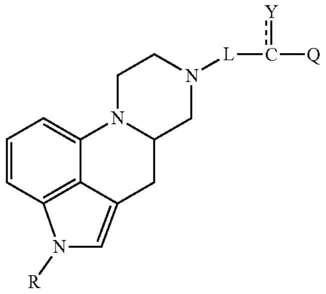

“ ” represents a double bond or a single bond;

Y is hydrogen, hydroxyl or oxygen;

L is $C_{1-10}$ alkylene;

Q is $C_{6-18}$ aryl substituted with one or more $Q^{1-1}$ or 5 to 10 membered heteroaryl substituted with one or more $Q^{1-2}$;

when Q is $C_{6-18}$ aryl substituted with one or more $Q^{1-1}$, Y is hydroxyl or oxygen;

$Q^{1-1}$ is halogen;

$Q^{1-2}$ is independently $C_{1-4}$ alkyl or oxo;

scheme 8:

L is $C_{1-10}$ alkylene, $C_{2-10}$ alkenylene or —$C_{1-6}$ alkylene-$C_{3-6}$ cycloalkylene-;

when M is —(CH—OH)— or —C(═O)—, R is hydrogen;

scheme 9:

L is $C_{1-10}$ alkylene;

M is —O—;

Q is 5 to 10 membered heteroaryl substituted with one or more $Q^{1-2}$;

scheme 10:

L is —$C_{1-6}$ alkylene-$C_{3-6}$ cycloalkylene-;

M is —NH—;

Q is —C(═O)$R^1$;

$R^1$ is —$NR^{1-1}R^{1-2}$;

scheme 11:

the molecular structure of formula I is as shown in formula Ia:

Ia

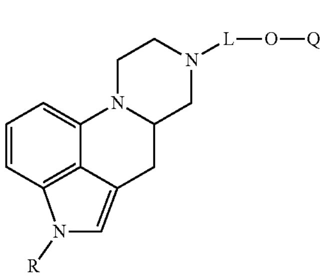

L is $C_{1-10}$ alkylene or $C_{2-10}$ alkenylene;

Q is 5 to 10 membered heteroaryl, or 5 to 10 membered heteroaryl substituted with one or more $Q^{1-2}$:

scheme 12:

the molecular structure of formula I is as shown in formula Ic-1:

Ic-1

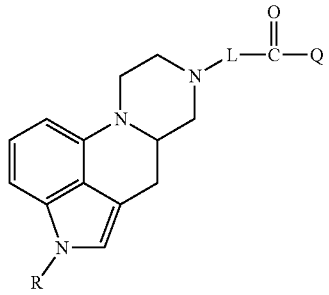

L is $C_{1-10}$ alkylene;

Q is $C_{6-18}$ aryl substituted with one or more $Q^{1-1}$;

$Q^{1-1}$ is halogen;

R is hydrogen;

scheme 13:

the molecular structure of formula I is as shown in formula Ic-2:

Ic-2

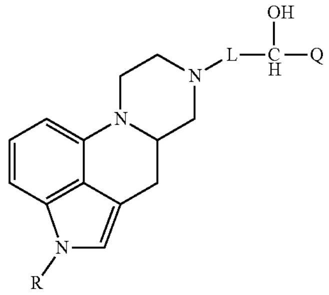

L is $C_{1-10}$ alkylene;

Q is $C_{6-18}$ aryl substituted with one or more $Q^{1-1}$;

$Q^{1-1}$ is halogen;

R is hydrogen;

scheme 14:

the molecular structure of formula I is as shown in formula Ic-3:

Ic-3

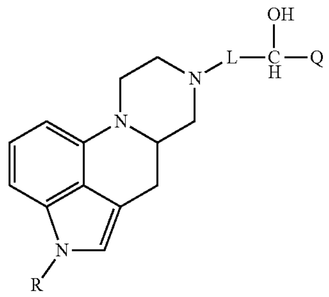

L is $C_{1-10}$ alkylene;

Q is 5 to 10 membered heteroaryl substituted with one or more $Q^{1-2}$;

$Q^{1-2}$ is $C_{1-4}$ alkyl or oxo;

R is hydrogen.

4. The compound or the pharmaceutically acceptable salt thereof according to claim 1, wherein when L is $C_{1-10}$ alkylene, the $C_{1-10}$ alkylene is methylene, ethylene, n-propylene, isopropylene, n-butylene, isobutylene or tert-butylene;

or, when L is $C_{2-10}$ alkenylene, the $C_{2-10}$ alkenylene is $C_{2-4}$ alkenylene;

or, when L is —$C_{1-6}$ alkylene-$C_{3-6}$ cycloalkylene-, the $C_{1-6}$ alkylene is connected to N, and the $C_{3-6}$ cycloalkylene is connected to Q;

or, when L is —$C_{1-6}$ alkylene-$C_{3-6}$ cycloalkylene-, the $C_{1-6}$ alkylene in the —$C_{1-6}$ alkylene-$C_{3-6}$ cycloalkylene- is methylene, ethylene, n-propylene, isopropylene, n-butylene, isobutylene or tert-butylene;

or, when L is —$C_{1-6}$ alkylene-$C_{3-6}$ cycloalkylene-, the $C_{3-6}$ cycloalkylene in the —$C_{1-6}$ alkylene-$C_{3-6}$ cycloalkylene is cyclopropylene, cyclobutylene, cyclopentylene or cyclohexylene;

or, when Q is $C_{6-18}$ aryl, the $C_{6-18}$ aryl is phenyl, naphthyl, anthracenyl or phenanthryl;

or, when Q is $C_{6-18}$ aryl substituted with $Q^{1-1}$, the $C_{6-18}$ aryl is phenyl, naphthyl, anthracenyl or phenanthryl;

or, when Q is $C_{6-18}$ aryl substituted with $Q^{1-1}$, the number of $Q^{1-1}$ is 1 or 2;

or, when $Q^{1-1}$ is halogen, the halogen is F, Cl, Br or I;

or, when Q is 5 to 10 membered heteroaryl, the 5 to 10 membered heteroaryl is 9 or 10 membered heteroaryl, and the number of heteroatoms is 1 or 2;

or, when Q is 5 to 10 membered heteroaryl substituted with one or more $Q^{1-2}$, the 5 to 10 membered heteroaryl is 9 or 10 membered heteroaryl, the heteroatom is N and/or O, the number of heteroatoms is 1 or 2;

or, when Q is $C_{6-18}$ aryl substituted with $Q^{1-1}$, the number of $Q^{1-1}$ is 1 or 2;

or, when $Q^{1-2}$ is $C_{1-4}$ alkyl, the $C_{1-4}$ alkyl is methyl, ethyl, n-propyl, isopropyl, n-butyl, isobutyl or tert-butyl;

or, when $R^1$ and $R^2$ are independently 3 to 6 membered heterocycloalkyl, the 3 to 6 membered heterocycloalkyl is piperidinyl or pyrrolidinyl;

or, when $R^1$ is 3 to 6 membered heterocycloalkyl, the 3 to 6 membered heterocycloalkyl is connected to carbonyl through a heteroatom;

or, when $R^1$ and $R^2$ are independently $C_{6-18}$ aryl, the $C_{6-18}$ aryl is phenyl, naphthyl, anthracenyl or phenanthryl;

or, when $R^1$ and $R^2$ are independently $C_{6-18}$ aryl substituted with $R^{1-3}$, the $C_{6-18}$ aryl is phenyl, naphthyl, anthracenyl or phenanthryl;

or, when $R^1$ and $R^2$ are independently 5 to 10 membered heteroaryl, the 5 to 10 membered heteroaryl is 9 or 10 membered heteroaryl, the heteroatom is N, and the number of heteroatoms is 1 or 2;

or, when $R^{1-1}$, $R^{1-2}$, $R^{1-3}$ and $R^{1-4}$ are independently $C_{1-4}$ alkyl, the $C_{1-4}$ alkyl is methyl, ethyl, n-propyl, isopropyl, n-butyl, isobutyl, sec-butyl or tert-butyl;

or, when R is $C_{1-4}$ alkyl, the $C_{1-4}$ alkyl is methyl, ethyl, n-propyl, isopropyl, n-butyl, isobutyl, sec-butyl or tert-butyl.

5. The compound or the pharmaceutically acceptable salt thereof according to claim 4, wherein when L is —$C_{1-6}$ alkylene-$C_{3-6}$ cycloalkylene-, the —$C_{1-6}$ alkylene-$C_{3-6}$ cycloalkylene- is

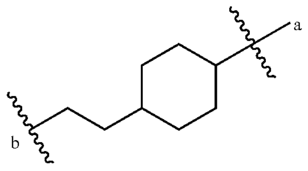

or

-continued

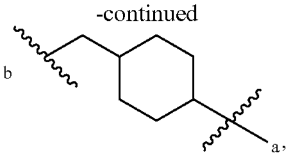

wherein a end is connected to Q, and b end is connected to N;

or, when Q is $C_{6-18}$ aryl substituted with $Q^{1-1}$, the $C_{6-18}$ aryl substituted with $Q^{1-1}$ is

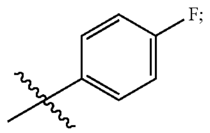 [SMILES: *c1ccc(F)cc1]

or, when Q is 5 to 10 membered heteroaryl substituted with one or more $Q^{1-2}$, the 5 to 10 membered heteroaryl substituted with one or more $Q^{1-2}$ is

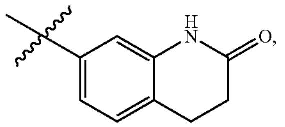

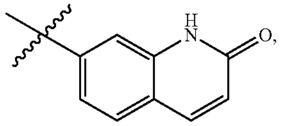

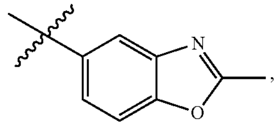

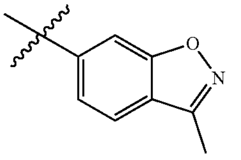

or

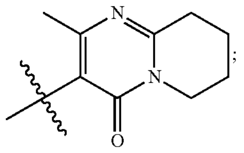

or, when $R^1$ is 3 to 6 membered heterocycloalkyl, the 3 to 6 membered heterocycloalkyl is

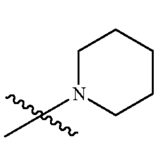

or

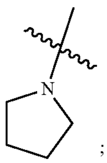

;

or,

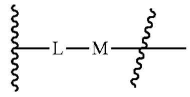

is

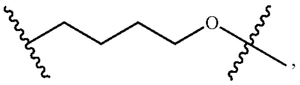

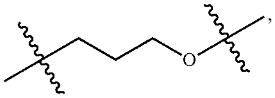

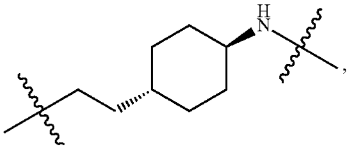

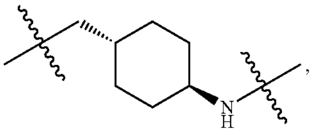

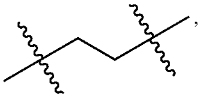

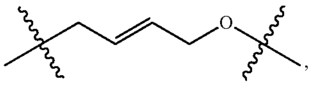

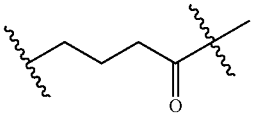

or

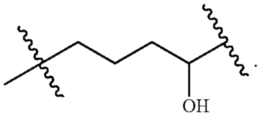

and when Q is $C_{6-18}$ aryl or $C_{6-18}$ aryl substituted with one or more $Q^{1-1}$,

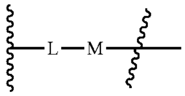

is

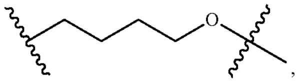

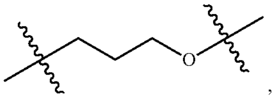

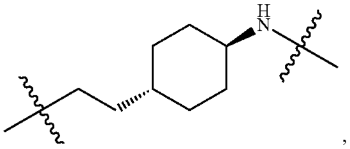

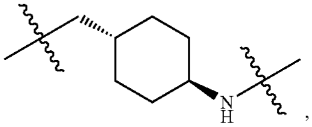

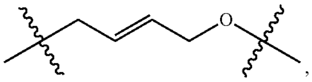

-continued

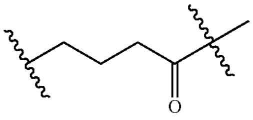

or

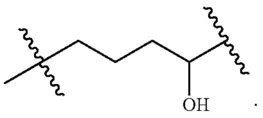

6. The compound or the pharmaceutically acceptable salt thereof according to claim 1, wherein L is $C_{1-10}$ alkylene, $C_{2-10}$ alkenylene or —$C_{1-6}$ alkylene-$C_{3-6}$ cycloalkylene;

or, M is —O—, —NH— or —$CH_2$—; and when Q is $C_{6-18}$ aryl or $C_{6-18}$ aryl substituted with one or more $Q^{1-1}$, M is —O— or —NH—;

or, $Q^{1-1}$ is halogen;

or, $R^1$ is —$NR^{1-1}R^{1-2}$, 3 to 6 membered heterocycloalkyl, $C_{6-18}$ aryl or 5 to 10 membered heteroaryl;

or, R is hydrogen.

7. The compound or the pharmaceutically acceptable salt thereof according to claim 1, wherein the compound as shown in formula I is any one of the following compounds:

I-1

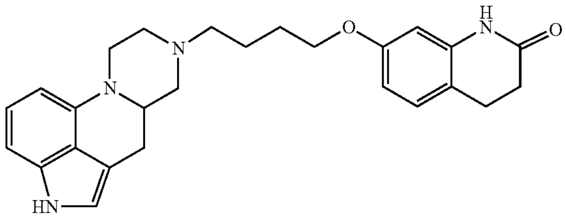

I-2

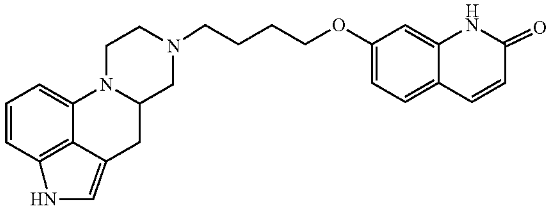

I-3

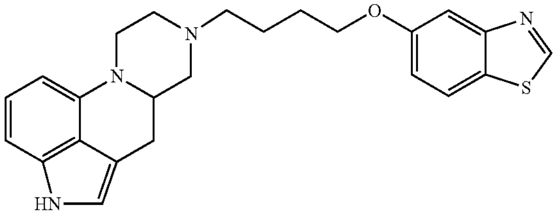

I-4

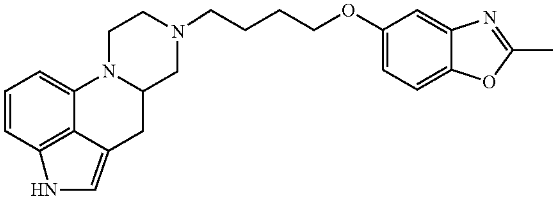

-continued
I-5
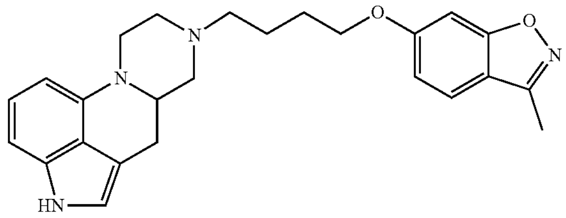
I-6
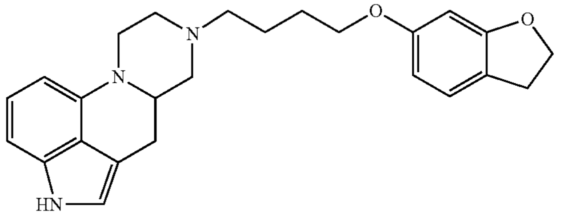
I-7
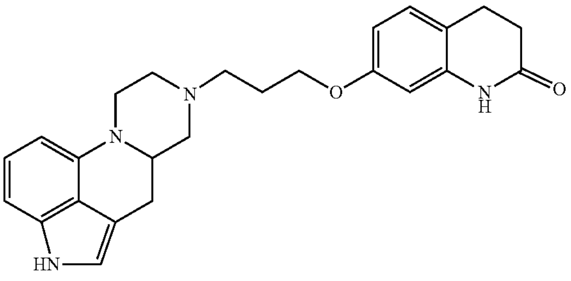
I-8
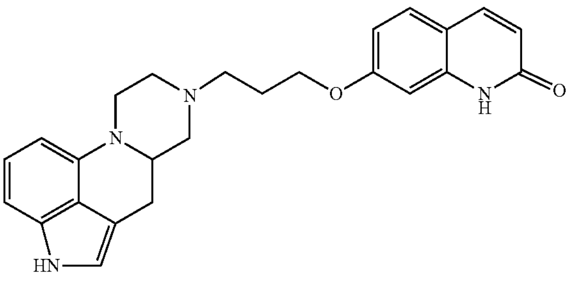
I-9
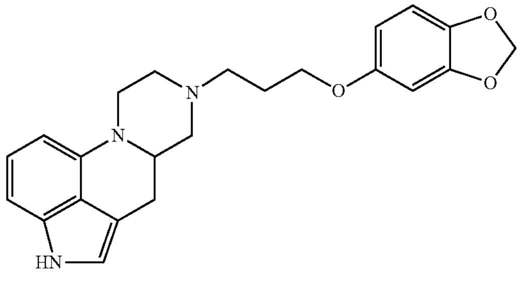
-continued
I-10
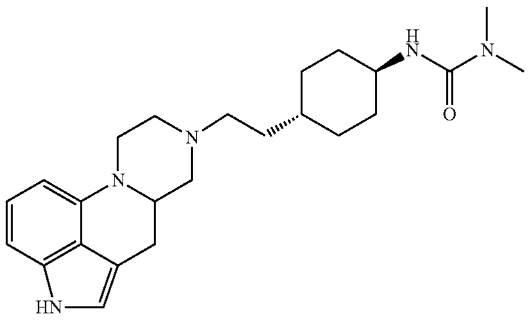
I-11
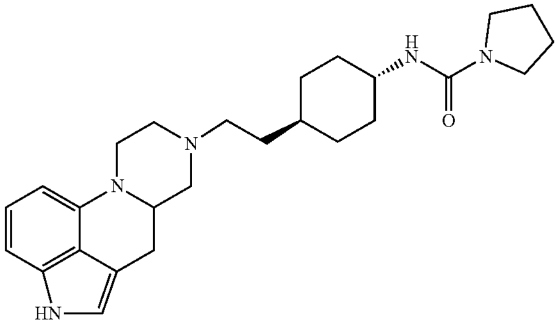
I-12
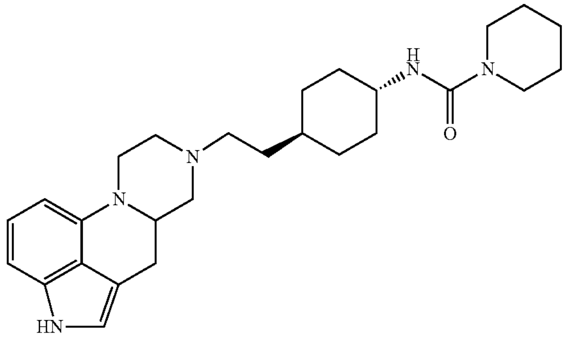
I-13
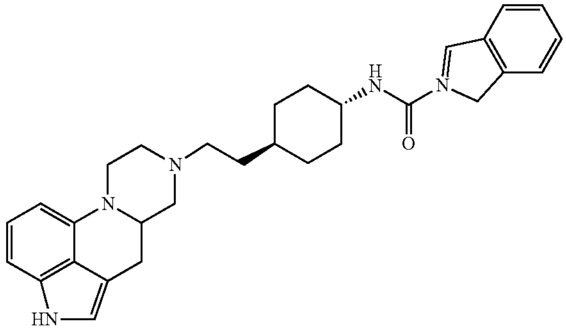

-continued
I-14
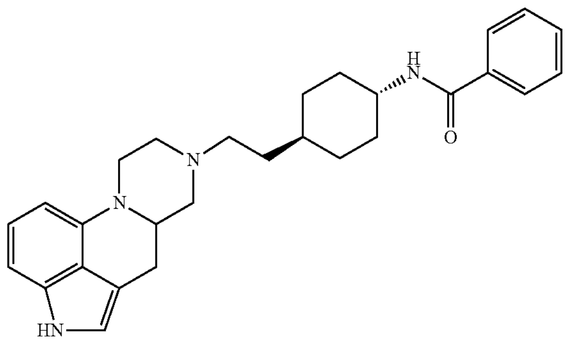
I-15
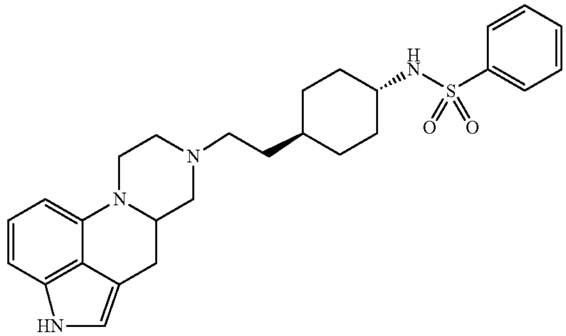
I-16
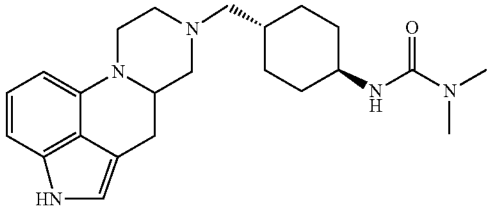
I-17
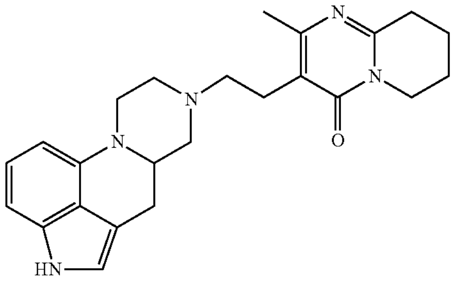
I-18
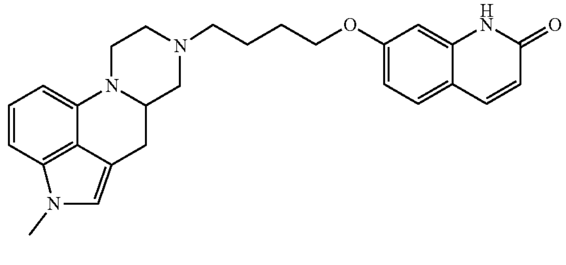
-continued
I-19
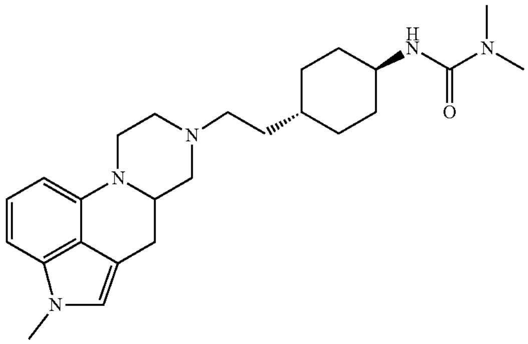
I-20
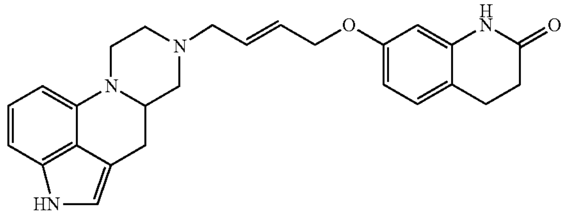
I-21
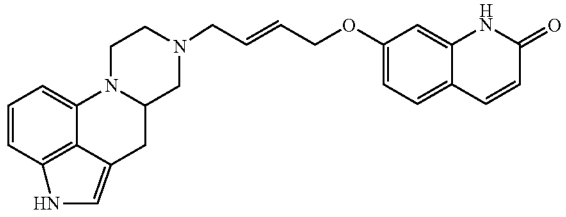
I-22
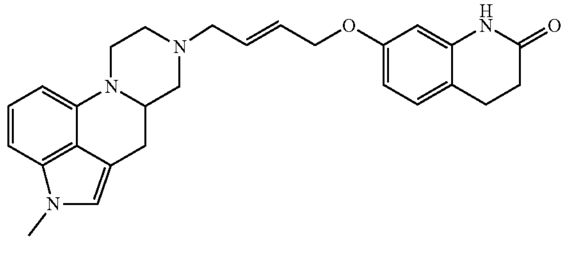
I-23
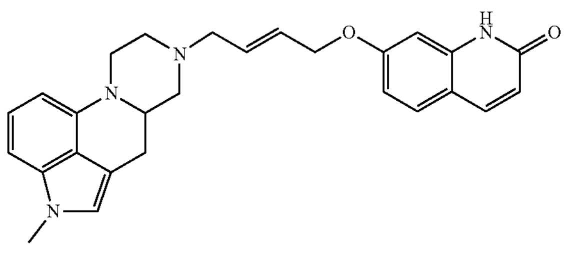

-continued

I-24

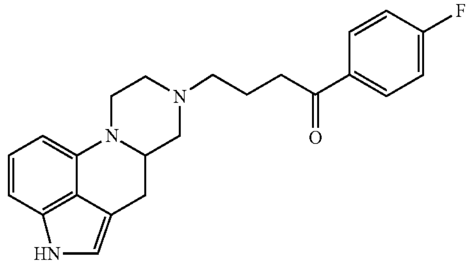

I-25

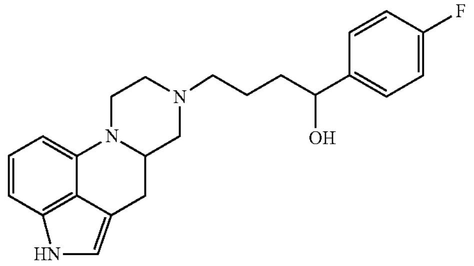

I-26

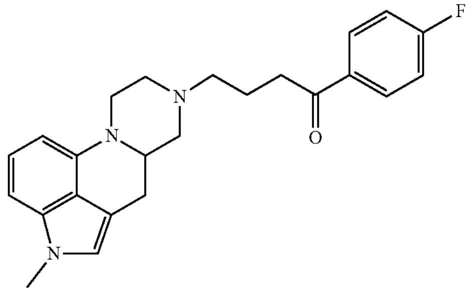

I-27

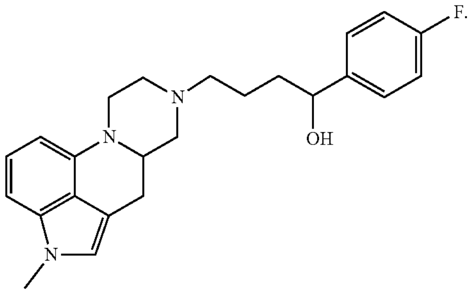

8. A crystal as shown in the formula pNs-(+)-I-10, wherein the crystal system of which belongs to the triclinic crystal system, the P1 space group, and the unit cell parameters are a=9.315 Å, b=6.564 Å, c=23.792 Å, α=90.15°, β=99.368°, γ=90.25°;

pNs-(+)-I-10

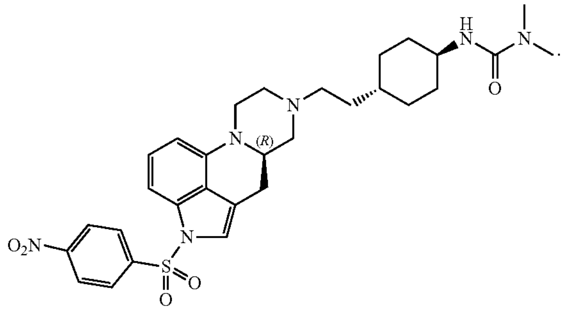

9. A pharmaceutical composition, which comprises the compound or the pharmaceutically acceptable salt thereof according to claim 1 and a pharmaceutical adjuvant.

10. A method for treating diseases related to dopamine D2 receptors or disease M, which comprises administering to a subject a therapeutically effective amount of substance A;

the disease M is Parkinson's disease, schizophrenia, depression or prolactinoma;

the substance A is the compound or the pharmaceutically acceptable salt thereof according to claim 1.

11. The method according to claim 10, wherein the disease M is schizophrenia or depression.

12. A method for treating diseases related to dopamine D2 receptors or disease M, which comprises administering to a subject a therapeutically effective amount of the crystal as shown in formula pNs-(+)-I-10 according to claim 8;

the disease M is Parkinson's disease, schizophrenia, depression or prolactinoma.

13. A method for activating dopamine D2 receptors, which comprises administering to a subject the compound or the pharmaceutically acceptable salt thereof according to claim 1.

14. The compound or the pharmaceutically acceptable salt thereof according to claim 2, wherein in situation 2:

the compound as shown in formula I is a compound as shown in formula Id;

Id

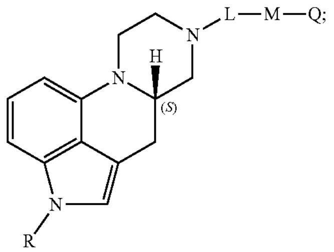

in situation 3:

when the compound as shown in formula I has only one chiral center in

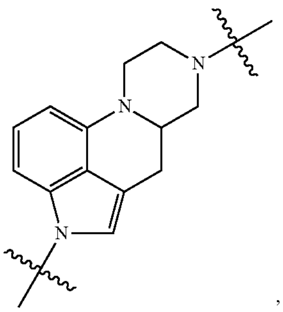

,

I

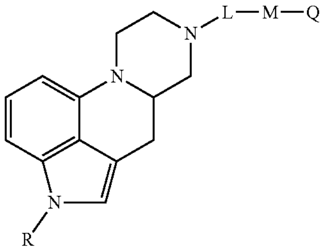

is (-)-I

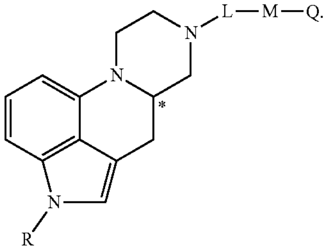

15. The compound or the pharmaceutically acceptable salt thereof according to claim 4, wherein when L is $C_{1-10}$ alkylene, the $C_{1-10}$ alkylene is

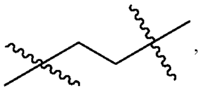

,

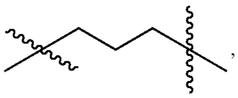

, or

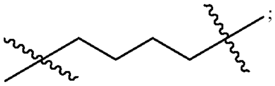

;

or, when L is $C_{2-10}$ alkenylene, the $C_{2-10}$ alkenylene is

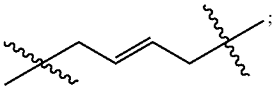 [SMILES: *C/C=C/C*]

;

or, when L is —$C_{1-6}$ alkylene-$C_{3-6}$ cycloalkylene-, the $C_{1-6}$ alkylene in the —$C_{1-6}$ alkylene-$C_{3-6}$ cycloalkylene- is methylene or

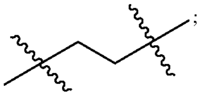 [SMILES: *CC*]

;

or, when L is —$C_{1-6}$ alkylene-$C_{3-6}$ cycloalkylene-, the $C_{3-6}$ cycloalkylene in the —$C_{1-6}$ alkylene-$C_{3-6}$ cycloalkylene is

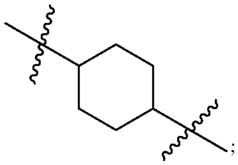 [SMILES: *C1CCC(*)CC1]

;

or, when Q is $C_{6-18}$ aryl, the $C_{6-18}$ aryl is phenyl;

or, when Q is $C_{6-18}$ aryl substituted with $Q^{1-1}$, the $C_{6-18}$ aryl is phenyl;

or, when $Q^{1-1}$ is halogen, the halogen is F;

or, when Q is 5 to 10 membered heteroaryl, the 5 to 10 membered heteroaryl is

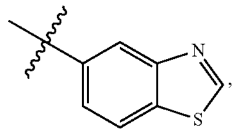

,

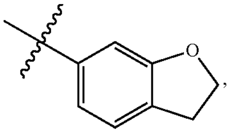

,

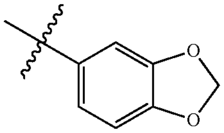

or

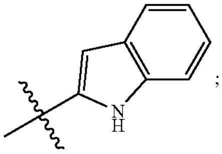

;

or, when Q is 5 to 10 membered heteroaryl substituted with one or more $Q^{1-2}$, the 5 to 10 membered heteroaryl is tetrahydroquinolyl, quinolinyl, benzoxazolyl, benzisoxazolyl or tetrahydropyridopyrimidinyl;

or, when $Q^{1-2}$ is $C_{1-4}$ alkyl, the $C_{1-4}$ alkyl is methyl;

or, when $R^1$ and $R^2$ are independently 3 to 6 membered heterocycloalkyl, the 3 to 6 membered heterocycloalkyl is pyrrolidinyl;

or, when $R^1$ and $R^2$ are independently $C_{6-18}$ aryl, the $C_{6-18}$ aryl is phenyl;

or, when $R^1$ and $R^2$ are independently $C_{6-18}$ aryl substituted with $R^{1-3}$, the $C_{6-18}$ aryl is phenyl;

or, when $R^1$ and $R^2$ are independently 5 to 10 membered heteroaryl, the 5 to 10 membered heteroaryl is indolyl;

or, when $R^{1-1}$, $R^{1-2}$, $R^{1-3}$ and $R^{1-4}$ are independently $C_{1-4}$ alkyl, the $C_{1-4}$ alkyl is methyl;

or, when R is $C_{1-4}$ alkyl, the $C_{1-4}$ alkyl is methyl.

16. The compound or the pharmaceutically acceptable salt thereof according to claim 15, wherein when L is $C_{1-10}$ alkylene, the $C_{1-10}$ alkylene is

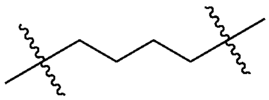

;

or, when L is —$C_{1-6}$ alkylene-$C_{3-6}$ cycloalkylene-, the $C_{1-6}$ alkylene in the —$C_{1-6}$ alkylene-$C_{3-6}$ cycloalkylene- is

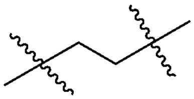

;

17. The compound or the pharmaceutically acceptable salt thereof according to claim 5, wherein when L is —$C_{1-6}$ alkylene-$C_{3-6}$ cycloalkylene-, the —$C_{1-6}$ alkylene-$C_{3-6}$ cycloalkylene- is

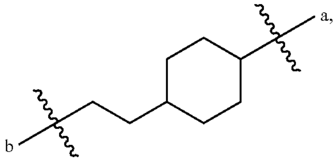 [SMILES: *CCC1CCC(*)CC1]

wherein a end is connected to Q, and b end is connected to N.

18. The compound or the pharmaceutically acceptable salt thereof according to claim 6, wherein L is $C_{1-10}$ alkylene or —$C_{1-6}$ alkylene-$C_{3-6}$ cycloalkylene;

or, $R^1$ is —$NR^{1-1}R^{1-2}$, 3 to 6 membered heterocycloalkyl or $C_{6-18}$ aryl.

19. The compound or the pharmaceutically acceptable salt thereof according to claim 7, wherein the compound as shown in formula I is any one of the following compounds:

(+)-(R)-I-10

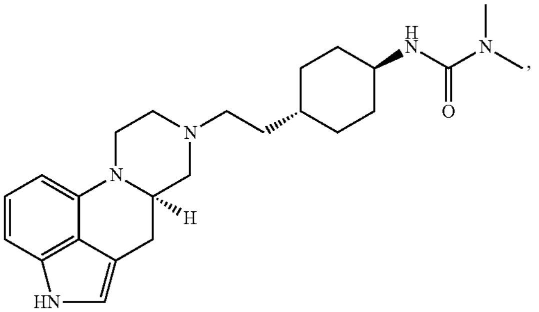

-continued (+)-(S)-I-10

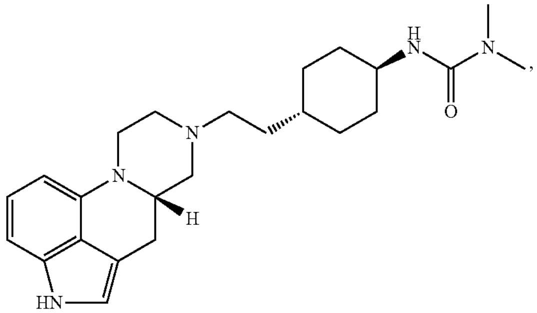

I-2

“ 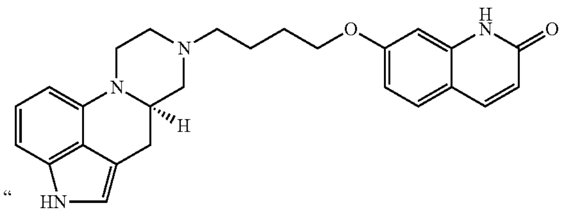

with optical rotation of +50.33° and/or retention time of 5.805 min under the following chiral preparation conditions” or

I-2

“ 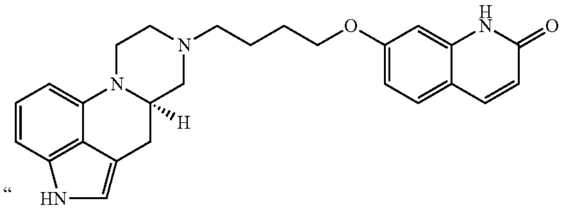

with optical rotation of −45.00° and/or retention time of 7.60 min under the following chiral preparation conditions”;

the chiral preparation conditions: chromatographic column: chiral column CHIRALCEL OD, column volume: 5.0 cm×25 cm, 10 μm filler; mobile phase: MeOH/diethylamine=100/0.1; flow rate: 30 mL/min; wavelength: UV 214 nm; temperature: 38° C.

20. The method according to claim 12, wherein the disease M is schizophrenia or depression.

* * * * *